United States Patent
Waldmann et al.

(10) Patent No.: US 12,060,362 B2
(45) Date of Patent: Aug. 13, 2024

(54) INHIBITORS OF GLUCOSE TRANSPORTERS (GLUTs)

(71) Applicants: LEAD DISCOVERY CENTER GMBH, Dortmund (DE); MAX-PLANCK-GESELLSCHAFT ZUR FÖRDERUNG DER WISSENSCHAFTEN E.V., Munich (DE)

(72) Inventors: Herbert Waldmann, Dortmund (DE); Gunther Zischinsky, Dortmund (DE); Peter Nussbaumer, Dortmund (DE); Slava Ziegler, Dortmund (DE); Melanie Schwalfenberg, Cork (IE); Javier de Ceballos Cerrajeria, Vaud (CH); Elena Sabrina Reckzeh, Dortmund (DE); George Karageorgis, Essen (DE)

(73) Assignees: LEAD DISCOVERY CENTER GMBH, Dortmund (DE); MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 585 days.

(21) Appl. No.: 17/273,549

(22) PCT Filed: Sep. 5, 2019

(86) PCT No.: PCT/EP2019/073761
§ 371 (c)(1),
(2) Date: Mar. 4, 2021

(87) PCT Pub. No.: WO2020/049124
PCT Pub. Date: Mar. 12, 2020

(65) Prior Publication Data
US 2021/0198269 A1 Jul. 1, 2021

(30) Foreign Application Priority Data
Sep. 5, 2018 (EP) .................. 18192653

(51) Int. Cl.
*C07D 491/08* (2006.01)
*A61K 31/529* (2006.01)

(52) U.S. Cl.
CPC .................. *C07D 491/08* (2013.01)

(58) Field of Classification Search
CPC ............ C07D 491/08; A61K 31/529
USPC ......................... 544/250; 514/267
See application file for complete search history.

(56) References Cited

PUBLICATIONS

Karageorgis et al., "Chromopynones are pseudo natural product glucose uptake inhibitors targeting glucose transporters GLUT-1 and -3", 2018, Nature Chemistry, vol. 10, pp. 1103-1111. (Year: 2018).*

Cheng et al., "Solvent-free synthesis of monastrol derivatives catalyzed by NaHSO$_4$" J. Heterocyclic Chem. (2010) 47(3):624-628.

Crane et al., "Capturing Biological Activity in Natural Product Fragments by Chemical Synthesis" Ange. Chem. Int. Ed. (2016) 55(12):3882-3902.

Hatano et al., "Chiral Lithium Salts of Phosphoric Acids as Lewis Acid-Base Conjugate Catalysts for the Enantioselective Cyanosilylation of Ketones" Advanced Synthesis & Catalysis (2008) 350(11-12):1776-1780.

Jacobs et al., "Glucose uptake is limiting in T cell activation and requires CD28-mediated Akt-dependent and independent pathways" J. Immunol. (2008) 180(7):4476-4486.

Karageorgis et al., "Chromopynones are pseudo natural products glucose uptake inhibitors targeting glucose transporters GLUT-1 and -3" Nature Chemistry (2018) 10(11):1103-1111 and Supporting Information.

Klussmann et al. "Synthesis of TRIP and Analysis of Phosphate Salt Impurities" Synlett (2010) 2010(14):2189-2192.

Li, et al., "Highly Enantioselective Organocatalytic Biginelli and Biginelli-Like Condensations: Reversal of the Stereochemistry by Tuning the 3,3'-Disubstituents of Phosphoric Acids" J. Am. Chem. Soc. (2009) 131(42):15301-15310.

MacIntyre et al., "The glucose transporter Glut1 is selectively essential for CD4 T cell activation and effector function" Cell Metab. (2014) 20(1):61-72.

Michalek et al., "Cutting edge: distinct glycolytic and lipid oxidative metabolic programs are essential for effector and regulatory CD4+ T cell subsets" J. Immunol. (2011) 186:3299-3303.

Murray et al., "The rise of fragment-based drug discovery" Nature Chemistry (2009) 1(3):187-192.

(Continued)

*Primary Examiner* — Charanjit Aulakh
(74) *Attorney, Agent, or Firm* — Knobbe, Martens, Olson & Bear, LLP

(57) ABSTRACT

The present invention relates to 2,6-methanobenzo[g][1]oxacin-4-one compounds and their analog compounds and pharmaceutically acceptable salts thereof as selective inhibitor of glucose transporters 1 and 3 (GLUTs 1 and 3), to methods of preparing said compounds, and to the use thereof as pharmaceutically active agents, especially for the prophylaxis and/or treatment of metabolic diseases, immunological diseases, autoimmune diseases, inflammation, graft versus host disease, cancer, and metastasis thereof. Furthermore, the present invention is directed to pharmaceutical composition comprising at least one of 2,6-methanobenzo[g][1]oxacin-4-one compounds and their analog compounds.

9 Claims, No Drawings

(56) References Cited

PUBLICATIONS

Tung et al., "Peptide 2-formylthiophenol esters do not proceed through a Ser/Thr ligation pathway, but participate in a peptide aminolysis to enable peptide condensation and cyclization" Organic & Biomolecular Chemistry (2015) 13(25):6922-6926.
Simplicio et al., "Prodrugs for Amines" Molecules (2008) 13:519-547.
"Pro-drugs as Novel Drug Delivery Systems" by T. Higuchi and W. Stella, ACS Symposium Series vol. 14, 1975 (ISBN13: 9780841202917).
"Prodrugs of Amines" by J.P. Krise and R. Oliyai (Biotechnology: Pharmaceutical Aspects, 2007, vol. V, Part III, 101-131.
International Search Report and Written Opinion mailed Oct. 22, 2019 for PCT Application No. PCT/EP2019/073761, filed Sep. 6, 2019.

\* cited by examiner

INHIBITORS OF GLUCOSE TRANSPORTERS (GLUTs)

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including PCT Application No. PCT/EP2019/073761, filed Sep. 5, 2019, and EP Application No. 18192653.6, filed Sep. 5, 2018.

The present invention relates to 2,6-methanobenzo[g][1]oxacin-4-one compounds and their analog compounds and pharmaceutically acceptable salts thereof as selective inhibitor of glucose transporters 1 and 3 (GLUTs 1 and 3), to methods of preparing said compounds, and to the use thereof as pharmaceutically active agents, especially for the prophylaxis and/or treatment of metabolic diseases, immunological diseases, autoimmune diseases, inflammation, graft versus host disease, cancer, and metastasis thereof. Furthermore, the present invention is directed to pharmaceutical composition comprising at least one of 2,6-methanobenzo[g][1]oxacin-4-one compounds and their analog compounds.

BACKGROUND OF THE INVENTION

Glucose is an essential substrate for metabolism in most cells. Because glucose is a polar molecule, transport through biological membranes requires specific transport proteins. Basal glucose transporters (GLUTs) function as glucose channels and are required for maintaining the basic glucose needs of cells. These GLUTs are constitutively expressed and functional in cells and are not regulated by (or sensitive to) insulin. All cells use both glycolysis and oxidative phosphorylation in mitochondria but rely overwhelmingly on oxidative phosphorylation when oxygen is abundant, switching to glycolysis at times of oxygen deprivation (hypoxia), as it occurs in cancer. In glycolysis, glucose is converted to pyruvate and two ATP molecules are generated in the process. Cancer cells, because of their faster proliferation rates, are predominantly in a hypoxic (low oxygen) state. Therefore, cancer cells use glycolysis (lactate formation) as their predominant glucose metabolism pathway. Such a glycolytic switch not only gives cancer higher potentials for metastasis and invasiveness, but also increases cancer's vulnerability to external interference in glycolysis. The reduction of basal glucose transport is likely to restrict glucose supply to cancer cells, leading to glucose deprivation that forces cancer cells to slow down growth or to starve.

It is long recognized that cancer cells display increased glucose uptake and metabolism. In a rate-limiting step for glucose metabolism, the glucose transporter (GLUT) proteins facilitate glucose uptake across the plasma membrane. Fourteen members of the GLUT protein family have been identified in humans.

The tissue-specific pattern of GLUT isoform expression likely reflects differing needs for glucose transport by various tissues. Myocytes must respond expeditiously to increased metabolic demand. A basal isoform, GLUT1, and the insulin-regulatable glucose transporter, GLUT4, have been demonstrated in human myocytes. GLUT3 has a high affinity for glucose, and is present in human cardiac myocytes.

Malignant cells are known to have accelerated metabolism, high glucose requirements, and increased glucose uptake. Transport of glucose across the plasma membrane of mammalian cells is the first rate-limiting step for glucose metabolism and is mediated by facilitative glucose transporter (GLUT) proteins. Increased glucose transport in malignant cells has been associated with increased and deregulated expression of glucose transporter proteins, with overexpression of GLUT1 and/or GLUT3 a characteristic feature. Oncogenic transformation of cultured mammalian cells causes a rapid increase of glucose transport and GLUT1 expression via interaction with GLUT1 promoter enhancer elements. In human studies, high levels of GLUT1 expression in tumors have been associated with poor survival. Studies indicate that glucose transport in breast cancer is not fully explained by GLUT1 or GLUT3 expression, suggesting involvement of another glucose transporter. Hypoxia can increase GLUT1 levels and glucose uptake. Estradiol and epidermal growth factor, both of which can play a role in breast cancer cell growth, increase glucose consumption.

Glucose uptake is mediated by glucose transporters (GLUTs) and Class 1 GLUTs (GLUT-1-4) are upregulated in various tumors. GLUT-1 and -3 are strongly upregulated in the majority of cancers, e.g. lung, brain, breast, bladder, cervical, colorectal, esophageal, hepatocellular, ovarian renal cell, pancreatic, prostate etc. Moreover, GLUT-1 and GLUT-3 have been linked to poor survival and tumor aggressiveness.

Glucose uptake provides a key metabolic control point through the Glut family of facilitative glucose transporter. In vitro stimulated murine and human T cells express high levels of GLUT 1. CD4 T cell activation leads to rapid proliferation and differentiation into effector (Teff; including Th1, Th2, and Th17) or regulatory (Treg) cells that mediate or control immunity. Teff cells maintain higher levels of GLUT 1 than Treg. GLUT 1 can promote Teff, as transgenic GLUT 1 overexpression selectively increased Teff frequency and led to inflammatory disease (Jacobs S R, et al., *J. Immunol.* 2008, 180, pp. 4476-4486; Michalek R D. et al., *J. Immunol.* 2011, 186, pp. 3299-3303; Andrew N. Macintyre et al., *Cell Metab.* 2014, 20(1), pp. 61-72)

It is object of the present invention to provide compounds as GLUTs inhibitors, preferred Class 1 GLUTs (GLUTs 1-4 and 14), especially selective inhibitors of GLUTs 1 and 3, and/or pharmaceutically acceptable salts thereof which can be used as pharmaceutically active agents, especially for prophylaxis and/or treatment of metabolic diseases, immunological diseases, autoimmune diseases, inflammation, graft versus host disease cancers, and metastasis thereof, as well as compositions comprising at least one of those compounds and/or pharmaceutically acceptable salts thereof as pharmaceutically active ingredients.

The objective of the present invention is solved by the teaching of the independent claims. Further advantageous features, aspects and details of the invention are evident from the dependent claims, the description, the figures, and the examples of the present application.

DESCRIPTION OF THE INVENTION

The 1,3,5-benzoxadiazocin-4-one (or chromopynones) compounds according to the present invention are defined by the general formula (I):

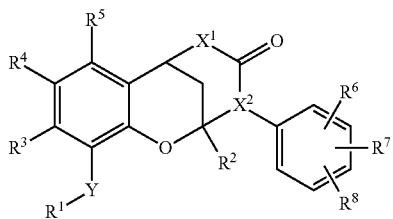
(I)
wherein
$X^1$ is —O— or —NR$^N$—;
$R^N$ is —H, —CH$_3$, —CH$_2$CH$_3$, —CH$_2$CH$_2$CH$_3$, —CH(CH$_3$)$_2$, -cyclo-C$_3$H$_5$, —C$_4$H$_9$, —CH$_2$CH(CH$_3$)$_2$, —C(CH$_3$)$_3$, or -cyclo-C$_4$H$_7$;
$X^2$ is
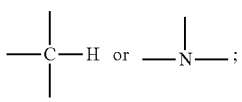
Y is a bond, —O— or —S—;
$R^1$ represents —(CH$_2$)$_m$-A;
m is an integer selected from 0, 1, 2 or 3;
A represents $C_3$-$C_{12}$ mono-, bi-, tri-, tetra-, or pentacycloalkyl, or
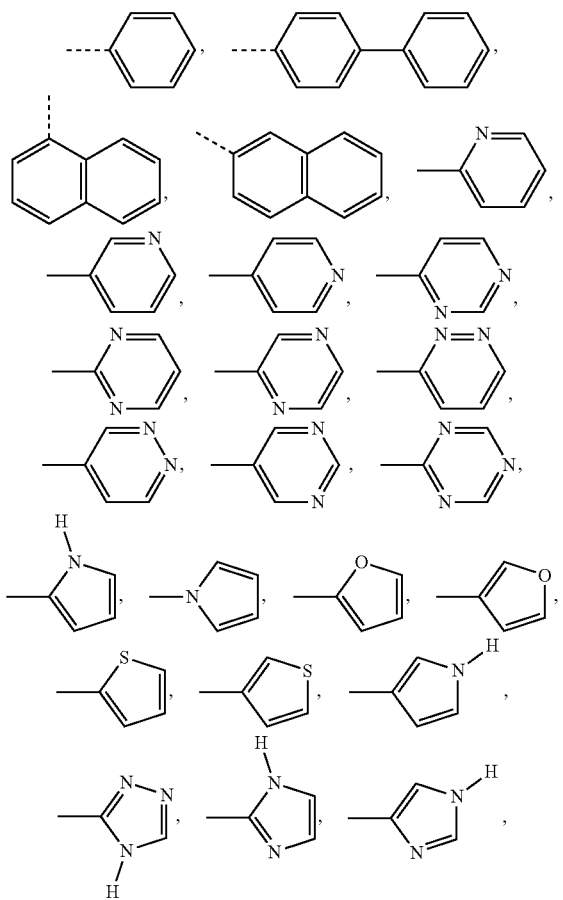
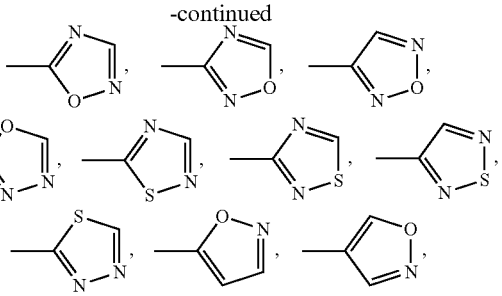
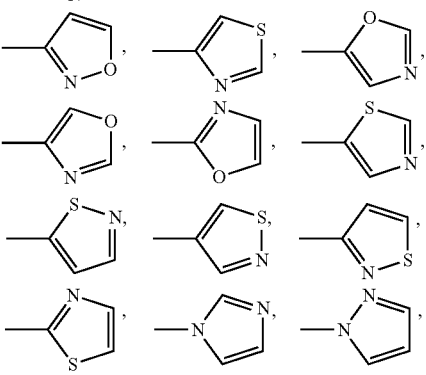
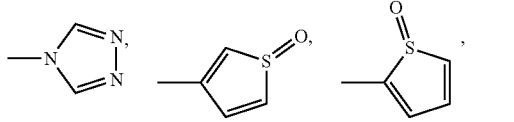
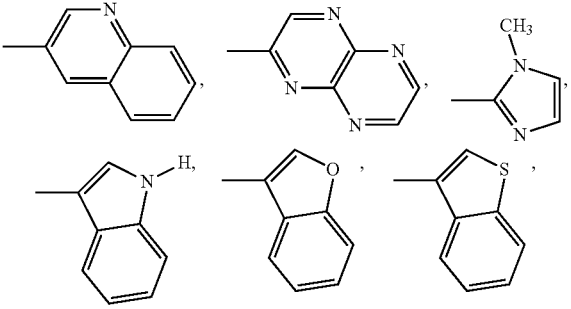
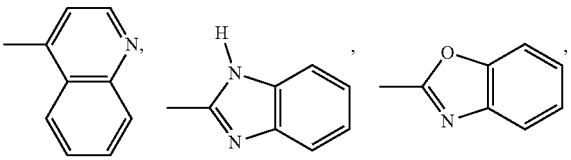
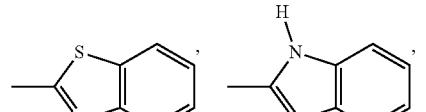
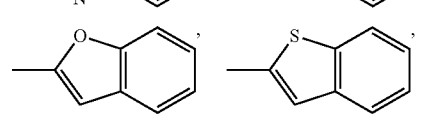
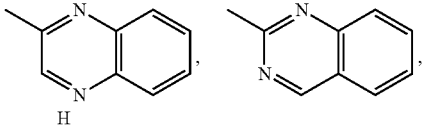
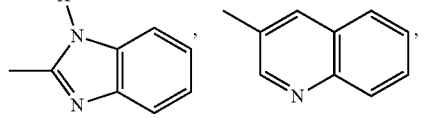

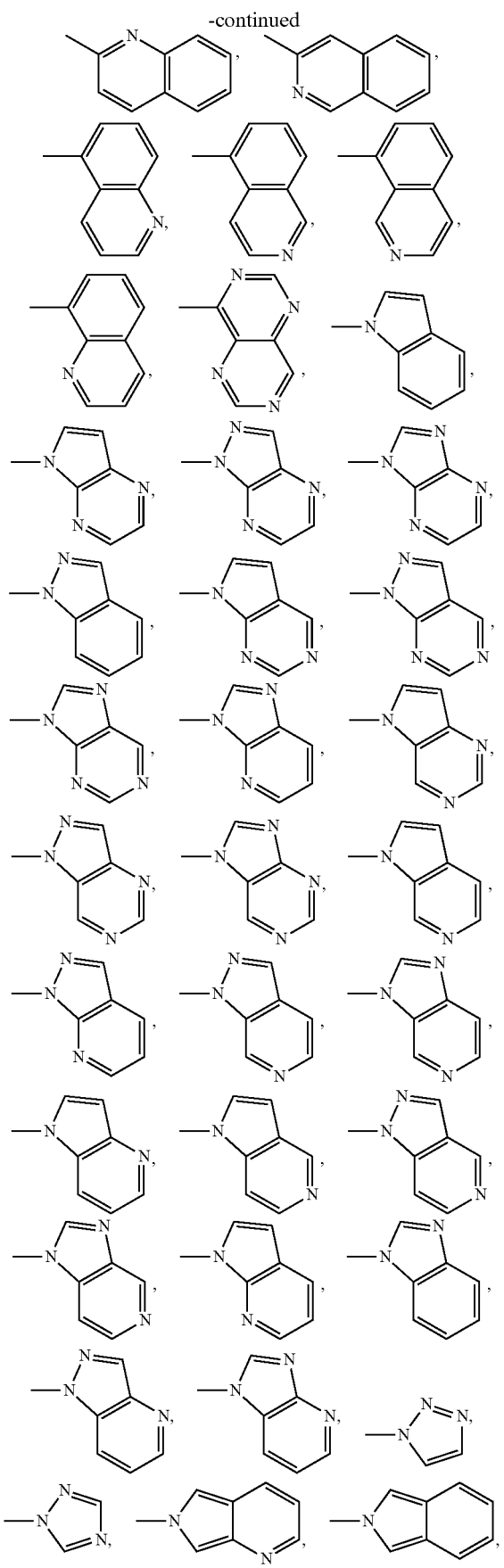

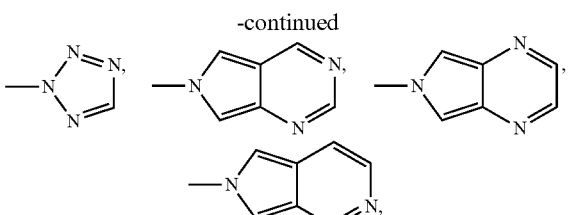

wherein these residues can be substituted with 1 to 3 substituents selected from $Z^1$, $Z^2$, $Z^3$;

$R^2$ represents —H, —CH$_3$ or —CH$_2$CH$_3$;

$R^3$, $R^4$, $R^5$, $R^6$ and $R^7$ represent independently of each other —H, —F, —Cl, —CN, —CH$_3$ or —CF$_3$;

$R^8$ represents —CO—O—(CH$_2$)$_n$—B, —CO—O—(CH$_2$)$_n$—OB, —CO—NR'—(CH$_2$)$_n$—B, —CO—NR'—(CH$_2$)$_n$—OB, —CO—B* or —R$^7$;

R' represents —H or —CH$_3$;

n is an integer selected from 0, 1, 2 or 3;

B* represents

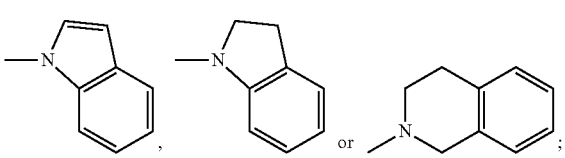

wherein these residues can be substituted with 1 to 3 substituents selected from $Z^4$, $Z^5$, $Z^6$;

B represents C1-C7-alkyl or C3-C7-alkyl, C3-C6-cycloalkyl,

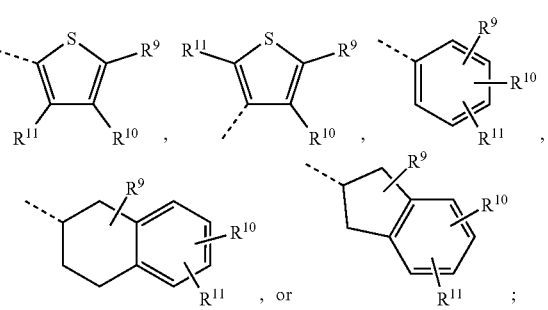

$R^9$, $R^{10}$, $R^{11}$, and $Z^1$-$Z^9$, represent independently of each other —H, —F, —Cl, —CN, —NO$_2$, —NH$_2$, —CF$_3$, —CH$_3$, —CH$_2$CH$_3$, —CH$_2$CH$_2$CH$_3$, —CH(CH$_3$)$_2$, —C(CH$_3$)$_3$, -cyclo-C$_3$H$_5$; or $R^9$ and $R^{10}$, or $R^{10}$ and $R^{11}$ form together

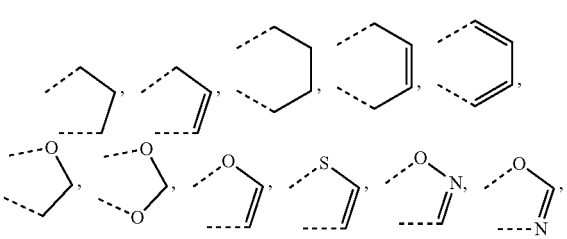

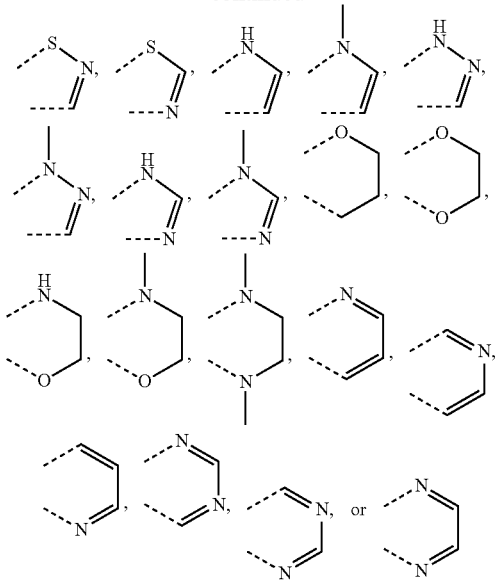

wherein these residues can be substituted with 1 to 3 substituents selected from $Z^7$, $Z^8$, $Z^9$;

or an enantiomer, a diastereomer, a tautomer, a hydrate, a solvate, a prodrug, or a pharmaceutically acceptable salt thereof.

The substituents $R^9$, $R^{10}$, $R^{11}$ can be present on any of the rings of the bicyclic indole moiety or the bicyclic benzopiperidine moiety defined for substituent B and are not limited to the ring connection as shown in general formula

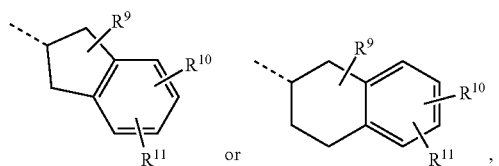

wherein $R^{10}$ and $R^{11}$ are attached to the aromatic benzo ring and $R^9$ is attached to the non-aromatic carbocycle.

The term "$C_3$-$C_{12}$ mono-, bi-, tri-, tetra-, or pentacycloalkyl" as used herein refers to the following residues:

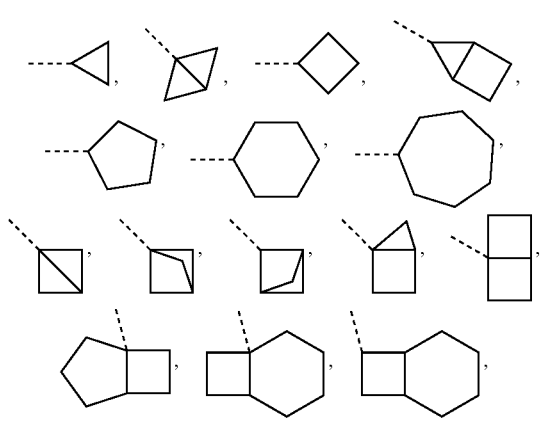

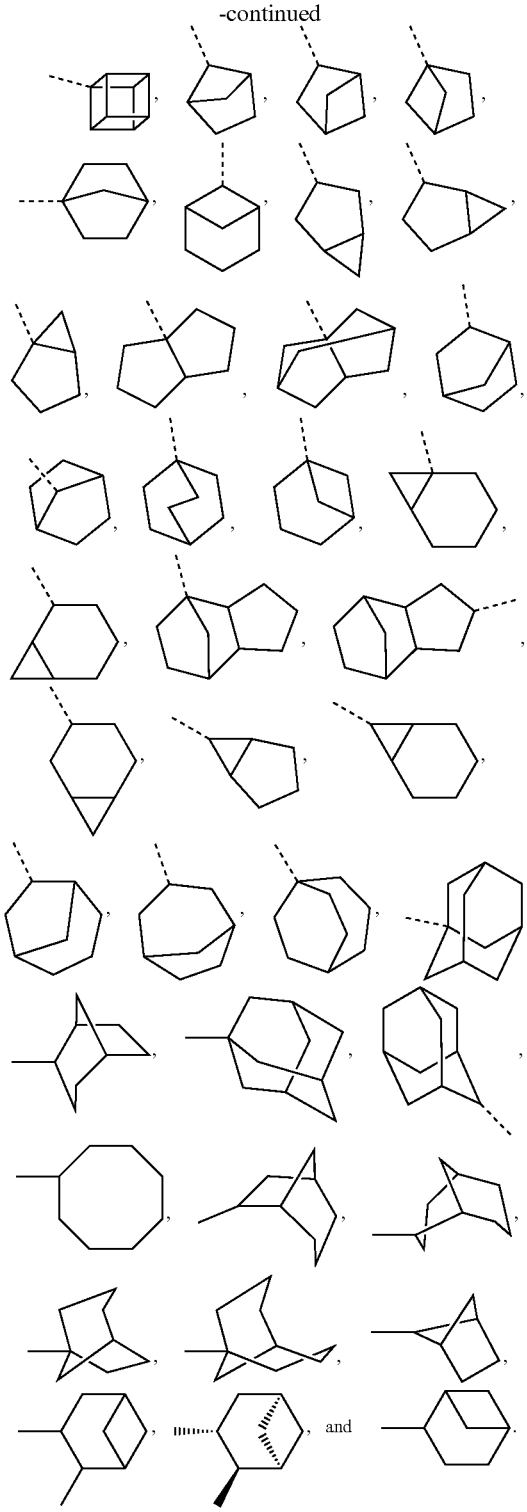

The term "$C_3$-$C_7$-alkyl" as used herein refers to the following residues:

—$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_7H_{15}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—

C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H4-C(CH₃)₃, —CH₂—CH(C₂H₅)₂, and —CH(CH₃)—C(CH₃)₃. The term "C1-C7-alkyl" as used herein refers to —CH₃, —C₂H₅, and C₃-C₇-alkyl.

The term "C3-C6-cycloalkyl" as used herein refers to the following residues:

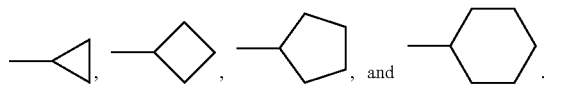

Prodrugs of the compounds related to formula (I) are also within the scope of this invention. These derivatives may have little or no pharmacological activity themselves. The term "prodrug" as used herein describes a precursor of the active ingredient according to general formula (I), wherein said precursor comprises groups which can be cleaved under physiological conditions so that the active agent of formula (I) is formed. Information on the use of prodrugs may be found for example in "Pro-drugs as Novel Drug Delivery Systems" by T. Higuchi and W. Stella, ACS Symposium Series Vol. 14, 1975 (ISBN13: 9780841202917).

A person skilled in the art can synthesize prodrugs for example by replacing a functional group in the compounds according to formula (I) with certain moieties. Examples for prodrugs of a compound according to formula (I) containing a primary or secondary amino functionality include but are not limited to moieties like amides, carbamates or alkyl derivatives thereof. More information on the use of prodrugs for amines may be found for example in *Molecules* 2008, 13, 519-547 (A. L. Simplício et al.) or "Prodrugs of Amines" by J. P. Krise and R. Oliyai (Biotechnology: Pharmaceutical Aspects, 2007, Volume V, Part III, 801-831).

The expression tautomer is defined as an organic compound that is interconvertible by a chemical reaction called tautomerization. Tautomerization can be catalyzed preferably by bases or acids or other suitable compounds.

Preferred, is the compound of any of the formulae (I-1)-(I-4)

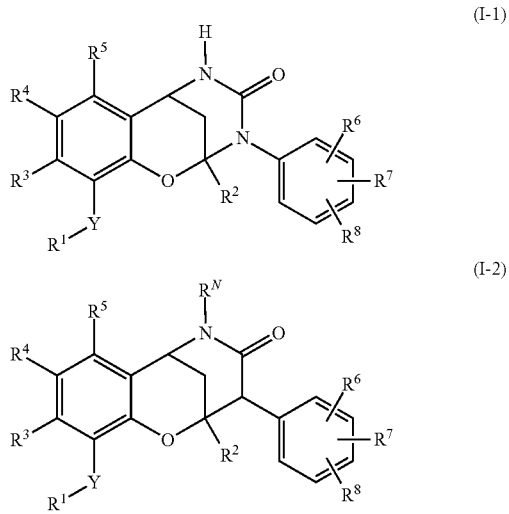

(I-1)

(I-2)

(I-3)

(I-4)

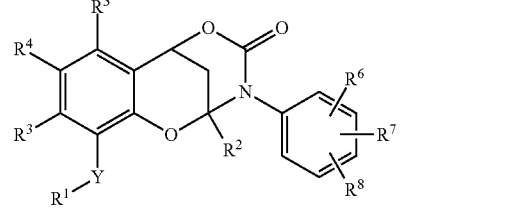

and $R^1$, $R^2$, $R^3$, $R^4$, $R^5$, $R^6$, $R^7$, $R^8$, $R^N$ and Y have the same meanings as defined in the formula (I) or as defined herein.

More preferred are the compounds of general formula (IV)

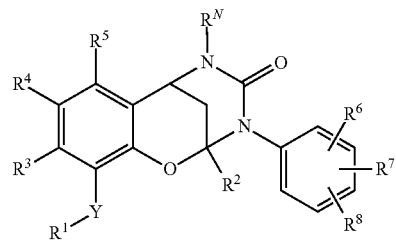

wherein $R^1$-$R^8$ and Y have the meanings as defined in the formula (I) or as defined herein.

Still more preferred are compounds of any one of formulae (I), (II), (IV), (VI), (I-1), (I-2), (I-3) and (I-4), wherein B presents

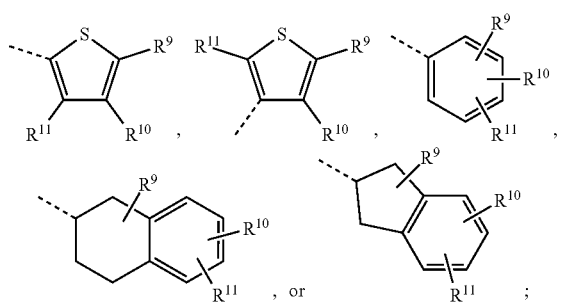

, or                ;

and more preferably wherein B presents

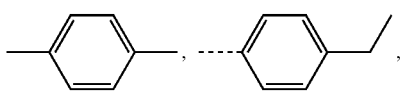

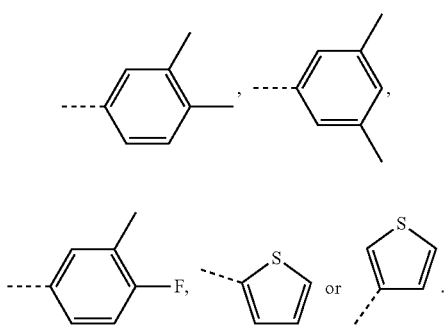

Also preferred are the compounds of general formula (II)

(II)

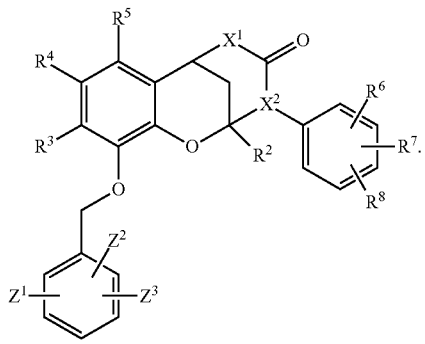

wherein $R^2$-$R^8$, $X^1$, $X^2$ and $Z^1$-$Z^3$ have the meanings as defined in the formula (I) or as defined herein.

Also preferred are the compounds of general formula (III)

(III)

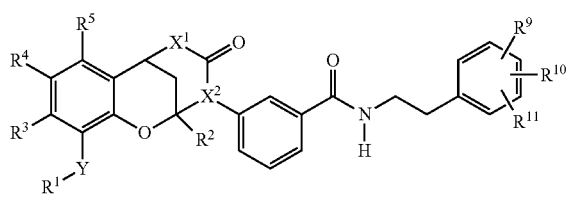

wherein $R^1$-$R^5$, $R^9$-$R^{11}$, $X^1$, $X^2$ and Y have the meanings as defined in the formula (I) or as defined herein.

Also preferred are the compounds of any of general formulae (V), (Va), (Vb), and (Vc)

(V)

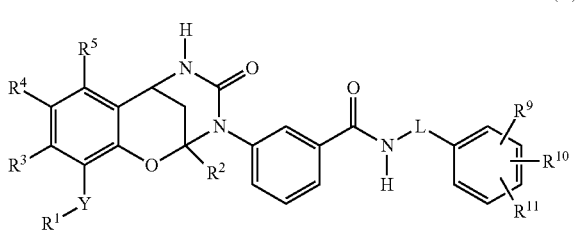

(Va)

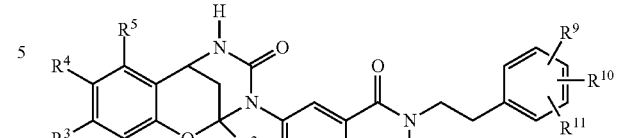

(Vb)

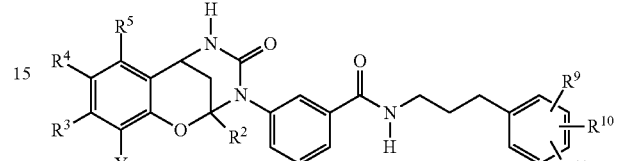

(Vc)

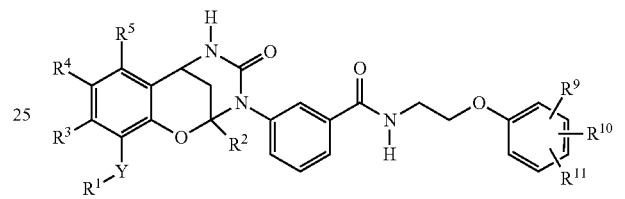

wherein $R^1$-$R^5$, $R^9$-$R^{11}$ and Y have the meanings as defined in the formula (I) or as defined herein and L represents —CH$_2$—CH$_2$—, —CH$_2$—CH$_2$—CH$_2$—, or —CH$_2$—CH$_2$—O—.

Also preferred are the compounds of general formula (VI)

(VI)

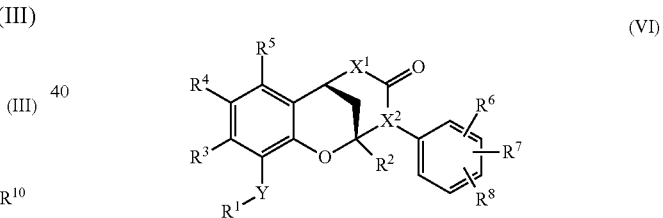

wherein $R^1$-$R^8$, $X^1$, $X^2$ and Y have the meanings as defined in the formula (I) or as defined herein.

Still more preferred are compounds of any one of formulae (I), (III-1), (III-4), (IV-1), (IV-2), (V), (Va), (Vb), (Vc), (VI-1), (VI-2), (I-1), (I-2), (I-3) and (I-4), wherein $R^1$ represents

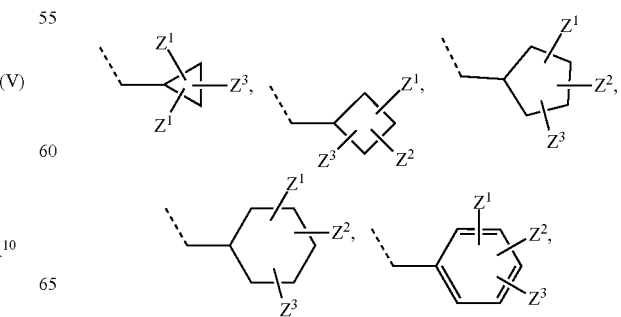

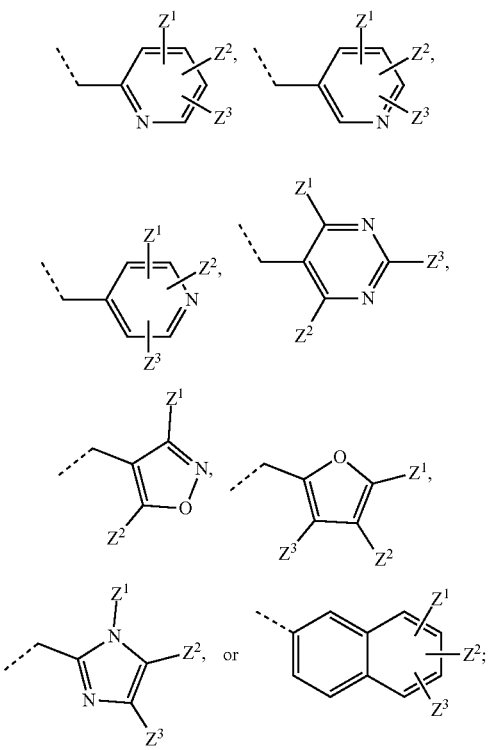
wherein $Z^1$, $Z^2$ and $Z^3$ have the meanings as defined in the formula (I) or as defined herein.
Also preferred are the compounds of any of the formulae (II-1)-(II-6)
(II-1)
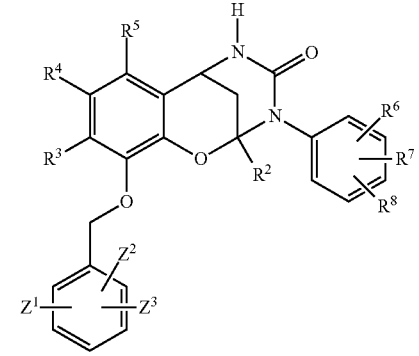
(II-2)
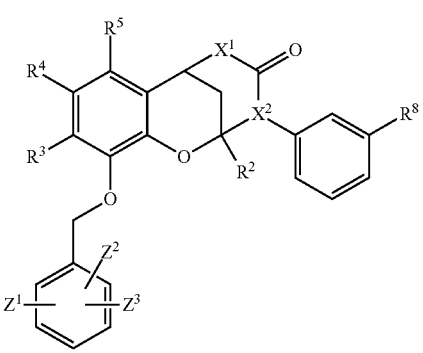
(II-3)
(II-4)
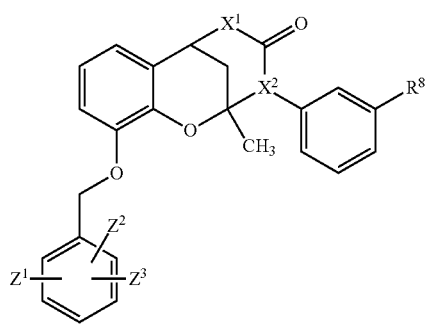
(II-5)
(II-6)
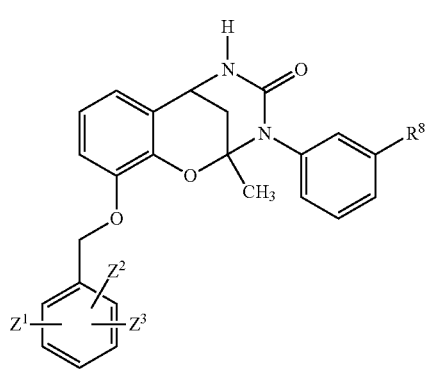
and $R^2$, $R^3$, $R^4$, $R^5$, $R^6$, $R^7$, $R^8$, $X^1$, $X^2$, and $Z^1$-$Z^3$ have the same meanings as defined in the formula (I) or as defined herein.
Also preferred are the compounds of any of the formulae (III-1)-(III-6)

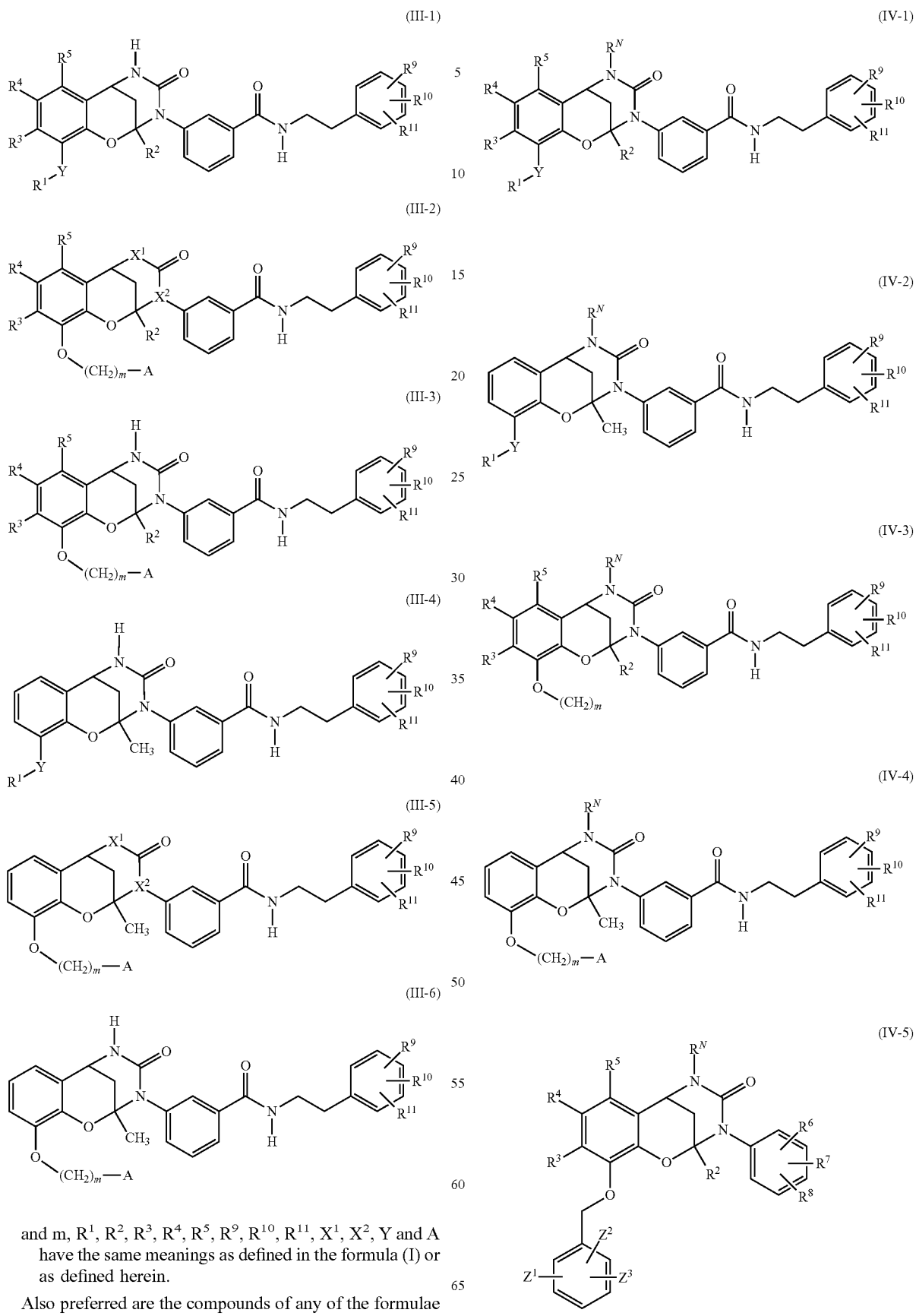
and m, $R^1$, $R^2$, $R^3$, $R^4$, $R^5$, $R^9$, $R^{10}$, $R^{11}$, $X^1$, $X^2$, Y and A have the same meanings as defined in the formula (I) or as defined herein.
Also preferred are the compounds of any of the formulae (IV-1)-(IV-10)

(IV-6)

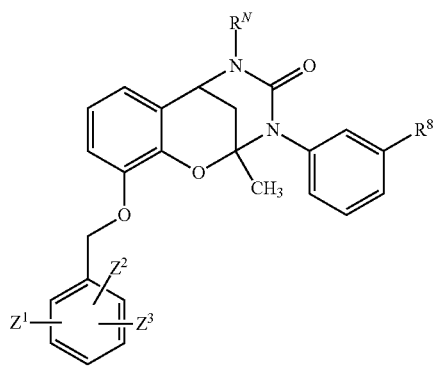

(IV-7)

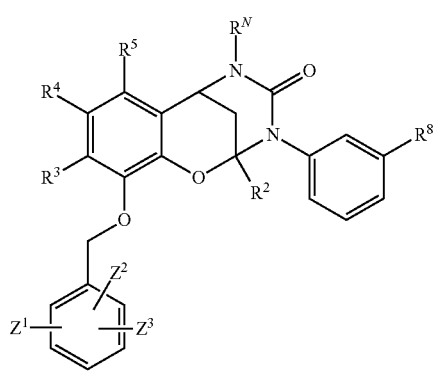

(IV-8)

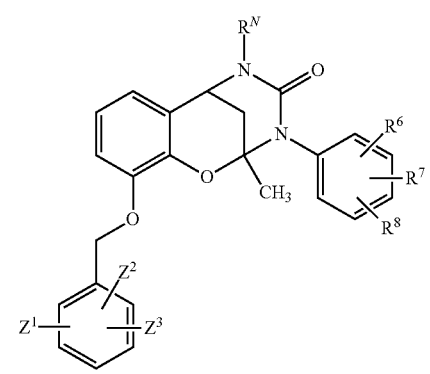

(IV-9)

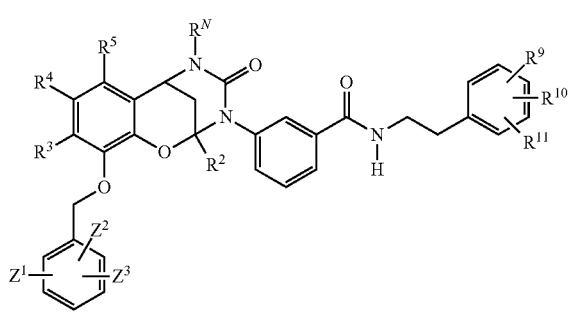

(IV-10)

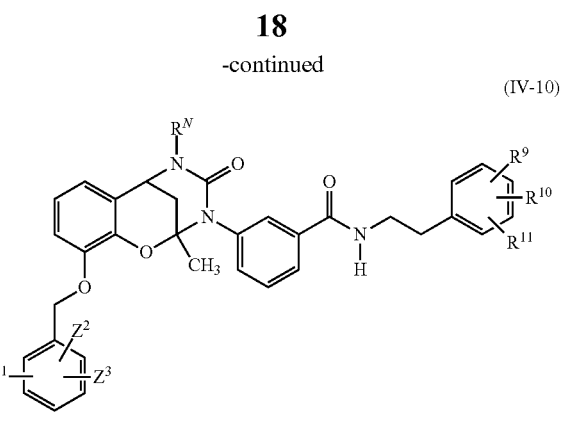

and m, A, R¹, R², R³, R⁴, R⁵, R⁶, R⁷, R⁸, R⁹, R¹⁰, R¹¹, $R^N$, Y and Z¹-Z³ have the same meanings as defined in the formula (I) or as defined herein.

Also preferred are the compounds of any of the formulae (V-1) and (V-2)

(V-1)

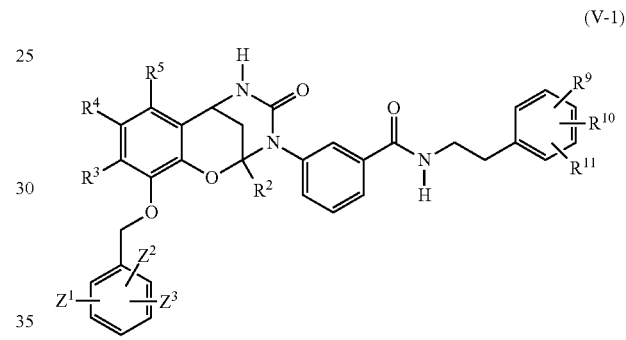

(V-2)

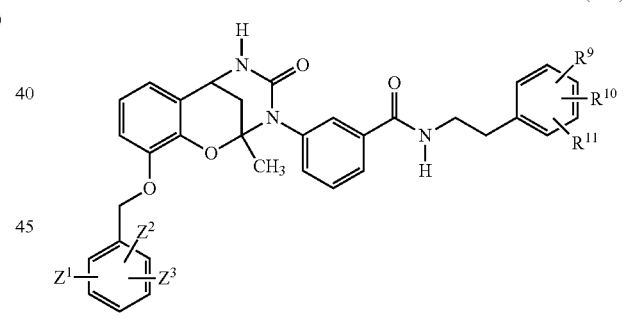

and R², R³, R⁴, R⁵, R⁹, R¹⁰, R¹¹ and Z¹-Z³ have the same meanings as defined in the formula (I) or as defined herein.

Further preferred are the compounds of any of the formulae (VI-1)-(VI-16)

(VI-1)

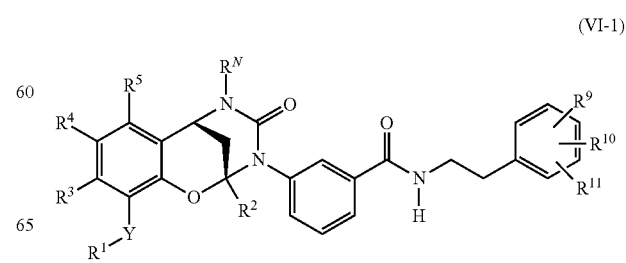

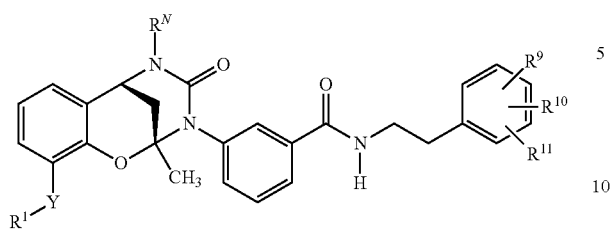
(VI-2)
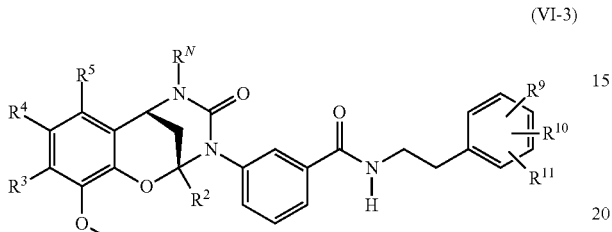
(VI-3)
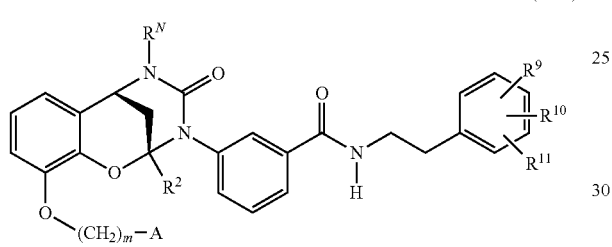
(VI-4)
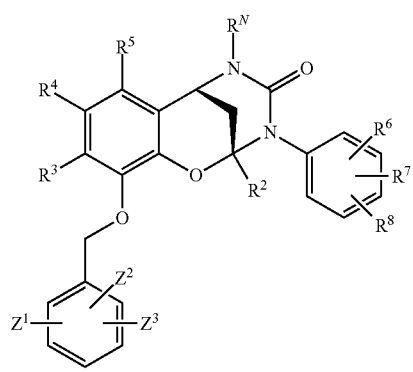
(VI-5)
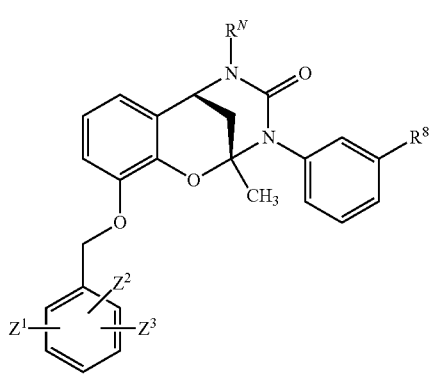
(VI-6)
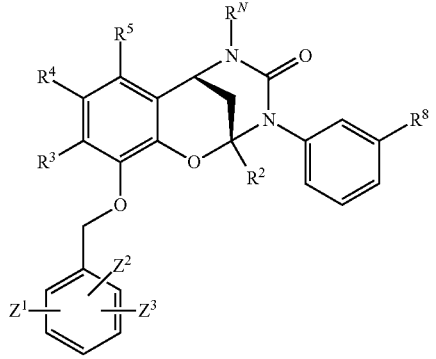
(VI-7)
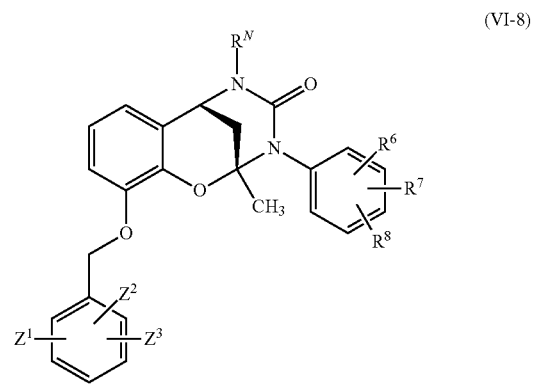
(VI-8)
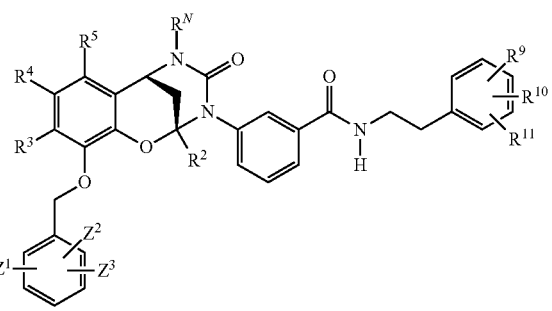
(VI-9)
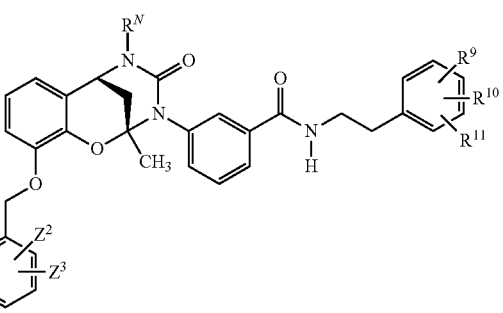
(VI-10)

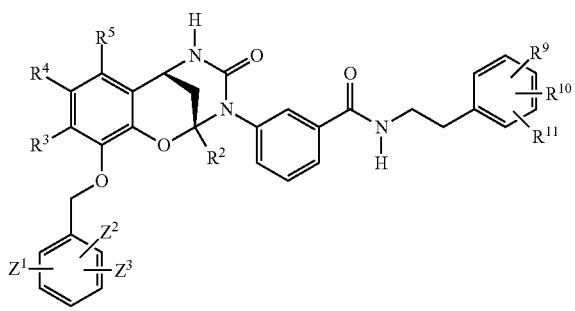
(VI-11)

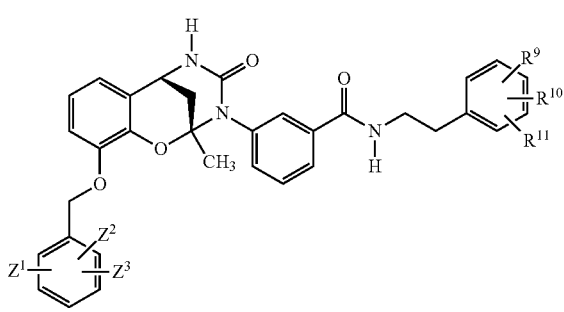
(VI-12)

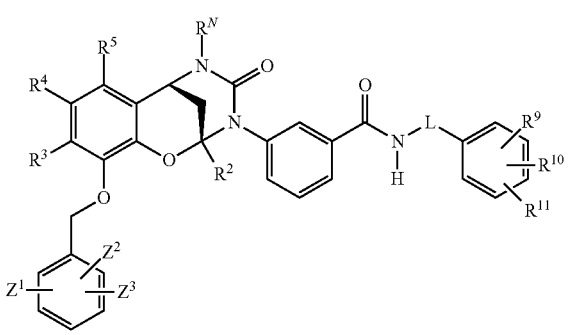
(VI-13)

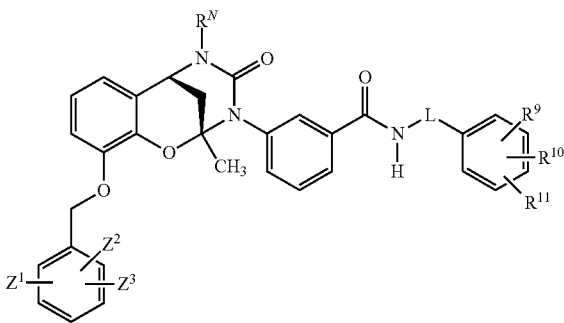
(VI-14)

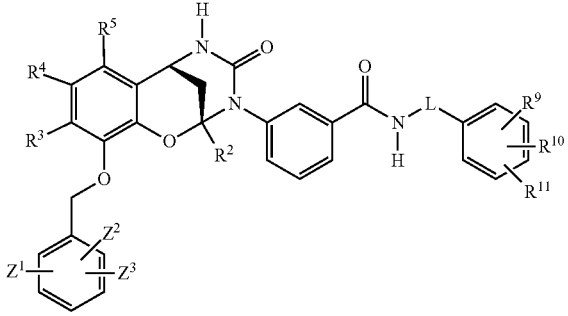
(VI-15)

(VI-16)

and m, A, $R^1$, $R^2$, $R^3$, $R^4$, $R^5$, $R^6$, $R^7$, $R^8$, $R^9$, $R^{10}$, $R^{11}$, $R^N$, Y and $Z^1$-$Z^3$ have the same meanings as defined in the formula (I) or as defined herein and L represents —$CH_2$—$CH_2$—, —$CH_2$—$CH_2$—$CH_2$—, or —$CH_2$—$CH_2$—O—.

Further preferred are the compounds of general formulae (VII) and (VIII)

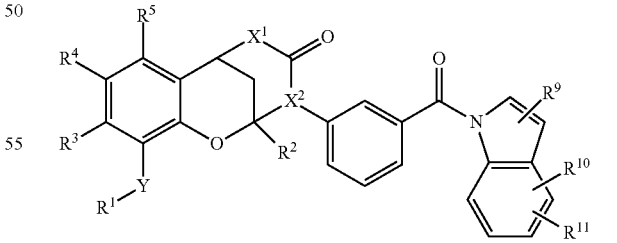
(VII)

(VIII)

wherein $R^1$, $R^2$, $R^3$, $R^4$, $R^5$, $R^9$, $R^{10}$, $R^{11}$, $X^1$, $X^2$ and Y have the same meanings as defined in the formula (I) or as defined herein. The substituents $R^9$, $R^{10}$, $R^{11}$ can be present on any of the rings of the bicyclic indole moiety or the bicyclic benzopiperidine moiety and are not limited to the ring connection as shown in general formulae (VII) and (VIII).

Most referred, R³ is selected from the group consisting of:

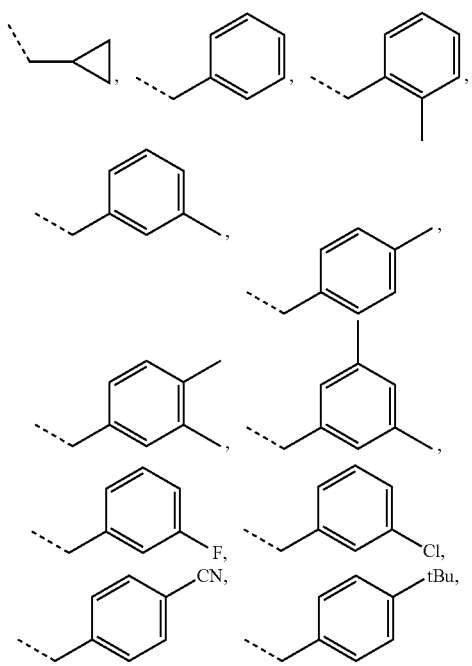

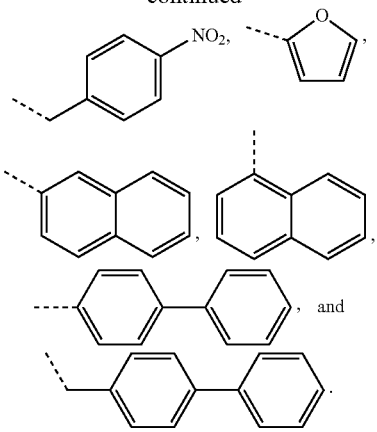

, and

In a further aspect of the present invention, the novel compounds according to the general formula (I) represent chiral compounds. The novel compounds according to the general formula (I) represent a racemate, or a S or a R enantiomer or a mixture of isomers.

In yet another preferred embodiment of the present invention, the compound according to the general formula (I) is selected from the group of compounds depicted in the following Table 1.

TABLE 1

| Compound | Name |
|---|---|
| A01 | 3-(10-(Benzyloxy)-2-methyl-4-oxo-5,6-dihydro-2H-2,6-methanobenzo[g][1,3,5]oxadiazocin-3(4H)-yl)-N-(4-methylphenethyl)benzamide, |
| A02 | 3-(2-Methyl-10-((2-methylbenzyl)oxy)-4-oxo-5,6-dihydro-2H-2,6-methanobenzo[g][1,3,5]oxadiazocin-3(4H)-yl)-N-(4-methylphenethyl)benzamide, |
| A03 | 3-(2-Methyl-10-((4-nitrobenzyl)oxy)-4-oxo-5,6-dihydro-2H-2,6-methanobenzo[g][1,3,5]oxadiazocin-3(4H)-yl)-N-(4-methylphenethyl)benzamide, |

TABLE 1-continued

A04  3-(10-((3-Chlorobenzyl)oxy)-2-methyl-4-oxo-5,6-dihydro-2H-2,6-methanobenzo[g][1,3,5]oxadiazocin-3(4H)-yl)-N-(4-methylphenethyl)benzamide,

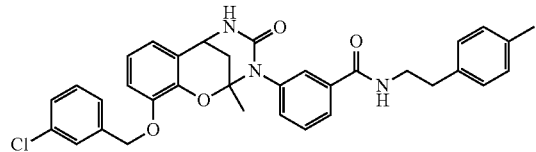 [SMILES: Cc1ccc(CCNC(=O)c2cccc(N3C(=O)NC4CC3(C)Oc3c(OCc5cccc(Cl)c5)cccc34)c2)cc1]

A05  3-(10-((4-Cyanobenzyl)oxy)-2-methyl-4-oxo-5,6-dihydro-2H-2,6-methanobenzo[g][1,3,5]oxadiazocin-3(4H)-yl)-N-(4-methylphenethyl)benzamide,

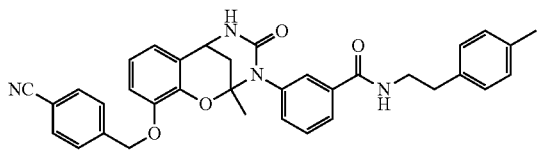 [SMILES: Cc1ccc(CCNC(=O)c2cccc(N3C(=O)NC4CC3(C)Oc3c(OCc5ccc(C#N)cc5)cccc34)c2)cc1]

A06  3-(10-((4-(tert-Butyl)benzyl)oxy)-2-methyl-4-oxo-5,6-dihydro-2H-2,6-methanobenzo[g][1,3,5]oxadiazocin-3(4H)-yl)-N-(4-methylphenethyl)benzamide,

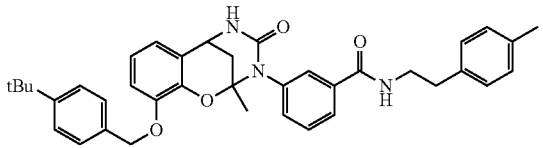 [SMILES: Cc1ccc(CCNC(=O)c2cccc(N3C(=O)NC4CC3(C)Oc3c(OCc5ccc(C(C)(C)C)cc5)cccc34)c2)cc1]

A07  3-(10-(Furan-2-ylmethoxy)-2-methyl-4-oxo-5,6-dihydro-2H-2,6-methanobenzo[g][1,3,5]oxadiazocin-3(4H)-yl)-N-(4-methylphenethyl)benzamide,

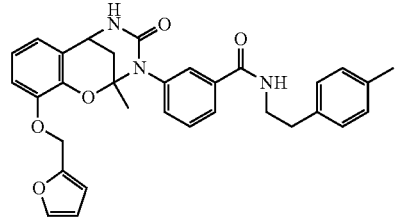 [SMILES: Cc1ccc(CCNC(=O)c2cccc(N3C(=O)NC4CC3(C)Oc3c(OCc5ccco5)cccc34)c2)cc1]

A08  3-(10-(Cyclopropylmethoxy)-2-methyl-4-oxo-5,6-dihydro-2H-2,6-methanobenzo[g][1,3,5]oxadiazocin-3(4H)-yl)-N-(4-methylphenethyl)benzamide,

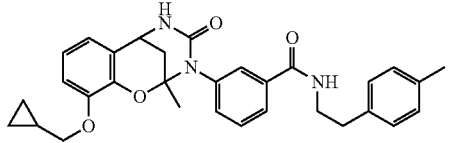 [SMILES: Cc1ccc(CCNC(=O)c2cccc(N3C(=O)NC4CC3(C)Oc3c(OCC5CC5)cccc34)c2)cc1]

A09  3-(2-Methyl-4-oxo-10-(pyridin-4-ylmethoxy)-5,6-dihydro-2H-2,6-methanobenzo[g][1,3,5]oxadiazocin-3(4H)-yl)-N-(4-methylphenethyl)benzamide,

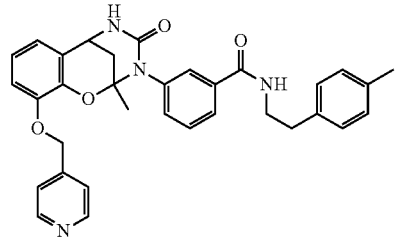 [SMILES: Cc1ccc(CCNC(=O)c2cccc(N3C(=O)NC4CC3(C)Oc3c(OCc5ccncc5)cccc34)c2)cc1]

TABLE 1-continued

A10  3-(2-Methyl-4-oxo-10-(pyridin-3-ylmethoxy)-5,6-dihydro-2H-2,6-
methanobenzo[g][1,3,5]oxadiazocin-3(4H)-yl)-N-(4-
methylphenethyl)benzamide,

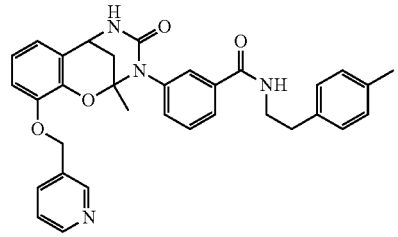 [SMILES: Cc1ccc(CCNC(=O)c2cccc(N3C(=O)NC4CC3(C)Oc3c(OCc5cccnc5)cccc34)c2)cc1]

A11  3-(2-Methyl-4-oxo-10-(pyridin-2-ylmethoxy)-5,6-dihydro-2H-2,6-
methanobenzo[g][1,3,5]oxadiazocin-3(4H)-yl)-N-(4-
methylphenethyl)benzamide,

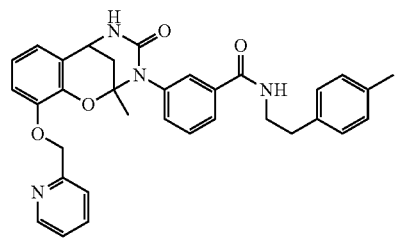 [SMILES: Cc1ccc(CCNC(=O)c2cccc(N3C(=O)NC4CC3(C)Oc3c(OCc5ccccn5)cccc34)c2)cc1]

A12  3-(10-((2-Aminopyridin-3-yl)methoxy)-2-methyl-4-oxo-5,6-dihydro-2H-2,6-
methanobenzo[g][1,3,5]oxadiazocin-3(4H)-yl)-N-(4-
methylphenethyl)benzamide,

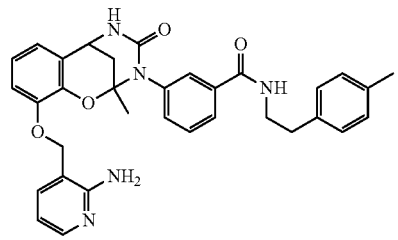 [SMILES: Cc1ccc(CCNC(=O)c2cccc(N3C(=O)NC4CC3(C)Oc3c(OCc5cccnc5N)cccc34)c2)cc1]

A13  3-(2-Methyl-4-oxo-10-(pyrimidin-5-ylmethoxy)-5,6-dihydro-2H-2,6-
methanobenzo[g][1,3,5]oxadiazocin-3(4H)-yl)-N-(4-
methylphenethyl)benzamide,

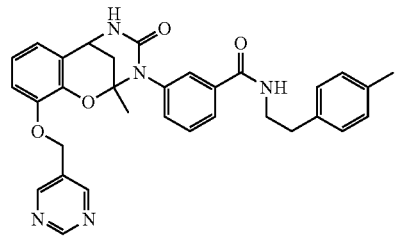

A14  3-(2-Methyl-10-((5-methylpyridin-3-yl)methoxy)-4-oxo-5,6-dihydro-2H-2,6-
methanobenzo[g][1,3,5]oxadiazocin-3(4H)-yl)-N-(4-
methylphenethyl)benzamide,

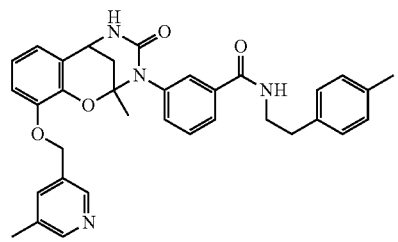

TABLE 1-continued

A15  3-(10-((3,5-Dimethylisoxazol-4-yl)methoxy)-2-methyl-4-oxo-5,6-dihydro-2H-2,6-methanobenzo[g][1,3,5]oxadiazocin-3(4H)-yl)-N-(4-methylphenethyl)benzamide, A16  3-(2-Methyl-10-((1-methyl-1H-imidazol-2-yl)methoxy)-4-oxo-5,6-dihydro-2H-2,6-methanobenzo[g][1,3,5]oxadiazocin-3(4H)-yl)-N-(4-methylphenethyl)benzamide,

| Structure | Synthesis | Compound No. | Exact mass | [M + H]+ found | Name |
|---|---|---|---|---|---|
| | By General Procedure F, using the acid 2-6 and indole. | A17 | 529.20 | 530.3 | 3-(3-(1H-indole-1-carbonyl)phenyl)-10-(benzyloxy)-2-methyl-5,6-dihydro-2H-2,6-methanobenzo[g][1,3,5]oxadiazocin-4(3H)-one |
| | By General Procedure F, using the acid 2-6 and 1,2,3,4-tetrahydroisoquinoline. | A18 | 545.23 | 546.4 | 10-(benzyloxy)-2-methyl-3-(3-(1,2,3,4-tetrahydroisoquinoline-2-carbonyl)phenyl)-5,6-dihydro-2H-2,6-methanobenzo[g][1,3,5]oxadiazocin-4(3H)-one |
| | By General Procedure F, using the acid 2-6 and indoline. | A19 | 531.22 | 532.4 | 10-(benzyloxy)-3-(3-(indoline-1-carbonyl)phenyl)-2-methyl-5,6-dihydro-2H-2,6-methanobenzo[g][1,3,5]oxadiazocin-4(3H)-one |
| | By General Procedure F, using the acid 2-6 and N-methyl-2-phenoxyethanamine. | A20 | 563.24 | 564.3 | 3-(10-(benzyloxy)-2-methyl-4-oxo-5,6-dihydro-2H-2,6-methanobenzo[g][1,3,5]oxadiazocin-3(4H)-yl)-N-methyl-N-(2-phenoxyethyl)benzamide |
| | By General Procedure F, using the acid 2-6 and 2-phenoxyethanamine. | A21 | 549.23 | 550.3 | 3-(10-(benzyloxy)-2-methyl-4-oxo-5,6-dihydro-2H-2,6-methanobenzo[g][1,3,5]oxadiazocin-3(4H)-yl)-N-(2-phenoxyethyl)benzamide |

TABLE 1-continued

| Structure | Procedure | # | MW | MS | Name |
|---|---|---|---|---|---|
| 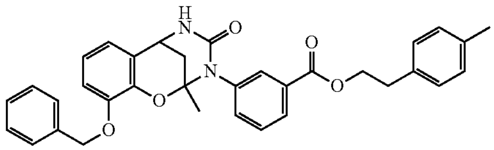 [SMILES: Cc1ccc(CCOC(=O)c2cccc(N3C(=O)NC4CC3(C)Oc3c(OCc5ccccc5)cccc34)c2)cc1] | By General Procedure F, using the acid 2-6 and 2-(p-tolyl)-ethanol. | A22 | 548.23 | 549.3 | 4-methylphenethyl 3-(10-(benzyloxy)-2-methyl-4-oxo-5,6-dihydro-2H-2,6-methanobenzo[g][1,3,5]oxadiazocin-3(4H)-yl)benzoate |
| 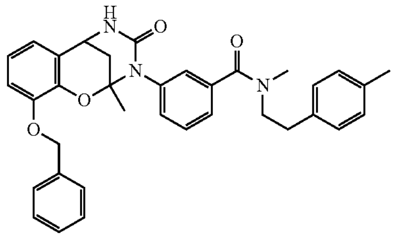 [SMILES: Cc1ccc(CCN(C)C(=O)c2cccc(N3C(=O)NC4CC3(C)Oc3c(OCc5ccccc5)cccc34)c2)cc1] | By General Procedure F, using the acid 2-6 and N-methyl-2-(p-tolyl)-ethanamine. | A23 | 561.26 | 562.4 | 3-(10-(benzyloxy)-2-methyl-4-oxo-5,6-dihydro-2H-2,6-methanobenzo[g][1,3,5]oxadiazocin-3(4H)-yl)-N-methyl-N-(4-methylphenethyl)benzamide |
| 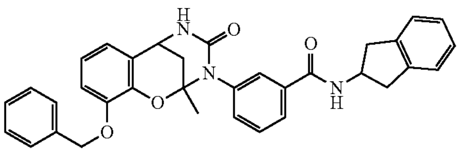 [SMILES: CC12CC(NC(=O)N1c1cccc(C(=O)NC3Cc4ccccc4C3)c1)c1cccc(OCc3ccccc3)c1O2] | By General Procedure F, using the acid 2-6 and 2,3-dihydro-1H-inden-2-amine. | A24 | 545.23 | 546.3 | 3-(10-(benzyloxy)-2-methyl-4-oxo-5,6-dihydro-2H-2,6-methanobenzo[g][1,3,5]oxadiazocin-3(4H)-yl)-N-(2,3-dihydro-1H-inden-2-yl)benzamide |
| 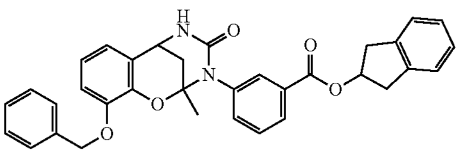 [SMILES: CC12CC(NC(=O)N1c1cccc(C(=O)OC3Cc4ccccc4C3)c1)c1cccc(OCc3ccccc3)c1O2] | By General Procedure F, using the acid 2-6 and 2,3-dihydro-1H-inden-2-ol. | A25 | 546.22 | 547.3 | 2,3-dihydro-1H-inden-2-yl 3-(10-(benzyloxy)-2-methyl-4-oxo-5,6-dihydro-2H-2,6-methanobenzo[g][1,3,5]oxadiazocin-3(4H)-yl)benzoate |
| 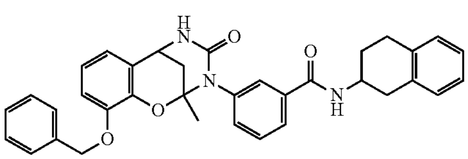 [SMILES: CC12CC(NC(=O)N1c1cccc(C(=O)NC3CCc4ccccc4C3)c1)c1cccc(OCc3ccccc3)c1O2] | By General Procedure F, using the acid 2-6 and 1,2,3,4-tetrahydronaphthalen-2-amine. | A26 | 559.25 | 560.4 | 3-(10-(benzyloxy)-2-methyl-4-oxo-5,6-dihydro-2H-2,6-methanobenzo[g][1,3,5]oxadiazocin-3(4H)-yl)-N-(1,2,3,4-tetrahydronaphthalen-2-yl)benzamide |
| 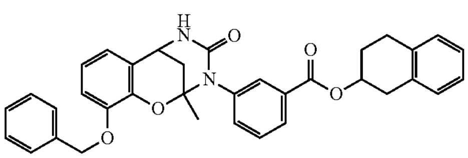 [SMILES: CC12CC(NC(=O)N1c1cccc(C(=O)OC3CCc4ccccc4C3)c1)c1cccc(OCc3ccccc3)c1O2] | By General Procedure F, using the acid 2-6 and 1,2,3,4-tetrahydro-naphthalen-2-ol | A27 | 560.23 | 561.3 | 1,2,3,4-tetrahydronaphthalen-2-yl 3-(10-(benzyloxy)-2-methyl-4-oxo-5,6-dihydro-2H-2,6-methanobenzo[g][1,3,5]oxadiazocin-3(4H)-yl)benzoate |
| | By General Procedure G, using the phenol 2-5 in analogy to example A01. | A28 | 525.26 | 526.4 | 3-(10-(cyclobutylmethoxy)-2-methyl-4-oxo-5,6-dihydro-2H-2,6-methanobenzo[g][1,3,5]oxadiazocin-3(4H)-yl)-N-(4-methylphenethyl)benzamide |
| | By General Procedure G, using the phenol 2-5 in analogy to example A01. | A29 | 539.28 | 540.5 | 3-(10-(cyclopentylmethoxy)-2-methyl-4-oxo-5,6-dihydro-2H-2,6-methanobenzo[g][1,3,5]oxadiazocin-3(4H)-yl)-N-(4-methylphenethyl)benzamide |
| | By General Procedure G, using the phenol 2-5 in analogy to example A01. | A30 | 553.29 | 554.5 | 3-(10-(cyclohexylmethoxy)-2-methyl-4-oxo-5,6-dihydro-2H-2,6-methanobenzo[g][1,3,5]oxadiazocin-3(4H)-yl)-N-(4-methylphenethyl)benzamide |

TABLE 1-continued

| Structure | Procedure | ID | MW | MS | Name |
|---|---|---|---|---|---|
|  | By General Procedure G, using the phenol 2-5 in analogy to example A01. | A31 | 565.29 | 566.4 | 3-(10-(bicyclo[2.2.1]heptan-1-yl-methoxy)-2-methyl-4-oxo-5,6-dihydro-2H-2,6-methanobenzo[g]-[1,3,5]oxadiazocin-3(4H)-yl)-N-(4-methylphenethyl)benzamide |
| 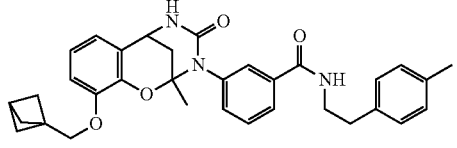 [SMILES: Cc1ccc(CCNC(=O)c2cccc(N3C(=O)NC4CC3(C)Oc3c(OCC56CC(C5)C6)cccc34)c2)cc1] | By General Procedure G, using the phenol 2-5 in analogy to example A01. | A32 | 537.26 | 538.3 | 3-(10-(bicyclo[1.1.1]pentan-1-yl-methoxy)-2-methyl-4-oxo-5,6-dihydro-2H-2,6-methanobenzo[g]-[1,3,5]oxadiazocin-3(4H)-yl)-N-(4-methylphenethyl)benzamide |
| 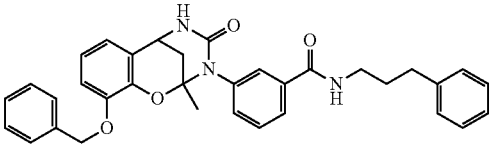 | By General Procedure F, using the acid 2-6 and 3-phenyl-1-propylamine. | A33 | 547.65 | 548.7 | 3-(10-(benzyloxy)-2-methyl-4-oxo-5,6-dihydro-2H-2,6-methanobenzo[g][1,3,5]oxadiazocin-3(4H)-yl)-N-(3-phenylpropyl)benzamide |
| 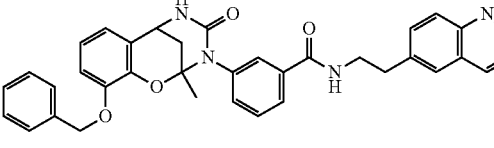 | By General Procedure F, using the acid 2-6 and 1-quinolin-6-yl-ethylamine. | A34 | 584.68 | 585.8 | 3-(10-(benzyloxy)-2-methyl-4-oxo-5,6-dihydro-2H-2,6-methanobenzo[g][1,3,5]oxadiazocin-3(4H)-yl)-N-(1-quinolin-6-yl-ethyl)benzamide |
| 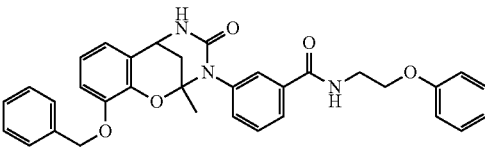 | By General Procedure F, using the acid 2-6 and 2-(4-methylphenoxy)ethanamine. | A35 | 563.65 | 564.8 | 3-(10-(benzyloxy)-2-methyl-4-oxo-5,6-dihydro-2H-2,6-methanobenzo[g][1,3,5]oxadiazocin-3(4H)-yl)-N-(2-(4-methylphenoxy)ethyl)benzamide |
| 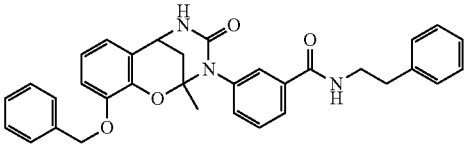 [SMILES: CC12CC(NC(=O)N1c1cccc(C(=O)NCCc3ccccc3)c1)c1cccc(OCc3ccccc3)c1O2] | By General Procedure F, using the acid 2-6 and homobenzyl amine. | A36 | 533.63 | 534.8 | 3-(10-(benzyloxy)-2-methyl-4-oxo-5,6-dihydro-2H-2,6-methanobenzo[g][1,3,5]oxadiazocin-3(4H)-yl)-N-(phenethyl)benzamide |
| 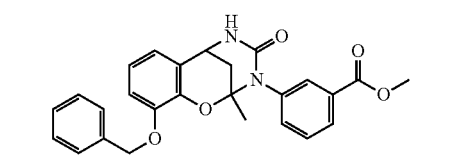 [SMILES: COC(=O)c1cccc(N2C(=O)NC3CC2(C)Oc2c(OCc4ccccc4)cccc23)c1] | By General Procedure F, using the acid 2-6 and methanol. | A37 | 444.49 | 445.6 | methyl 3-(10-(benzyloxy)-2-methyl-4-oxo-5,6-dihydro-2H-2,6-methanobenzo[g][1,3,5]oxadiazocin-3(4H)-yl)benzoate |
| 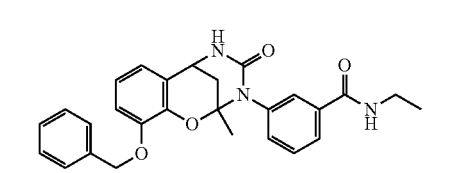 [SMILES: CCNC(=O)c1cccc(N2C(=O)NC3CC2(C)Oc2c(OCc4ccccc4)cccc23)c1] | By General Procedure F, using the acid 2-6 and ethylamine. | A38 | 457.53 | 458.5 | 3-(10-(benzyloxy)-2-methyl-4-oxo-5,6-dihydro-2H-2,6-methanobenzo[g][1,3,5]oxadiazocin-3(4H)-yl)-N-(ethyl)benzamide |

TABLE 1-continued

| | | | | |
|---|---|---|---|---|
| 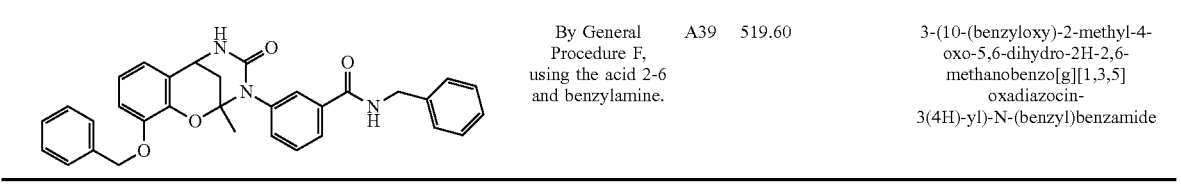 | By General Procedure F, using the acid 2-6 and benzylamine. | A39 | 519.60 | 3-(10-(benzyloxy)-2-methyl-4-oxo-5,6-dihydro-2H-2,6-methanobenzo[g][1,3,5]oxadiazocin-3(4H)-yl)-N-(benzyl)benzamide |

The compounds of the present invention may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, trifluoroacetic acid, and other mineral or carboxylic acids well known to those skilled in the art. The salts are prepared by contacting the free base form with a sufficient amount of the desired acid to produce a salt in the conventional manner.

In the case the inventive compounds bear acidic groups, salts could also be formed with inorganic or organic bases. Examples for suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Synthesis of Compounds

The inventive 1,3,5-benzoxadiazocin-4-one compounds of the present invention can be prepared according to the general synthetic methods as shown in scheme 1.

Three reaction components, i.e. betaketoester (1a), substituted urea (2a), and 2-hydroxybenzaldehyde (3a) can be reacted in one pot system according to step B1 and the product (I) can be obtained in a good yield. Alternatively, an intermediate compound (Ia) can be prepared by three-component reaction of betaketoester (1a), substituted urea (2a), and 2-hydroxybenzaldehyde (3b) in one pot system and said intermediate compound (Ia) can be further reacted with a reagent R3-L (4a) to obtain the product compound (I).

Starting materials betaketoester 1a, urea 2a, benzaldehyde 3a and/or 3b are commercially available or can be synthesized according to or in analogy to literature procedures. Therefore, the synthetic approach according to scheme 1 enables the synthesis of any of the 1,3,5-benzoxadiazocin-4-one compounds disclosed in the present invention.

Scheme 1

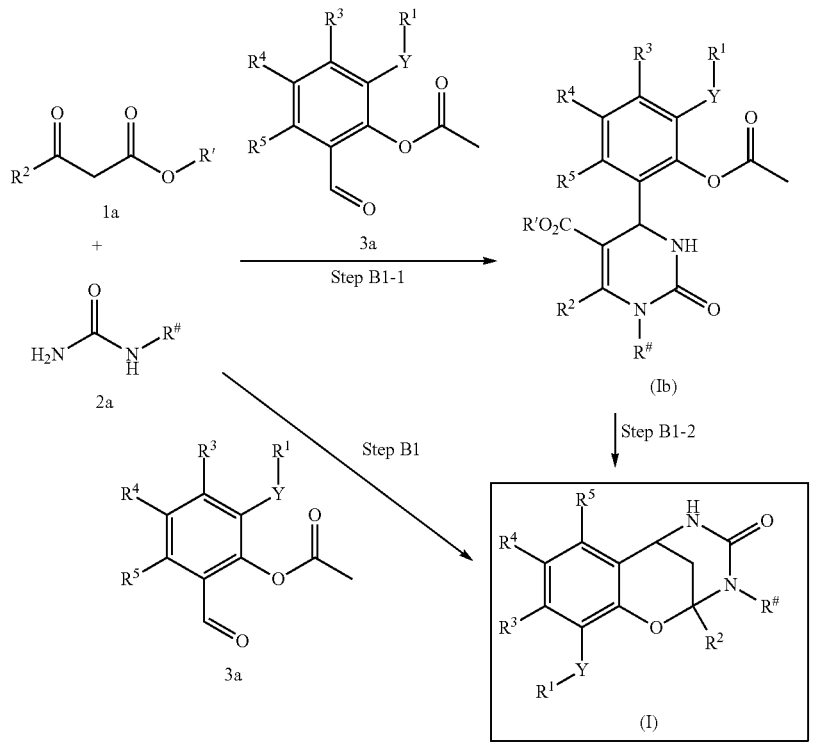

-continued
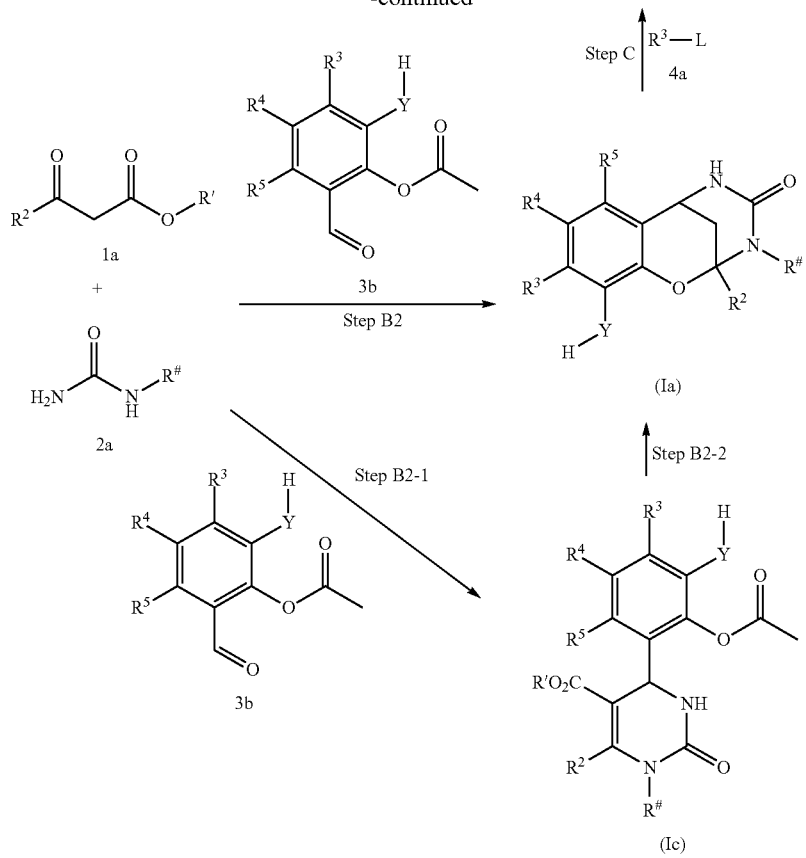
Therefore, a further aspect of the present invention is a method for preparing a compound of the formula (I) comprising:
A) Providing betaketoester (1a) and urea (2a)
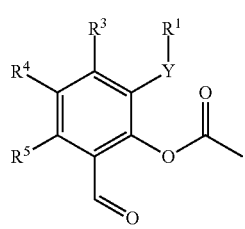
B1) reacting the benzaldehyde (3a) with the betaketoester (1a) and the urea (2a)
to obtain a compound of the formula (1-1):
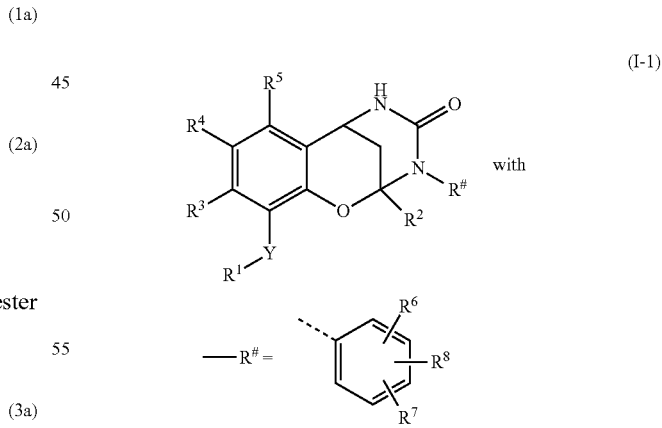
or
B2) reacting the benzaldehyde (3b) with the betaketoester (1a) and the urea (2a)

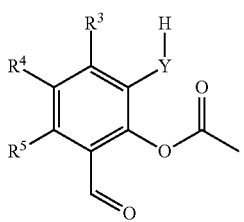
(3b)

to obtain an compound (Ia)

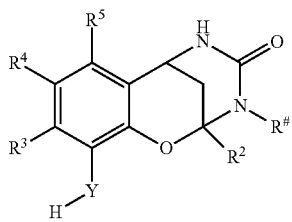
(Ia)

C) reacting a compound R³-L (4a) with the compound (Ia) to obtain a compound of the formula (1-1):

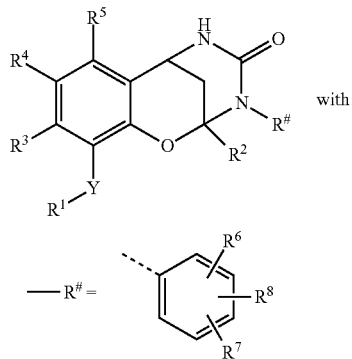
(I-1)

with

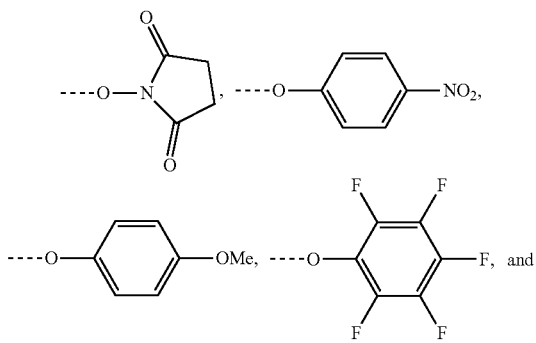

wherein

R' is an activating group selected from a group consisting of: —OCH₃, —OCH₂CH₃, —OCH₂CH₂CH₃, —OCH(CH₃)₂, —OCH₂CH₂CH₂CH₃, —OCH₂CH(CH₃)₂, —OC(CH₃)₃, —OPh, —OCH₂Ph,

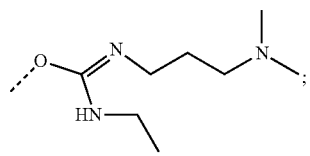

L is a leaving group selected from a group consisting of: —Cl, —Br, —I, —OMs, —OTs, and —OSO₂CF₃;

and R¹, R², R³, R⁴, R⁵, R⁶, X₃, and Y have the same meanings as defined herein.

Preferred, the Step B1) comprises steps B1-1) and B1-2) and these steps B1-1) and B1-2) are performed in one pot system. The Step B1-2) further comprises the following steps B1-2a)-B1-2d) as shown in scheme 2. Therefore, the Step B1) comprises the steps B1-1), B1-2a), B1-2b), B1-2c) and B1-2d). In the step B1), all steps B1-1), B1-2a), B1-2b), B1-2c) and B1-2d) are performed in one pot system as follows:

B1-1) performing three-components reaction of the benzaldehyde (3a) with the betaketoester (1a) and the urea (2a) to obtain an intermediate compound (Ib),

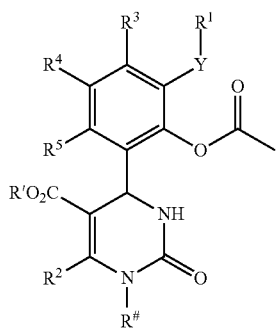
(Ib)

B1-2a) removing acetyl group from —X₃—Ac group of (Ib) to obtain an intermediate compound (Ib-1)

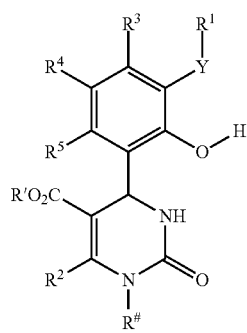
(Ib-1)

B1-2b) performing intramolecular cyclization reaction of the intermediate compound (Ib-1) to obtain an intermediate compound (Ib-2)

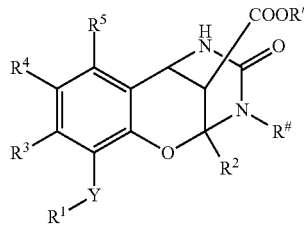

(Ib-2)

B1-2c) removing R' group from CO$_2$R' of (Ib-2) to obtain an intermediate compound (Ib-3)

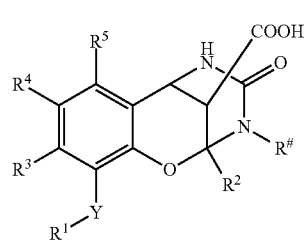

(Ib-3)

B1-2d) removing CO$_2$H group from the intermediate compound (Ib-3) to obtain the compound of formula (I-1)

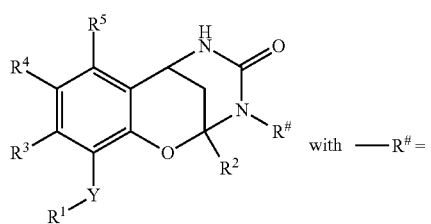

(I-1)

with —R$^\#$ =

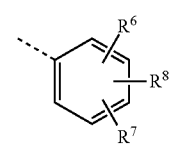

Alternatively, Step B1-1) and B1-2) can be performed separately. In this case, after step B1-1), the intermediate compound (Ib) may be isolated, or optionally further purifying step B1-1a) may be followed to in order to obtain the intermediate compound (Ib): Step B1-1a) purifying the obtained intermediate compound (Ib).

Scheme 2

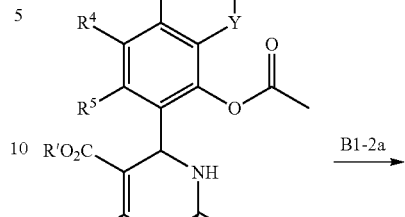

(Ib)

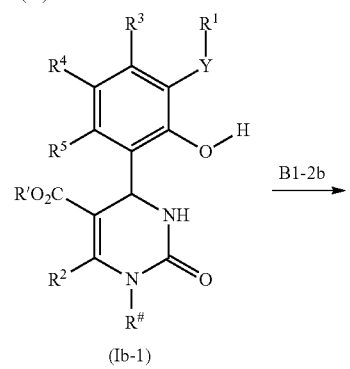

(Ib-1)

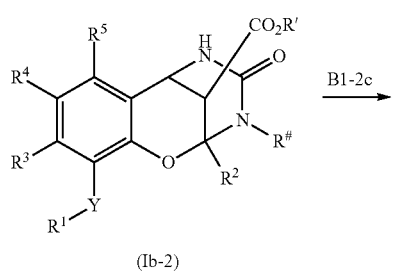

(Ib-2)

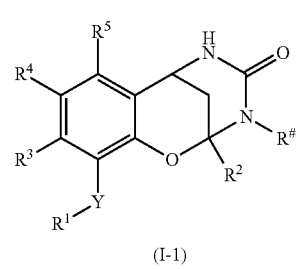

(Ib-3)

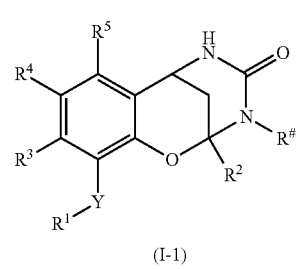

(I-1)

Scheme 3

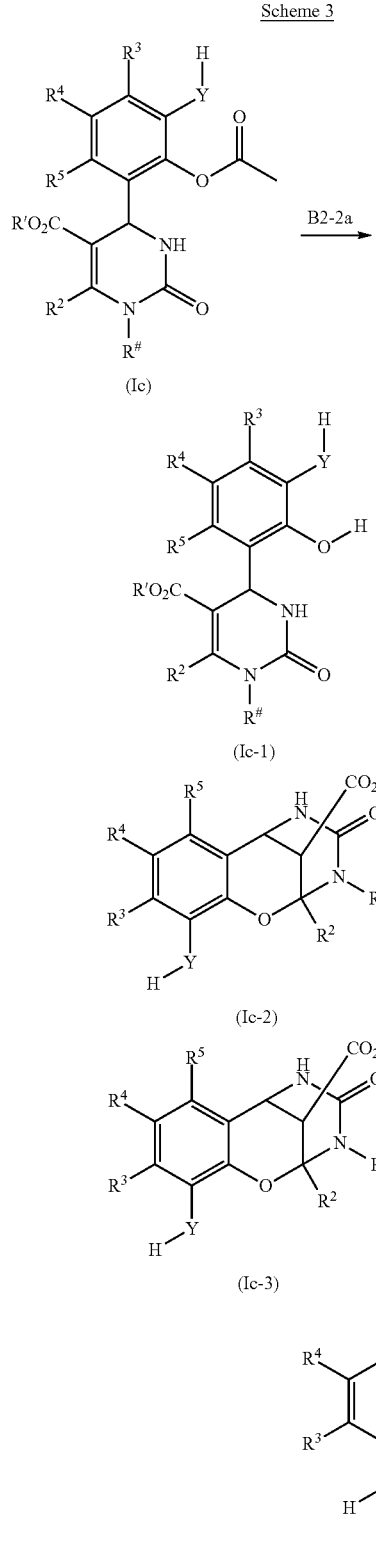

The Step B2) comprises steps B2-1) and B2-2) and these steps B2-1) and B2-2) are performed in one pot system. The Step B2-2) further comprises the following steps B2-2a)-B2-2d) as shown in scheme 3. Therefore, the Step B2) comprises the steps B1-1), B1-2a), B1-2b), B1-2c) and B1-2d). In the step B1), all steps B1-1), B1-2a), B1-2b), B1-2c) and B1-2d) are performed in one pot system as follows:

B2-1) performing three-components reaction of the benzaldehyde (3b) with the betaketoester (1a) and the urea (2a) to obtain an intermediate compound (Ib),

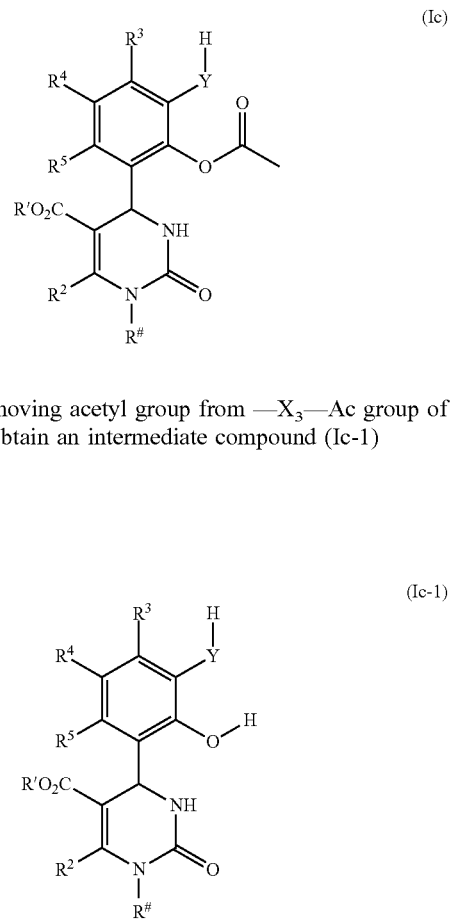

B2-2a) removing acetyl group from —X₃—Ac group of (Ic) to obtain an intermediate compound (Ic-1)

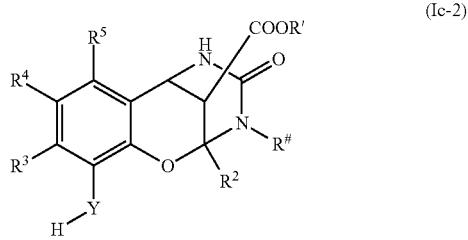

B1-2b) performing intramolecular cyclization reaction of the intermediate compound (Ic-1) to obtain an intermediate compound (Ic-2)

B1-2c) removing R' group from CO₂R' of (Ic-2) to obtain an intermediate compound (Ib-3)

(Ic-3)

B1-2d) removing CO₂H group from the intermediate compound (Ic-3) to obtain the compound of formula (Ia)

(I-1)

with ──R# =

Alternatively, Step B2-1) and B2-2) can be performed separately. In this case, after step B2-1), the intermediate compound (Ic) may be isolated, or optionally further purifying step B2-1a) may be followed to in order to obtain the intermediate compound (Ib): Step B2-1a) purifying the obtained intermediate compound (Ic).

Therefore, the compound of the present invention may be produced by any one of the following combinations of synthetic steps:

Steps A)→B1);
Steps A)→B1-1)→B1-2);
Steps A)→B1-1)→B1-1a)→B1-2);
Steps A)→B1-1)→B1-2a)→B1-2b)→B1-2c)→B1-2d);
Steps A)→B1-1)→B1-1a)→B1-2a)→B1-2b)→B1-2c)→B1-2d);
Steps A)→2)→C);
Steps A)→B2-1)→B2-2)→C);
Steps A)→B2-1)→B2-1a)→B2-2)→C);
Steps A)→B2-1)→B2-2a)→B2-2b)→B2-2c)→B2-2d)→C);
Steps A)→B2-1)→B2-1a)→B2-2a)→B2-2b)→B2-2c)→B2-2d)→C);

The inventive compound may be synthesized through further alternative synthetic method as shown in scheme 4.

Scheme 4

(I-1A)

(I-1)

$$R^{1*} = \quad \begin{array}{cc} X_5 & X_6 \\ CO_2H & NH_2 \\ SO_3H & CO_2H, \\ NH_2 & SO_3H \end{array}$$

The synthetic method of the inventive compound comprises:

A1) Providing betaketoester (1a) and urea (2b)

(1a)

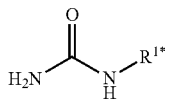

B3) reacting the benzaldehyde (3a) with the betaketoester (1a) and the urea (2a)

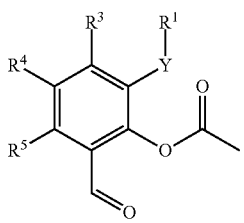

to obtain a compound of the formula (I-4):

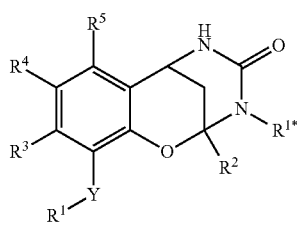

wherein $R^{1*}$ represents

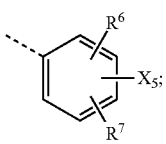

D1) reacting the compound (I-4) with $X_6$—$(CH_2)_n$—B to obtain an compound (I-1)

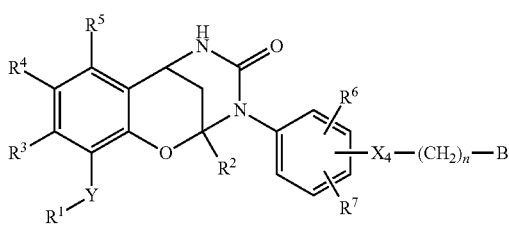

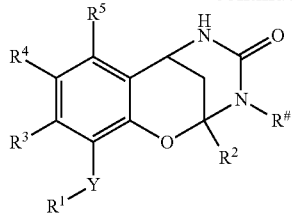

Three component reactions in the steps B1), B1-1), B2), B2-1), B3) are performed in an aprotic polar solvent in the presence of catalysis, especially, chlorotrimethylsilane (TMSCl) at a temperature in a range of 0 to 40° C., preferred 5 to 35° C., more preferred 10 to 30° C., most preferred 15 to 25° C. Preferred, the aprotic polar solvent is DMF.

When the intermediate compound may be isolated, the step B1-1a) or B1-2a) may be performed. In the step B1-2a), or B2-2a) acetyl group is removed by treating with a base in an polar solvent. Preferred, in the step B1-2a), or B2-2a), acetyl group is removed by treating with $NaHCO_3$ in MeOH at a temperature in a range of 30 to 65° C., preferred, 35 to 50° C., more preferred 35-45° C., most preferred 40° C. Under the same condition, the intramolecular cyclization reaction step B1-2b) or B2-2b) is performed.

In the step B1-2c), and B2-2c), the ester group $CO_2R'$ is converted to CO2H by treating with a base in an aqueous solvent at a temperature in a range of 30 to 65° C., preferred, 35 to 50° C., more preferred 35-45° C., most preferred 40° C. Preferred, the base is LiOH or NaOH in a molar ratio of 5 to 30 equivalents, preferred 10 to 20 equivalents, more preferred 13 to 17 equivalents, most preferred 15 equivalents and the aqueous solvent is a mixture of water and THF (1:1).

In the step B1-2d), or B2-2d), $CO_2H$ group is removed by treating with an acid at a temperature in a range of 40 to 100° C., preferred, 50 to 90° C., more preferred 70 to 90° C., most preferred 80 to 85° C. Preferred, the acid is HCl or $H_2SO_4$.

In the step C) the compound $R^3$-L (4a) is coupled with the compound (Ia) in the presence of a base in an aprotic polar solvent, preferred acetonitrile at a temperature of in a range of 50 to 100° C., preferred, 60 to 90° C., more preferred 70 to 90° C., most preferred 80 to 85° C. Preferred, L is Cl, Br, or I and the base is $Na_2CO_3$, or $K_2CO_3$.

In the step D1) the compound (I-4) with $X^6$—$(CH_2)_n$—B is coupled with the intermediate compound (I-4) in the presence of coupling reagent and a base. If the functional group $X_5$ of the compound (I-4) and $X_6$ form an amide bond as $X_4$, any of the known coupling reagents and bases can be used. Preferred coupling reagent is HOSu, DCC, DIC, EDC, BOP, PyAOP, PyBOP, PyBrOP, TBTU, HBTU, HATU, COMU, or TFFH. Preferred, the basis is diisoproylethylamine (DIPEA), DMAP or N-methyl-morpholine (NMM).

If the functional group $X_5$ of the compound (I-4) and $X_6$ form a sulfonamide bond as $X_4$, sulfonic acid (—$SO_3H$) group of $X_5$ or $X_6$ is preferred activated to sulfonyl chloride (—$SO_2Cl$) and coupled with an amine of $X_6$ or $X_5$.

Indications

In another aspect of the present invention, the compounds according to the general formula (I) as well as pharmaceutically acceptable salts thereof are used as an inhibitor for a glucose transporter (GLUT). Said glucose transporter can be selected from the group consisting of: GLUT1, GLUT2, GLUT3, GLUT4, GLUT5, GLUT6, GLUT7, GLUT8, GLUT9-1, GLUT10, GLUT11-a, GLUT12, GLUT13 (HMIT) and GLUT14, preferably from GLUT1, GLUT2, GLUT3, GLUT4 and GLUT14, more preferably from GLUT1, GLUT3, and GLUT4 and most preferably from GLUT1 and GLUT3.

Thus, the compounds according to the general formula (I) as well as pharmaceutically acceptable salts thereof are used as an inhibitor for GLUTs, preferably for GLUT1, GLUT2, GLUT3, GLUT4 and GLUT14, more preferably for GLUT1, GLUT3 and GLUT4 and most preferably for GLUT1 and GLUT3.

Surprisingly it turned out that the compounds according to the general formula (I) as well as pharmaceutically acceptable salts thereof selectively inhibit GLUT1 and GLUT3 in comparison to other glucose transporters, especially GLUT 4. Thus, the compounds according to the general formula (I) as well as pharmaceutically acceptable salts thereof are used as selective inhibitors for GLUT1 and GLUT3.

As used herein, a glucose transporter "inhibitor" refers to any compound capable of downregulating, decreasing, suppressing or otherwise regulating the amount and/or activity of a glucose transporter. Inhibition of these glucose transporters can be achieved by any of a variety of mechanisms known in the art, including, but not limited to binding directly to the glucose transporter polypeptide, denaturing or otherwise inactivating the glucose transporter, or inhibiting the expression of the gene (e.g., transcription to mRNA, translation to a nascent polypeptide, and/or final polypeptide modifications to a mature protein), which encodes the glucose transporter. Generally, glucose transporter inhibitors may be proteins, polypeptides, nucleic acids, small molecules, or other chemical moieties.

As used herein the term "inhibiting" or "inhibition" refers to the ability of a compound to downregulate, decrease, reduce, suppress, inactivate, or inhibit at least partially the activity of an enzyme, or the expression of an enzyme or protein and/or the virus replication.

In a further aspect of the present invention, the compound according to the general formula (I) is used as a medicament.

Preferred, the compound according to the general formula (I) is used in in the prophylaxis or treatment of diseases caused by, or associated with GLUT1 and/or GLUT3.

One embodiment of the present invention is directed to the compound of general formula (I) for use in prophylaxis or treatment of a metabolic disease, immunological diseases, autoimmune diseases, inflammation, graft versus host disease, a proliferative disease, especially cancer or metastasis thereof.

The Metabolic Disease

The metabolic disease is selected from the group consisting of: diabetes type 1 and type 2, insulin resistance, metabolic syndrome, hyperinsulinemia, dyslipidemia, and hypercholesterolemia, obesity, hypertension, retinal degeneration, or retinal detachment.

Immunological Diseases

Another aspect of the present invention is directed to the use of a compound of the general formula (I) and/or pharmaceutically acceptable salts thereof for prophylaxis and/or treatment of immunological diseases, neuroimmunological diseases, and autoimmune diseases.

Immunological diseases are, for instance, asthma and diabetes, rheumatic and autoimmune diseases, AIDS, rejection of transplanted organs and tissues (cf. below), rhinitis, chronic obstructive pulmonary diseases, osteoporosis, ulcerative colitis, sinusitis, lupus erythematosus, recurrent infections, atopic dermatitis/eczema and occupational allergies, food allergies, drug allergies, severe anaphylactic reactions, anaphylaxis, and other manifestations of allergic disease, as well as uncommon problems such as primary immunodeficiencies, including antibody deficiency states, cell mediated immunodeficiencies (e.g., severe combined immunodeficiency, DiGeorge syndrome, Hyper-IgE syndrome, Wiskott-Aldrich syndrome, ataxia-telangiectasia), immune mediated cancers, and white cell defects.

In autoimmune diseases, such as systemic lupus erythematosus, rheumatoid arthritis (RA), multiple sclerosis (MS), immune-mediated or type 1 diabetes mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, and Hashimoto's disease, dermatomyositis, goodpasture syndrome, myasthenia gravis pseudoparalytica, ophtalmia sympatica, phakogene uveitis, chronical agressivce hepatitis, primary billiary cirrhosis, autoimunehemolytic anemy, Werlof disease, specific cells uncontrollably attack the body's own tissues and organs (autoimmunity), producing inflammatory reactions and other serious symptoms and diseases.

Hashimoto's thyroiditis is one of the most common autoimmune diseases. "Autoimmune disease" refers to a category of more than 80 chronic illnesses that can affect everything from the endocrine glands (like the thyroid) to organs like the kidneys, as well as to the digestive system.

There are many different autoimmune diseases, and they can each affect the body in different ways. For example, the autoimmune reaction is directed against the brain in multiple sclerosis and the gut in Crohn's disease. In other autoimmune diseases such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in type 1 diabetes mellitus.

Inflammation

In yet another preferred embodiment, said inflammation is mediated preferably by the cytokines TNF-α, IL-1ß, GM-CSF, IL-6 and/or IL-8.

As described above, the compounds according to general formula (I) are pharmaceutically active agents for prophylaxis and/or treatment of inflammatory diseases. Thus, these compounds are used for prophylaxis and/or treatment of inflammations and inflammatory diseases in mammals, including humans.

Inflammatory diseases can emanate from infectious and non-infectious inflammatory conditions which may result from infection by an invading organism or from irritative, traumatic, metabolic, allergic, autoimmune, or idiopathic causes as shown in the following list.

| I. | Acute infections | | |
|---|---|---|---|
| | A. Viral | B. | Bacterial |
| II. | Noninfectious causes | | |
| III. | Chronic (granulomatous) diseases | | |
| | A. Bacterial | B. | Spirochetal |
| | C. Mycotic (Fungal) | D. | Idiopathic |
| IV. | Allergic, immune, and idiopathic disorders | | |
| | A. Hypersensitivity reactions | | |
| | B. Immune and idiopathic disorders | | |
| V. | Miscellaneous inflammatory conditions | | |
| | A. Parasitic infections | | |
| | B. Inhalation causes: | Acute (thermal) injury | |
| | | Pollution and inhalant allergy | |
| | | Carcinogens | |
| | C. Radiation injury: | Radionecrosis | |

Thus, the compounds disclosed herein can be used for prophylaxis and/or treatment of inflammations caused by invading organisms such as viruses, bacteria, prions, and parasites as well as for prophylaxis and/or treatment of inflammations caused by irritative, traumatic, metabolic, allergic, autoimmune, or idiopathic reasons.

Consequently, the disclosed compounds are useful for prophylaxis and/or treatment of inflammatory diseases which are initiated or caused by viruses, parasites, and bacteria which are connected to or involved in inflammations.

The following bacteria are known to cause inflammatory diseases: *Mycoplasma pulmonis* (causes e.g. chronic lung diseases (CLD), murine chronic respiratory disease), *Ureaplasma urealyticum* (causes pneumonia in newborns), *Mycoplasma pneumoniae* and *Chlamydia pneumoniae* (cause chronic asthma), *C. pneumoniae* (causes atherosclerosis, pharyngitis to pneumonia with empyema, human coronary heart disease), *Helicobacter pylori* (human coronary heart disease, stomach ulcers). The following viruses are known to cause inflammatory diseases: herpesviruses especially cytomegalovirus (causes human coronary heart disease).

The compounds disclosed herein are useful for prophylaxis and/or treatment of inflammatory diseases caused and/or induced and/or initiated and/or enhanced by the afore-mentioned bacteria or viruses.

Furthermore, the compounds of formula (I) are useful for prophylaxis and/or treatment of inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, inflammatory diseases of the larynx.

Examples for inflammatory diseases of the central nervous system (CNS) are algal disorders, protothecosis, bacterial disorders, abscessation, bacterial meningitis, idiopathic inflammatory disorders, eosinophilic meningoencephalitis, feline polioencephalomyelitis, granulomatous meningoencephalomyelitis, meningitis, steroid responsive meningitis-arteritis, miscellaneous meningitis/meningoencephalitis, meningoencephalitis in greyhounds, necrotizing encephalitis, pyogranulomatous meningoencephalomyelitis, shaker dog disease, mycotic diseases of the CNS, parasitic encephalomyelitis, prion protein induced diseases, feline spongiform encephalopathy, protozoal encephalitis-encephalomyelitis, toxoplasmosis, neosporosis, sarcocystosis, encephalitozoonosis, trypanosomiasis, acanthamebiasis, babesiosis, leishmaniasis, rickettsial disorders, rocky mountain spotted fever, canine ehrlichiosis, salmon poisoning, viral disorders, aujeszky's disease, borna disease, canine herpes virus encephalomyelitis, canine distemper encephalomyelitis, canine distemper encephalomyelitis in immature animals, chronic relapsing encephalomyelitis, post-vaccinal canine distemper encephalitis, feline immunodeficiency virus, feline infectious peritonitis, feline leukemia virus, infectious canine hepatitis, La Crosse virus encephalitis, parvovirus encephalitis, rabies, post-vaccinal rabies.

Examples for inflammatory rheumatic diseases are rheumatoid arthritis, scleroderma, lupus, polymyositis, dermatomyositis, psoriatic arthritis, ankylosing spondylitis, Reiters's syndrome, juvenile rheumatoid arthritis, bursitis, tendinitis (tendonitis), and fibromyositis.

Examples for inflammatory diseases of blood vessels are vasculitis, autoantibodies in vasculitis, microscopic polyangiitis, giant cell arteritis, Takayasu's arteritis, vasculitis of the central nervous system, thromboangiitis obliterans (Buerger's Disease), vasculitis secondary to bacterial, fungal, and parasitic infection, vasculitis and rheumatoid arthritis, vasculitis in systemic lupus erythematosus, vasculitis in the idiopathic inflammatory myopathies, relapsing polychondritis, systemic vasculitis in sarcoidosis, vasculitis and malignancy, and drug-induced vasculitis.

Examples for inflammatory diseases of the middle ear are acute suppurative otitis media, bullous myringitis, granular myringitis, and chronic suppurative otitis media, which can manifest as mucosal disease, cholesteatoma, or both.

Examples for inflammatory bowel diseases are ulcerative colitis, Crohn's disease.

Examples for inflammatory diseases of the skin are acute inflammatory dermatoses, urticaria (hives), spongiotic dermatitis, allergic contact dermatitis, irritant contact dermatitis, atopic dermatitis, erythemal multiforme (EM minor), Stevens-Johnson syndrome (SJS, EM major), toxic epidermal necrolysis (TEN), chronic inflammatory dermatoses, psoriasis, lichen planus, discoid lupus erythematosus, and acne vulgaris.

Uveitis are inflammations located in and/or on the eye and may be associated with inflammation elsewhere in the body. In most circumstances, patients who have uveitis as part of a disease elsewhere in the body are aware of that illness. The majority of patients with uveitis do not have an apparent associated systemic illness. Causes of uveitis can be infectious causes, masquerade syndromes, suspected immune-mediated diseases, and/or syndromes confined primarily to the eye.

The following viruses are associated with inflammations: human immunodeficiency virus-I, herpes simplex virus, herpes zoster virus, and cytomegalovirus.

Bacterial or spirochetal caused, induced, initiated and/or enhanced inflammations are tuberculosis, leprosy, proprionobacterium, syphilis, Whipple's disease, leptospirosis, brucellosis, and lyme disease.

Parasitic (protozoan or helminthic) caused, induced, initiated and/or enhanced inflammations are toxoplasmosis, acanthameba, toxocariasis, cysticercosis, onchocerciasis.

Examples of inflammatory diseases caused, induced, initiated and/or enhanced by fungi are histoplasmosis, coccidioidomycosis, candidiasis, aspergillosis, sporotrichosis, blastomycosis, and cryptococcosis.

Masquerade syndromes are, for instance, leukemia, lymphoma, retinitis pigmentosa, and retinoblastoma.

Suspected immune-mediated diseases can be selected from the group comprising ankylosing spondylitis, Behcet's disease, Crohn's disease, drug or hypersensitivity reaction, interstitial nephritis, juvenile rheumatoid arthritis, Kawasaki's disease, multiple sclerosis, psoriatic arthritis, Reiter's syndrome, relapsing polychondritis, sarcoidosis, Sjogren's syndrome, systemic lupus erythematosus, ulcerative colitis, vasculitis, vitiligo, Vogt Koyanagi Harada syndrome.

Syndromes confined primarily to the eye are, for instance, acute multifocal placoid pigmentary epitheliopathy, acute retinal necrosis, birdshot choroidopathy, Fuch's heterochromic cyclitis, glaucomatocyclitic crisis, lens-induced uveitis, multifocal choroiditis, pars planitis, serpiginous choroiditis, sympathetic ophthalmia, and trauma.

Examples for inflammatory diseases of the larynx are gastroesophageal (laryngopharyngeal) reflux disease, pediatric laryngitis, acute laryngeal infections of adults, chronic (granulomatous) diseases, allergic, immune, and idiopathic disorders and miscellaneous inflammatory conditions.

Pediatric laryngitis is known as acute (viral or bacterial) infection such as laryngotracheitis (croup), supraglottitis (epiglottitis), diphtheria, and noninfectious causes are for example spasmodic croup and traumatic laryngitis.

Acute laryngeal infections of adults are, for instance, viral laryngitis, common upper respiratory infection, laryngotracheitis, herpes simplex, bacterial laryngitis, supraglottitis, laryngeal abscess, and gonorrhea.

Chronic (granulomatous) diseases can be selected from the group comprising bacterial diseases, tuberculosis, leprosy, scleroma, actinomycosis, tularemia, glanders, spirochetal (syphilis) diseases, mycotic (fungal) diseases, candidiasis, blastomycosis, histoplasmosis, coccidiomycosis, aspergillosis, idiopathic diseases, sarcoidosis, and Wegener's granulomatosis.

Allergic, immune, and idiopathic disorders are, for example, hypersensitivity reactions, angioedema, Stevens-Johnson syndrome, immune and idiopathic disorders, infections of the immunocompromised host, rheuatoid arthritis, systeic lupus erythematosus, cicatricial pemphigoid, relapsing polychondritis, Sjogren's syndrome, and amyloidosis.

Miscellaneous inflammatory conditions are, for instance, parasitic infections, trichinosis, leishmaniasis, schistosomiasis, syngamus laryngeus, inhalation laryngitis, acute (thermal) injury, pollution and inhalant allergy, carcinogens, radiation injury, radiation laryngitis, radionecrosis, vocal abuse, vocal-cord hemorrhage, muscle tension dysphonias, and contact ulcer and granuloma.

Proliferative Disease

The term "proliferative diseases" as used herein refers also to tumors, cancer, malignancies and their metastases. Additionally it refers also to benign proliferative diseases, which may be harmful producing a "mass effect" (compression of vital organs or closure of hollow organs such as blood vessels), or benign tumors of endocrine tissues, which may overproduce certain hormones.

The proliferation disorders and cancers are preferably selected from the group comprising or consisting of adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, estrogen dependent and independent breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, carniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's lymphomas), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma, tongue cancer, invasive ductal carcinoma, invasive lobular carcinoma, ductal carcinoma in situ, lobular carcinoma in situ, small-cell lung carcinoma, non-small-cell lung carcinoma, bronchial adenoma, pleuropulmonary blastoma, mesothelioma, brain stem glioma, hypothalmic glioma, cerebellar astrocytoma, cerebral astrocytoma, neuroectodermal tumours, pineal tumors, sarcoma of the uterus, salivary gland cancers, anal gland adenocarcinomas, mast cell tumors, pelvis tumours, ureter tumours, hereditary papillary renal cancers, sporadic papillary renal cancers, intraocular melanoma, hepatocellular carcinoma (liver cell carcinomas with or without fibrolamellar variant), cholangiocarcinoma (intrahepatic bile duct carcinoma), mixed hepatocellular cholangiocarcinoma, squamous cell carcinoma, malignant melanoma, Merkel cell skin cancer, non-melanoma skin cancer, hypopharyngeal cancer, nasopharyngeal cancer, oropharyngeal cancer, oral cavity cancer, squamous cell cancer, oral melanoma, AIDS-related lymphoma, cutaneous T-cell lymphoma, lymphoma of the central nervous system, malignant fibrous histiocytoma, lymphosarcoma, rhabdomyosarcoma, malignant histiocytosis, fibrosarcoma, hemangiosarcoma, hemangiopericytoma, leiomyosarcoma, canine mammary carcinoma, and feline mammary carcinoma.

Preferred are the following cancer types: leukemias including but not limited to chronic lymphocytic leukemia, chronic myelogenous leukemia, acute lymphoblastic leukemia, acute myeloid leukemia, mixed lineage leukemia, bladder cancer, brain cancer, breast cancer, cervical cancer, cancer of the central nervous system, colon cancer, colorectal cancer, gastric cancer, lung cancer, kidney cancer, melanoma, ovarian cancer, glioblastomas, pancreatic cancer, prostate cancer, stomach cancer, skin cancer, skin testis cancer, Hodgkin's lymphoma, liver cancer, liver metastases and renal cell carcinomas.

In a further aspect of the present invention, a method for preventing and/or treating said metabolic disease, immunological diseases, autoimmune diseases, inflammation, graft versus host disease, cancer or metastasis, in a mammal, especially in a human, is provided, which method comprises administering to the mammal an amount of at least one compound according to the general formula (I), effective to prevent and/or treat said metabolic disease, immunological diseases, autoimmune diseases, inflammation, graft versus host disease, cancer or metastasis.

In a further aspect of the present invention, methods for preventing and/or treating metabolic disease, immunological diseases, autoimmune diseases, inflammation, graft versus host disease, cancer or metastasis in a mammal, especially in a human, are provided, which methods comprise administering to the mammal an amount of at least one compound according to the general formula (I) and/or pharmaceutically acceptable salts thereof, effective to prevent and/or treat said metabolic disease, immunological diseases, autoimmune diseases, inflammation, graft versus host disease, cancer or metastasis.

Thus, another aspect of the present invention relates to drug combinations comprising at least one inventive compound according to general formula (I) and/or pharmaceutically acceptable salts thereof together with at least one anticancer drug, especially at least one of the drugs mentioned above.

Thus, the compounds of the present invention are used for the manufacture of a pharmaceutical formulation for prophylaxis and/or treatment of a metabolic disease, immunological diseases, autoimmune diseases, inflammation, graft versus host disease, cancer or metastasis.

The pharmaceutical compositions or formulations according to the present invention comprise at least one compound according to the present invention as an active ingredient together with at least one pharmaceutically acceptable (i.e. non-toxic) carrier, excipient and/or diluent. The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule.

Powders and tablets may contain about 5 to about 95-weight % of the pyrazolo[1,5-a][1,3,5]triazine derivatives according to the general formula (I) or analogues compound thereof or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration.

Aerosol preparations suitable for inhalation may include solutions and solids in powder form, which may be present in combination with a pharmaceutically acceptable carrier such as an inert, compressed gas, e.g. nitrogen.

For preparing suppositories, a low melting wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methylcellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives.

Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix.

Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble"

modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to ca. 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidants are materials that prevent caking of the components of the pharmaceutical composition and improve the flow characteristics of granulate so that flow is smooth and uniform. Suitable glidants include silicon dioxide and talc. The amount of glidants in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

EXAMPLES

Preparation of Compounds

Abbreviations Used in the Present Description have the Following Meanings:

AcOH (acetic acid), $CDCl_3$ (deuterated chloroform); cHex (cyclohexane); DCM (dichloromethane); DIPEA (N-ethyl-N,N-diisopropylamine); DMAP (4-dimethylamino-pyridine); DMF (dimethylformamide); DMSO (dimethyl sulfoxide); eq (equivalent); ES (electrospray); EtOAc (ethyl acetate); EtOH (ethanol); MeOH (methanol); MeCN (acetonitrile); MS (mass spectrometry); NMR (nuclear magnetic resonance); iPrOH (iso-propanol); PCC (pyridinium chlorochromate); RT (room temperature); TMSCl (trimethylsilyl chloride); TBTU [2(1H-benzotriazol-1-yl)N,N,N',N'-tetramethylaminium tetrafluoroborate], THF (tetrahydrofuran).

All reactions involving air or moisture sensitive reagents or intermediates were carried out following standard Schlenk line technique under an nitrogen atmosphere and all the glassware was dried by heat gun under high vacuum prior to use. Dry solvents were received from Acros in anhydrous quality and used without any further purification. All other solvents or reagents were purified according to standard procedures or were used as received from Sigma Aldrich, Alfa Aesar, Acros, Activate Scientific, Matrix Scientific, Combi Blocks, Fisher Scientific, Merck and TCI. Milli-Q grade water was used for all experiments. Solvents for chromatography were technical grade.

TLC was performed using pre-coated Merck silica gel 60 F254 glass plates, detection of compounds were performed by UV254 light and/or dipping into a solution of KMnO4 (1.5 g in 400 mL $H_2O$, 5 g $NaHCO_3$) followed by heating with a heat gun. Column chromatography was performed using silica gel from Acros Organics (40-65 μm, 230-400 mesh). Solvent mixtures are understood as volume/volume. Used eluents are stated in each section.

$^1$H-NMR and $^{13}$C-NMR were recorded on a Bruker DRX400 (400 MHz), Bruker DRX500 (500 MHz) and INOVA500 (500 MHz) or INOVA 600 and on a device from Varian (Mercury 400 MHz), using $CDCl_3$, DMSO-$d_6$, or $CD_3OD$ as solvent. Data are reported in the following order: chemical shift (δ) values are reported in ppm with the solvent resonance as internal standard ($CDCl_3$: δ=7.26 ppm for $^1$H, δ=77.16 ppm for $^{13}$C), (DMSO-$d_6$: δ=2.50 ppm for $^1$H, δ=39.52 for $^{13}$C), ($CD_3OD$: δ=3.31 ppm for $^1$H, δ=49.00 ppm for $^{13}$C) multiplicities are indicated bs (broadened singlet), s (singlet), d (doublet), t (triplet), q (quartet), m (multiplet), dd (doublet of doublet), dt (doublet of triplet); coupling constants (J) are given in Hertz (Hz). Unless stated otherwise all NMRs were measured at room temperature. Where possible, structural assignments were attempted using standard 2-D NMR techniques (gCOSY, gHSQC, gHMBC).

Preparative HPLC-MS: Separations were carried out using a preparative mass-directed HPLC (Agilent Series, 1100/LC/MSD VL, Agilent Series) with a reversed-phase C18 column (flow 20.0 mL/min, solvent A: 0.1% TFA in water, solvent B: 0.1% TFA in acetonitrile).

High resolution mass spectra were recorded on a LTQ Orbitrap mass spectrometer coupled to an Accela HPLC-System (HPLC column: Hypersyl GOLD, 50 mm×1 mm, particle size 1.9 μm, ionization method: electron spray ionization).

Optical rotations were measured in a Schmidt+Haensch Polartronic HH8 polarimeter. The enantiomeric excess was determined by HPCL analysis using a chiral stationary phase column (column: as stated below; eluent: as stated below). The chiral HPLC methods were calibrated with the corresponding racemic mixtures. Chemical yields refer to pure isolated substances.

General Procedures:
A. Urea Formation:

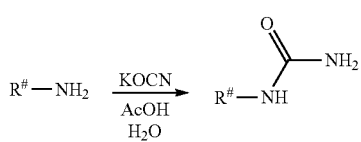

In a typical example, KOCN (5 mmol, 5 eq.) was added to a stirred solution of the amine (1 mmol, 1 eq.) in $H_2O$—AcOH (2:1, 10 mL, 0.1 M) and stirred at r.t. After 18 h a solid was formed and the reaction mixture was cooled to 0° C., filtered in vacuo. The amorphous solid was washed with cold $H_2O$ (2×20 mL). The solid was collected, dried and used directly without further purification.

B. Phenol Acetylation:

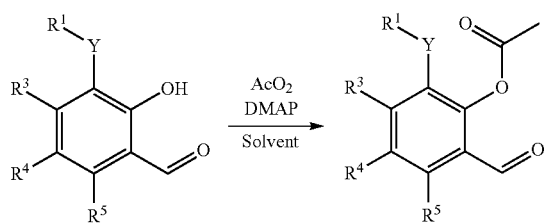

In a typical example, acetic anhydride (200 μL, 2.1 mmol, 1.05 eq.) was added to a stirred solution of the phenol (2 mmol, 1 eq.) and DMAP (24 mg, 0.2 mmol, 0.1 eq.) in Toluene or $CH_2Cl_2$ and the mixture was stirred at r.t. After 20 h, the reaction mixture was concentrated in vacuo and filtered through a silica column (2 mmol scale, 6 cm×Ø2 cm) eluting with 50% EtOAc in Petroleum Ether (300 mL). The eluent was collected and concentrated in vacuo to give a crude product which was used directly without further purification.

C. Biginelli Reaction:

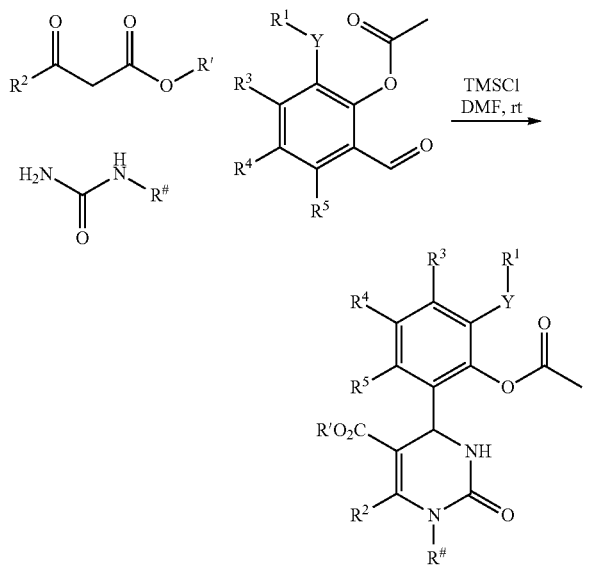

In a typical example, trimethylchlorosilane (770 μL, 6 mmol, 6 eq.) was added dropwise to a stirred solution of the appropriate urea (1 mmol, 1 eq.), aldehyde (1 mmol, 1 eq.) and methylacetoacetate (180 μL, 1.5 mmol, 1.5 eq.) in DMF (1 mL, 1 M), and the resulting mixture was stirred at r.t. After 18 h, the reaction was quenched with $H_2O$ (2 mL) and diluted with EtOAc (40 mL). The organic layer was extracted sequentially with $H_2O$ (5×20 mL), sat. aq. LiCl solution (1×20 mL) and sat. aq. NaCl solution (1×20 mL), dried over $Na_2SO_4$, filtered and concentrated in vacuo to give a crude product.

D. Deprotection, Cyclisation and Decarboxylation One-Pot Process:

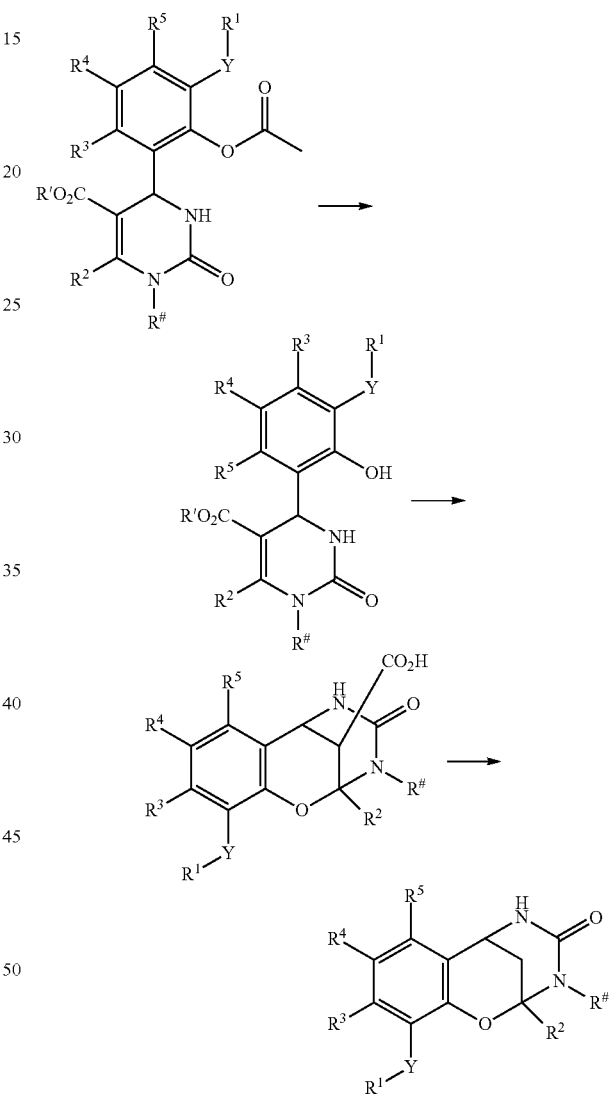

In a typical example, saturated $NaHCO_3$ aq. solution (10 mL) was added to a stirred solution of the dihydropyrimidinone (Biginelli product, 1 mmol) in MeOH (10 mL) and the resulting suspension was heated to 40° C. After 16 h the reaction mixture was allowed to cool to r.t. and was concentrated in vacuo. The crude was diluted with THF—$H_2O$ (1:1, 10 mL, 0.1 M), LiOH (15 eq. for each methyl ester group) was added and the reaction mixture was heated to 40° C. After 18 h, the reaction mixture was allowed to cool to r.t. and was concentrated in vacuo to half volume. The reaction mixture was acidified to pH=1-2, by slow addition of 1 M aq. HCl solution and was heated to 80° C. (probe temperature 82° C.). After 6 h, the reaction mixture was allowed to cool to r.t. and extracted with CHCl₃-MeOH (8:2, 5×20 mL). The combined organic layers were dried over Na₂SO₄, filtered and concentrated in vacuo to give a crude product.

E. Telescoped Combination of Procedures C and D:

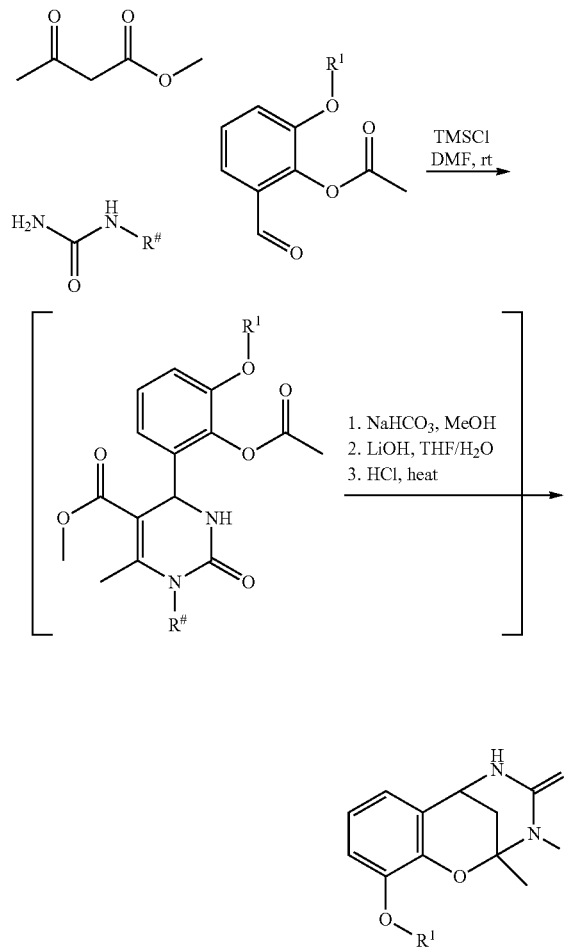

The Biginelli reaction was carried out as outlined in General Procedure C. After 18 h, the reaction was quenched with H₂O (2 mL) and diluted with EtOAc (40 mL). The organic layer was extracted sequentially with H₂O (5×20 mL), sat. aq. LiCl solution (1×20 mL) and sat. aq. NaCl solution (1×20 mL), dried over Na₂SO₄, filtered and concentrated in vacuo to give a crude product, which was directly submitted to the conditions outlined in General Procedure D, yielding a crude product.

F. Amide Coupling:

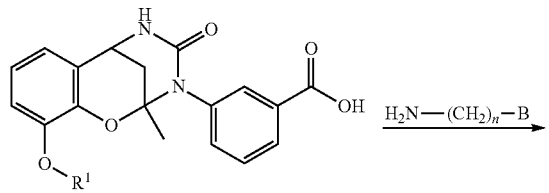

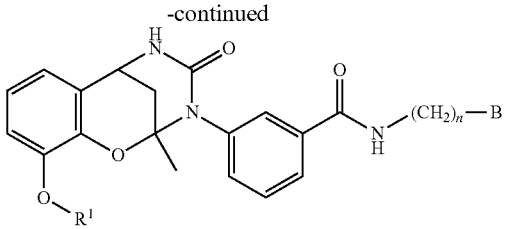

In a typical example, O-(Benzotriazol-1-yl)-N,N,N',N'-tetramethyluronium Tetrafluoroborate (TBTU, 1.5 eq.) was added to a stirred solution of the acid (1 mmol, 1 eq.) and DIPEA (1.5 eq.) in DMF (4 mL, 0.25 M) at r.t. After 1 h, the amine was added (1.2 eq.) and the resulting mixture was stirred at r.t. After 18 h, H₂O (20 mL) was added and the mixture was diluted with EtOAc (80 mL) and layers separated. The organic layer was extracted sequentially with H₂O (5×40 mL), sat. aq. LiCl solution (1×40 mL) and sat. aq. NaCl solution (1×40 mL), dried over Na₂SO₄, filtered and concentrated in vacuo to give a crude product.

G. Phenol Alkylation:

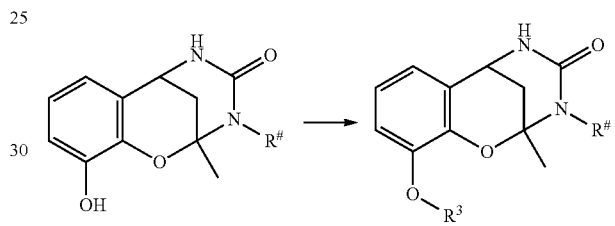

In a typical example, the aromatic/heteroaromatic alkyl halide (0.1 mmol, 1 eq.) was added to a stirred suspension of the phenol (0.1 mmol, 1 eq.) and K₂CO₃ (0.2 mmol, 2 eq.) in MeCN (200 μL, 0.5 M) and heated to reflux (probe temperature 85° C.). After 4 h, the reaction mixture was allowed to cool to r.t. and concentrated in vacuo to give a crude product.

H. Enantioselective Biginelli Reaction:
Preparation of Chiral Phosphoric Acid, 74:

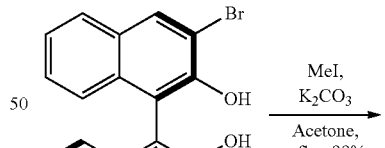

70

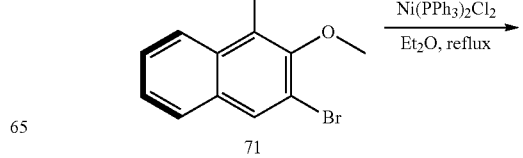

71

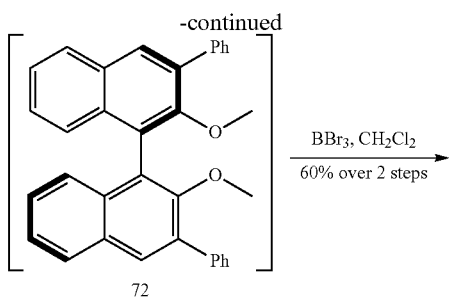

72

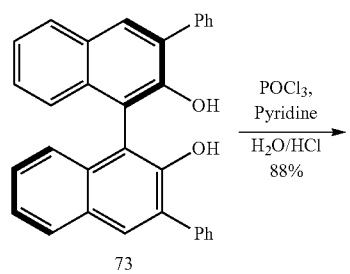

73

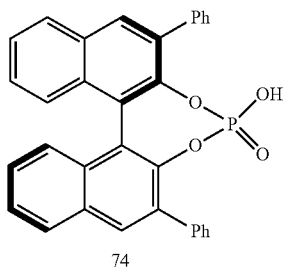

74

Following the process described by Klussmann et al. (*Synlett* 2010, 2010 (14), 2189), the chiral phosphoric acid was prepared from (S)-(−)-3,3'-Dibromo-1,1'-bi-2-naphthol, in 52% yield over three steps. Iodomethane (560 mL, 9.0 mmol) was added to a stirred suspension of the naphthol (1.00 g, 2.3 mmol) and potassium carbonate (1.03 g, 7.4 mmol) in Acetone (21 mL, 0.11 M) and the resulting mixture was heated to reflux (83° C.). After 18 h, the reaction mixture was allowed to cool to r.t. and concentrated in vacuo. The crude was rediluted in $H_2O$ (21 mL) and stirred at r.t. After 2 h, the mixture was filtered eluting with $H_2O$ (2×10 mL) and the sub-yellow solid, 71 collected (1.1 g, 99%). $^1$H NMR (500 MHz, CDCl$_3$): d 8.19 (2H, s), 7.74 (2H, d, J 8.4 Hz), 7.34 (2H, dt, J 7.4 and 1.1 Hz), 7.19 (2H, dt, J 7.4 and 1.1 Hz), 7.00 (2H, d, J 8.4 Hz), 3.43 (6H, s). The methylated dibromobinapthol 71 (1.1 g, 2.34 mmol), was diluted in Et$_2$O (14 mL, 0.17 M) and Ni(PPh$_3$)$_2$Cl$_2$ (153 mg, 0.23 mmol) was added under Argon atmosphere. Phenyl magnesium bromide (8.8 mL, 1.6 M in CPME) was added dropwise over 10 min and the resulting mixture was heated to reflux (37° C.). After 23 h, the reaction mixture was allowed to cool to r.t., then cooled to 0° C., and quenched by careful, dropwise addition of 1 M HCl aqueous solution (16 mL). The mixture was extracted with Et$_2$O (4×10 mL) and the combined organic layers were dried over Na$_2$SO$_4$, filtered and concentrated in vacuo to give the crude product 72, which was used directly without further purification. The crude was diluted in dry CH$_2$Cl$_2$ (59 mL, 0.04 M) and cooled to 0° C. BBr$_3$ (1.6 mL, 16.4 mmol) was added slowly and dropwise to reaction mixture under Argon atmosphere. The resulting mixture was stirred and allowed to warm to r.t. After 18 h, the reaction mixture was cooled to 0° C. and the reaction was quenched by the careful addition of H$_2$O (20 mL). The resulting slurry was stirred at r.t. for 1 h, extracted with CH$_2$Cl$_2$ (4×20 mL) and the combined organic layers were dried over Na$_2$SO$_4$, filtered and concentrated in vacuo to give a crude product. Purification by flash chromatography eluting with 2-4% EtOAc in Cyclohexane afforded the bis-phenyl binaphthol 73 as a slightly yellow amorphous solid (620 mg, 1.42 mmol, 60%). $^1$H NMR (500 MHz, CDCl$_3$): δ 8.09 (2H, s), 7.98 (2H, d, J 8.1 Hz), 7.82-7.77 (4H, m), 7.57-7.51 (4H, m), 7.49-7.41 (4H, m), 7.40-7.34 (2H, m), 7.33-7.28 (2H, m), 5.42 (2H, s). The bis-phenyl-binaphthol 73 (620 mg, 1.4 mmol) was diluted in pyridine (2.8 mL, 0.5 M) and POCl$_3$ (390 mL, 4.3 mmol) was added and the reaction mixture was heated to reflux (120° C.). After 18 h, the reaction mixture was allowed to cool to r.t. and H$_2$O (2.8 mL) was added and the resulting slurry was heated to reflux (103° C.). After 3 h the reaction mixture was allowed to cool to r.t. and was acidified to pH ca 1 by the slow addition of conc. HCl solution. CH$_2$Cl$_2$ (20 mL) was added and layers separated. The organic layer was washed with 1 M HCl solution (4×20 mL) checking the pH to be strongly acidic throughout the work-up and extraction procedures in order to isolate the product in the free acid form. The organic layer was dried over Na$_2$SO$_4$, filtered and concentrated in vacuo to give 74 as a crude product which required no further purification. Amorphous solid (623 mg, 1.24 mmol, 88%) with spectroscopic data matching those previously reported. (Hatano, M. et al., *Advanced Synthesis & Catalysis* 2008, 350 (11-12), pp. 1776.; Li, N. et al., *Journal of the American Chemical Society* 2009, 131 (42), pp. 15301)$^1$H NMR (500 MHz, CDCl$_3$): δ 7.94 (2H, m), 7.55 (4H, d, J 7.8 Hz), 7.45 (2H, app t, J 7.8 Hz), 7.35 (2H, d, J 7.8 Hz), 7.29-7.22 (4H, m), 7.18-7.05 (6H, m).

Enantioselective Biginelli Reaction:

By the method of Li N. et al. (*Advanced Synthesis & Catalysis* 2008, 350 (11-12), pp. 1776), the urea 2 (194 mg, 1 mmol), aldehyde 3 (312 mg, 1.5 mmol) and (S)-(−)-3,3'-bisphenyl-1,1'-bi-2-naphthyl phosphoric acid 74 (125 mg, 0.25 mmol), were stirred at r.t. in PhMe (7.7 mL, 0.17 M). After 1 h the reaction mixture was heated to 30° C. After 1 h, methyl acetoacetate (540 mL, 5 mmol), was added and the reaction mixture was heated to 40° C. After 6 days, the reaction mixture was allowed to cool to r.t. and concentrated in vacuo to give a crude product. Purification by flash chromatography eluting with 20-40% EtOAc in Hexane afforded the enantioenriched (S)-DHMP, 4.
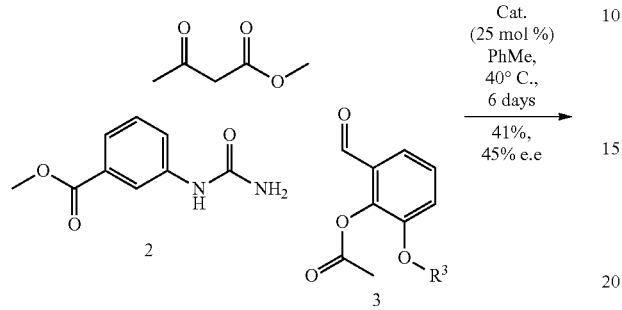
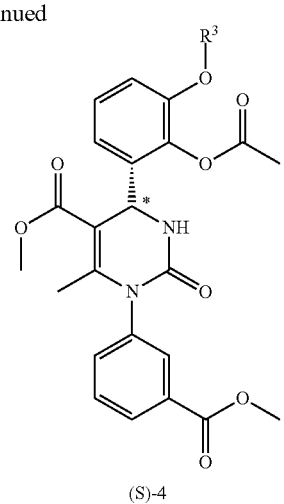
Synthesis of Enantioenriched Product:
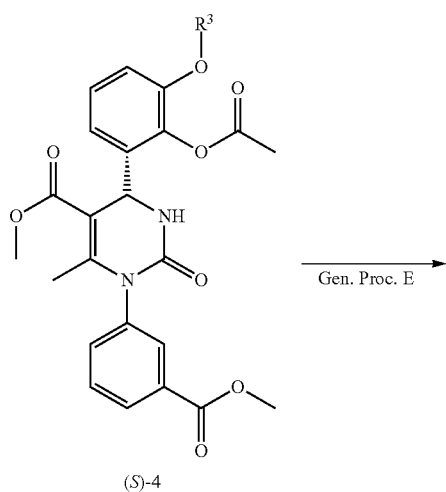
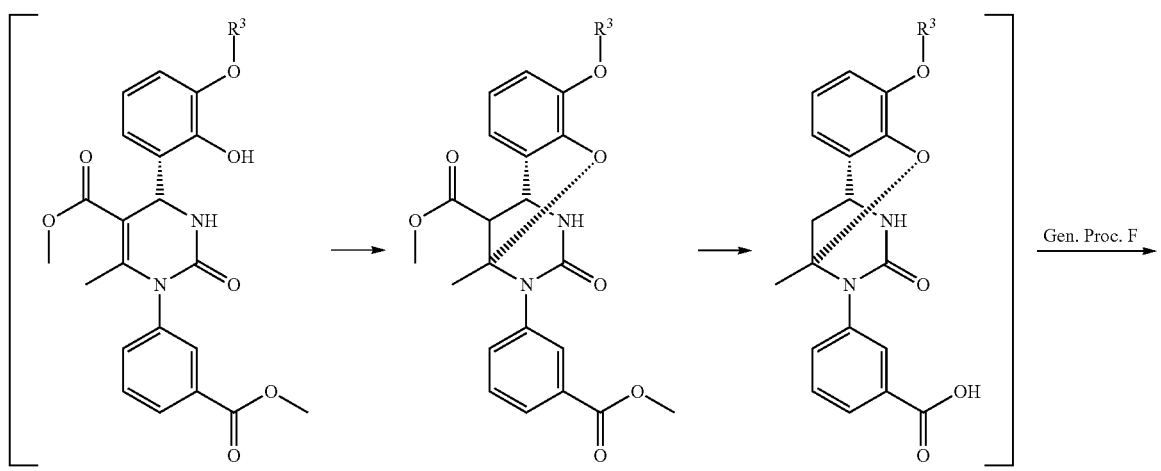

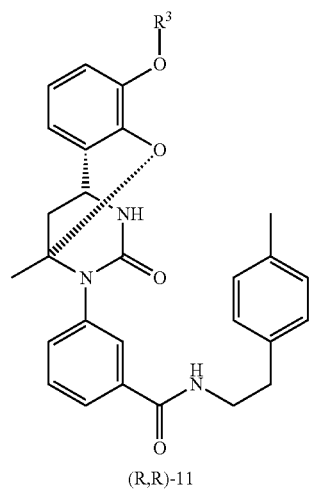

(R,R)-11

The enantioenriched (S)-DHMP, 4 (200 mg, 0.4 mmol) was submitted to General Procedure E, directly followed by General procedure F, using 2-(p-tolyl)-ethylamine. Purification by prep-HPLC eluting with 10-100% MeCN in H$_2$O (no TFA), gave the enantioenriched (−)-(R,R)-Chromopynone-1 as a colourless amorphous solid (45 mg, 0.19 mmol, 46% over 4 steps) with spectroscopic data matching those of the racemic Chromopynone-1. $[\alpha]_D^{23}=-0.260$ (c=0.019, CHCl$_3$). The enantiomeric excess (40%) of the product was determined by chiral HPLC analysis on a CHIRALPAK-IA column eluting with a gradient of 70-80% (2% EtOH in CH$_2$Cl$_2$) in Hexane.

Example 1-1: Preparation of 2-acetoxy-5-chloro-benzaldehyde, 1-1

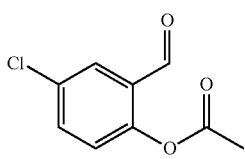

By General Procedure B, using 5-chlorosalicylaldehyde (783 mg, 5 mmol). Pale yellow solid (944 mg, 4.8 mmol, 95%). $^1$H NMR (500 MHz, CDCl$_3$): δ 9.97 (1H, s, Formyl-H), 7.77 (1H, d, J 2.6, Ph-6H), 7.50 (1H, dd, J 8.6 and 2.6 Hz, Ph-4H), 7.08 (1H, d, J 8.6 Hz, Ph-3H), 2.32 (3H, s, Ac-2H$_3$). $^{13}$C NMR (125 MHz, CDCl$_3$): δ 187.3 (Formyl-C), 169.0 (Ac—C1), 150.1 (Ph-C2), 135.1 (Ph-C6), 132.3 (Ph-C5), 130.4 (Ph-C4), 129.0 (Ph-C2), 125.0 (Ph-C3), 20.7 (Ac—C2). HRMS (ESI): C$_9$H$_8$O$_3$Cl [M+H]$^+$; Requires: 199,0156. Found: 199,0153.

Example 1-2: Preparation of 2-Acetoxy-4-methoxy-benzaldehyde, 1-2

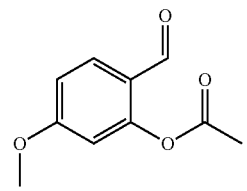

By General Procedure B, using 4-methoxy salicylaldehyde (761 mg, 5 mmol). Pale yellow oil (893 mg, 4.6 mmol, 92%). $^1$H NMR (500 MHz, CDCl$_3$): δ 9.93 (1H, s, Formyl-H), 7.80 (1H, d, J 8.6, Ph-6H), 6.89 (1H, dd, J 8.8 and 2.2 Hz, Ph-5H), 6.67 (1H, d, J 2.2 Hz, Ph-3H), 3.87 (3H, s, J 6.9, O—CH$_3$), 2.38 (3H, s, Ac-2H$_3$). $^{13}$C NMR (125 MHz, CDCl$_3$): δ 187.4 (Formyl-C), 169.0 (Ac—C1), 165.2 (Ph-C4), 153.2 (Ph-C2), 133.4 (Ph-C6), 121.7 (Ph-C1), 112.7 (Ph-C5), 108.9 (Ph-C3), 55.9 (O—CH$_3$), 20.7 (Ac—C2). HRMS (ESI): C$_{10}$H$_{11}$O$_4$[M+H]$^+$; Requires: 195,0652. Found: 195,0651.

Example 1-3: Preparation of 2,3-Diacetoxy Benzaldehyde, 1-3

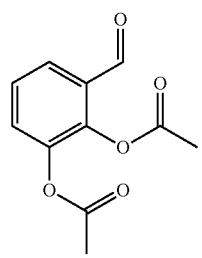 [SMILES: CC(=O)Oc1cccc(C=O)c1OC(C)=O]

By General Procedure B, using 2,3-dihydroxy benzaldehyde (552 mg, 4 mmol). Pale yellow amorphous solid (732 mg, 3.29 mmol, 82%). $^1$H NMR (500 MHz, CDCl$_3$): δ 10.06 (1H, s, CHO), 7.75 (1H, dd, J 7.6 and 1.9 Hz, Ph-6H), 7.46

(1H, dd, J 8.1 and 1.9 Hz, Ph-4H), 7.41 (1H, app t, J 7.6 Hz, Ph-5H), 2.38 (3H, s, 2-OAc—CH₃), 2.31 (3H, s, 2-OAc—CH₃). HRMS (ESI): C₁₁H₁₀O₅Na [M+Na]⁺; Requires: 245.0420. Found: 245.0421.

Example 1-4: Preparation of 2-mercaptobenzaldehyde, 1-4

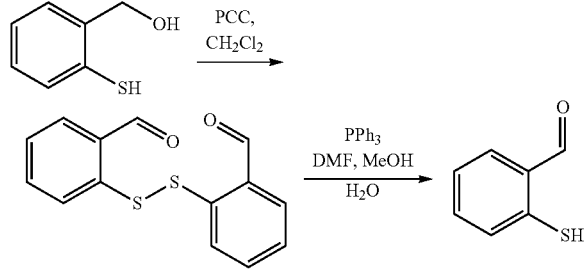

By the method of Chun Ling Tung et al. (Organic & Biomolecular Chemistry 2015, 13 (25), 6922), 2-mercaptobenzyl alcohol (3.0 g, 21.5 mmol) was added as a solution in CH₂Cl₂ (10 mL) to a stirred suspension of pyridinium chlorochromate in CH₂Cl₂ (50 mL) and the reaction mixture was stirred at r.t. After 4 h, the reaction mixture was filtered through a celite pad, eluting with CH₂Cl₂ (5×10 mL), the filtrate collected and concentrated in vacuo to give a crude product. The crude was diluted in DMF (50 mL) and MeOH (50 mL) and H₂O (30 mL) were added. Triphenylphosphine (8.4 g, 32.1 mmol), was added to the solution and the reaction mixture was stirred at r.t. After 30 min, the reaction mixture was cooled to 0° C., and stirred. After 30 min, H₂O (50 mL) and Et₂O (100 mL) were added and layers separated. The organic layer was washed with H₂O (3×50 mL) and sat. NaCl (2×50 mL), dried over Na₂SO₄, filtered and concentrated in vacuo to give a crude product. Purification by flash chromatography eluting with 10% EtOAc in Petroleum Ether (R$_f$=0.32, 90:10 Petrol-EtOAc) gave the title compound as a colourless liquid (2.01 g, 14.6 mmol, 68% over two steps). ¹H NMR (500 MHz, CDCl₃, matching previously reported[1]): δ 10.04 (1H, s, CHO), 7.71 (1H, dd, J 7.4 and 1.8 Hz, Ph-6H), 7.32-7.22 (3H, m, Ph-4H, Ph-3H and Ph-2H).

Example 1-5: Preparation of Ethanethioic Acid, S-(2-formylphenyl) ester, 1-5

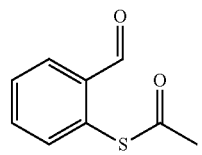

By General Procedure B, using 2-mercaptobenzaldehyde (800 mg, 5.8 mmol). Pale yellow amorphous solid (855 mg, 4.75 mmol, 82%). ¹H NMR (500 MHz, CDCl₃): δ 10.26 (1H, s, CHO), 8.06 (1H, dd, J 7.7 and 1.6 Hz, Ph-6H), 7.65 (1H, app dt, J 7.7 and 1.6 Hz, Ph-6H), 7.60 (1H, app t, J 7.7, Ph-4H), 7.52 (1H, dd, J 7.7 and 1.2 Hz, Ph-3H), 2.50 (3H, s, S—Ac—CH₃). ¹³C NMR (125 MHz, CDCl₃): δ 192.5 (S—Ac—C1), 190.8 (CHO), 136.7 (Ph-C1), 136.5 (Ph-C6), 134.2 (Ph-C5), 131.0 (Ph-C2), 130.4 (Ph-C4), 129.2 (Ph-C3), 30.4 (S—Ac—C2). LCMS: MH⁺ 181.2.

Example 2-1: Preparation of Methyl 3-ureidobenzoate, 2-1

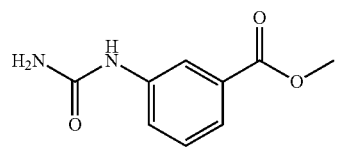

By General Procedure A, using methyl 3-amino benzoate (1.51 g, 10 mmol). Colourless amorphous solid (1.66 g, 8.55 mmol, 86%). ¹H NMR (500 MHz, MeOD): δ 8.07 (1H, t, J 2.0 Hz, Ph-2H), 7.67-7.63 (2H, m, Ph-4H and Ph-6H), 7.38 (1H, app t, J 7.9 Hz, Ph-5H), 3.91 (3H, s, CO2CH₃). ¹³C NMR (125 MHz, MeOD): δ167.1 (CO₂CH₃), 157.8 (NH₂CONH), 140.0 (Ph-C1), 130.5 (Ph-C3), 128.6 (Ph-C5), 123.2 (Ph-C4 or Ph-C6), 123.0 (Ph-C6 or Ph-C4), 119.5 (Ph-C2), 51.2 (CH₃). HRMS (ESI): C₉H₁₀O₃N₂Na [M+Na]⁺; Requires: 217.0584. Found: 217.0586.

Example 2-2: Preparation of N-(4-Methylphenethyl)-3-ureidobenzamide, 2-2

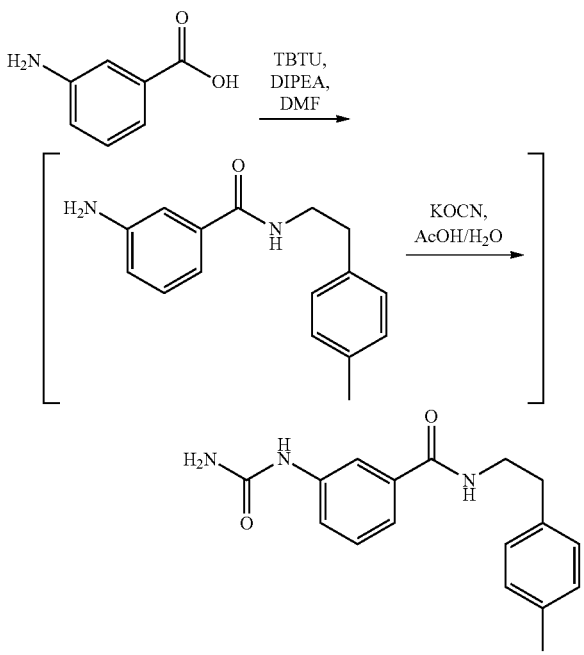

By General Procedure F, using 3-amino benzoate (1.1 g, 8 mmol, 1.6 equiv.) and 2-(p-Tolyl)-ethylamine (727 μL, 5 mmol, 1 equiv.), followed by General Procedure A, requiring no further purification. Colourless amorphous solid (1.33 g, 4.5 mmol, 90% over two steps). ¹H NMR (500 MHz, MeOD, NH not observed): δ 7.78 (1H, s, Bn-2H), 7.54 (1H, d, J 7.8 Hz, Bn-4H), 7.38 (1H, d, J 8.2 Hz, Bn-6H), 7.43 (1H, app t, J 7.9 Hz, Bn-5H), 7.18-7.09 (4H, m, Ph-2H and Ph-3H), 3.61-3.54 (2H, m, N-Et-1H₂), 2.91-2.85 (2H, m, N-Et-2H$_2$), 2.31 (3H, s, Ph-4-CH$_3$). $^{13}$C NMR (125 MHz, MeOD): δ 168.9 (CONH), 158.8 (NH$_2$CONH), 139.8 (Bn-C1), 136.1 (Ph-C4), 135.5 (Ph-C1), 135.2 (Bn-C3), 128.7 (Ph-C2), 128.6 (Ph-C3), 128.4 (Bn-C5), 121.8 (Bn-C4), 120.8 (Bn-C6), 117.7 (Bn-C2), 41.4 (N-Et-C1), 31.8 (N-Et-C2), 19.3 (Ph-4-CH$_3$). HRMS (ESI): C$_{17}$H$_{20}$N$_3$O$_2$ [M+H]$^+$; Requires: 298.1550. Found: 298.1556.

Example 2-3: Preparation of Methyl 3-thioureidobenzoate, 2-3

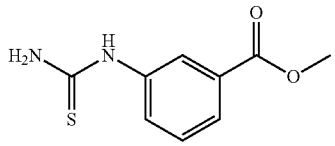

By General Procedure A, using methyl 3-amino benzoate (756 g, 5 mmol) and KSCN (1.95 g, 20 mmol), heated to 80° C. for 72 h. Cooled to 0° C. Colourless amorphous solid (503 mg, 2.4 mmol, 48%). $^1$H NMR (500 MHz, MeOD): δ8.02 (1H, t, J 1.8 Hz, Bn-2H), 7.84 (1H, ddd, J 7.7, 1.6 and 2.1 Hz, Bn-4H), 7.64 (1H, ddd, J 8.0, 1.6 and 2.1 Hz, Bn-4H), 7.38 (1H, app t, J 7.9 Hz, Ph-5H), 3.91 (3H, s, CO$_2$CH$_3$). $^{13}$C NMR (125 MHz, MeOD): δ181.6 (NH$_2$CONH), 167.1 (CO$_2$CH$_3$), 140.0 (Ph-C1), 130.5 (Ph-C3), 128.6 (Ph-C5), 123.2 (Ph-C4 or Ph-C6), 123.0 (Ph-C6 or Ph-C4), 119.5 (Ph-C2), 51.2 (CH$_3$). HRMS (ESI): C$_9$H$_{11}$N$_2$O$_2$S [M+H]$^+$; Requires: 211.0536. Found: 211.0536.

Example 2-4: Preparation of N-(4-Methylphenethyl)-3-thioureidobenzamide, 2-4

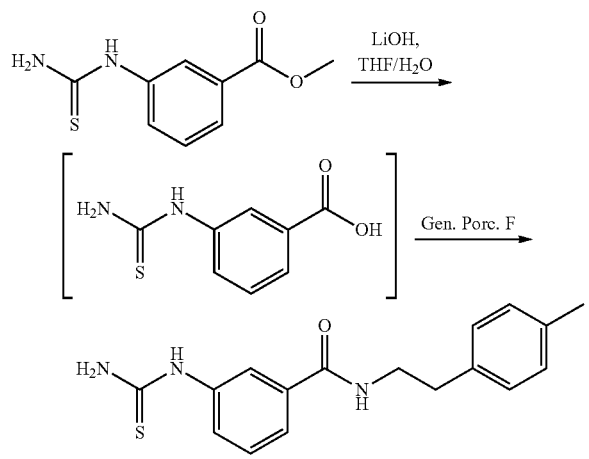

Lithium hydroxide (360 mg, 15 mmol), was added to a stirred solution of the ester 2-3 (201 mg, 1 mmol), in THF—H$_2$O (1:1, 10 mL, 0.1 M) at r.t. After 19 h, the reaction mixture was concentrated in vacuo to remove the THF and acidified to pH=0-1 by slow addition of 1 M aq. HCl solution and the crude mixture was lyophilized. The crude was diluted with DMF (2.5 mL, 0.4 M) and by General Procedure F, followed by purification by flash chromatography, eluting with 2-4% MeOH in CH$_2$Cl$_2$ (R$_f$=0.31, 95:5 CH$_2$Cl$_2$-MeOH). Colourless amorphous solid (350 mg, 0.88 mmol, 73%). $^1$H NMR (500 MHz, MeOD, NHs not observed): δ 7.71 (1H, app s, Bn-2H), 7.57 (1H, d, J 7.9 Hz, Bn-4H), 7.50 (1H, d, J 8.1 Hz, Bn-6H), 7.43 (1H, app t, J 7.9 Hz, Bn-5H), 7.14-7.06 (4H, m, Ph-2H and Ph-3H), 3.55 (2H, d, J 6.8 Hz, N-Et-1H$_2$), 2.85 (2H, d, J 6.8 Hz, N-Et-2H$_2$), 2.27 (3H, s, Ph-4-CH$_3$). $^{13}$C NMR (125 MHz, MeOD): δ 181.1 (NH$_2$CONH), 168.1 (CONH), 139.8 (Bn-C1), 136.1 (Ph-C4), 135.5 (Ph-C1), 135.2 (Bn-C3), 128.7 (Ph-C2), 128.6 (Ph-C3), 128.4 (Bn-C5), 121.8 (Bn-C4), 120.8 (Bn-C6), 117.7 (Bn-C2), 41.4 (N-Et-C1), 31.8 (N-Et-C2), 21.0 (Ph-4-CH$_3$). HRMS (ESI): C$_{17}$H$_{20}$N$_3$OS [M+H]$^+$; Requires: 314.1322. Found: 314.1322.

Example 2-5: Preparation of 3-(10-Hydroxy-2-methyl-4-oxo-5,6-dihydro-2H-2,6-methanobenzo[g][1,3,5]oxadiazocin-3(4H)-yl)-N-(4-methylphenethyl)benzamide, 2-5

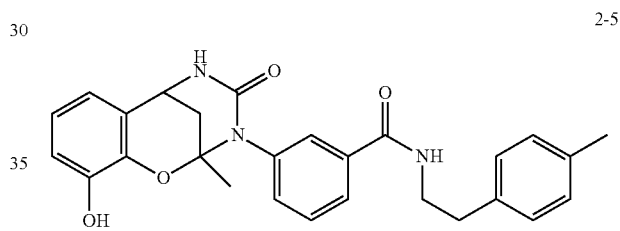

By General Procedure E, using the urea 5 (149 mg, 0.5 mmol), the aldehyde 1-3 (111 mg, 0.5 mmol), methyl acetoacetate (90 μL, 0.75 mmol), and TMSCl (380 μL, 3 mmol), followed by purification by prep-HPLC eluting with 10-100% MeCN in H$_2$O (No TFA). Colourless amorphous solid (122 mg, 0.27 mmol, 53% over four steps). $^1$H NMR (500 MHz, MeOD, NHs not observed): δ 7.63 (1H, dt, J 7.9 and 1.3 Hz, Bn-6H), 7.44 (1H, app s, Bn-2H), 7.38 (1H, app t, J 7.9 Hz, Bn-5H), 7.26 (1H, d, J 7.9 Hz, Bn-4H), 7.03 (2H, d, J 8.0 Hz, Ph-3H), 6.98 (2H, d, J 8.0 Hz, Ph-2H), 6.75-6.71 (2H, m, 8H and 7H), 6.68 (1H, dd, J 7.6 and 1.4 Hz, 9H), 4.32 (1H, t, J 3.0 Hz, 6H), 3.49-3.43 (2H, m, N-Et-1H$_2$), 2.78-2.74 (2H, m, N-Et-2H$_2$), 2.53 (1H, dd, J 13.3 and 3.0 Hz, g-H$_2^1$), 2.35 (1H, dd, J 13.3 and 3.0 Hz, g-H$_2^1$), 2.18 (3H, s, Ph-4-CH$_3$), 1.40 (3H, s, 2-CH$_3$). $^{13}$C NMR (125 MHz, MeOD): δ168.4 (CONH), 156.7 (C4), 145.8 (C10), 138.7 (C10a), 138.1 (Bn-C1), 136.0 (Ph-C1), 135.5 (Bn-C3), 133.2 (Bn-C4), 128.7 (Ph-C2), 128.5 (Bn-C2), 128.4 (Ph-C3), 126.3 (Bn-C6), 125.8 (C6α), 121.4 (C8), 119.9 (C9), 115.5 (C7), 85.6 (C2), 44.3 (C6), 41.4 (N-Et-C1), 34.7 (Cg), 34.1 (N-Et-C2), 25.6 (2-CH$_3$), 19.7 (Ph-4-CH$_3$). HRMS (ESI): C$_{27}$H$_{28}$N$_3$O$_4$ [M+H]$^+$; Requires: 458.2074. Found: 458.2082.

Example 2-6: Synthesis of 3-(10-(benzyloxy)-2-methyl-4-oxo-5,6-dihydro-2H-2,6-methanobenzo[g][1,3,5]oxadiazocin-3(4H)-yl)benzoic Acid, 2-6

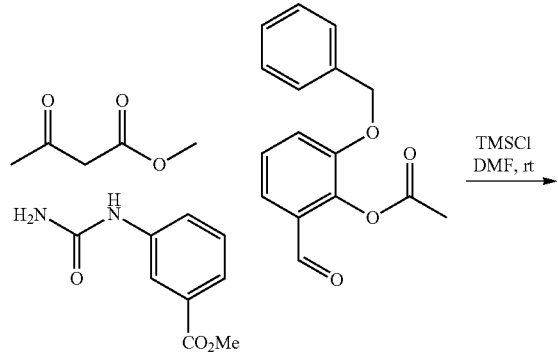

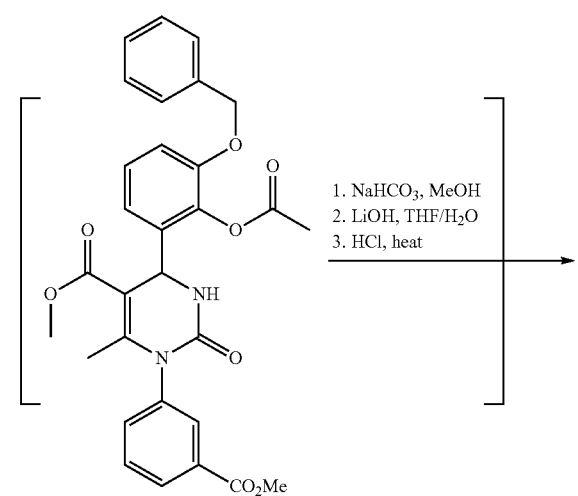

According to general Procedure E, starting with 2-(benzyloxy)-6-formylphenyl acetate and methyl 3-ureidobenzoate 2-1, the carboxylic acid 2-6 was obtained. C25H22N2O5, Exact Mass: 430.15, LCMS [M+H]+ 431.3.

Example 3-1: Preparation of 3-(10-(Benzyloxy)-2-methyl-4-oxo-5,6-dihydro-2H-2,6-methanobenzo[g][1,3,5]oxadiazocin-3(4H)-yl)-N-(4-methylphenethyl)benzamide, Compound A01

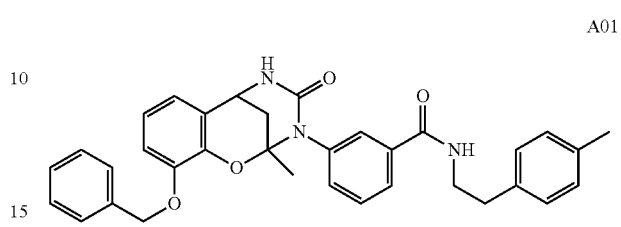

By General Procedure G, using the phenol 2-5 (46 mg, 0.1 mmol) and benzyl bromide (12 µL, 0.1 mmol) followed by purification by prep-HPLC eluting with 10-100% MeCN in H$_2$O (0.1% TFA). Colourless amorphous solid (41 mg, 0.07 mmol, 75%). $^1$H NMR (500 MHz, CDCl$_3$): δ 7.80 (1H, app s, Bn-6H), 7.56 (1H, app s, Bn-2H), 7.48-7.42 (4H, m, Bn-5H, 10-CH$_2$Ph-4H and 10-CH$_2$Ph-3H), 7.50 (2H, app t, J 7.5 Hz, 10-CH$_2$Ph-2H), 7.33 (1H, app t, J 7.7 Hz, Bn-4H) 7.12 (2H, d, J 8.0 Hz, Ph-3H), 7.08 (2H, d, J 8.0 Hz, Ph-2H), 6.94-6.89 (2H, m, 7H and 8H), 6.84 (1H, app d, J 7.4 Hz, 9H), 5.17 (1H, d, J 12.0 Hz, 10-CH$_2$$^1$), 5.10 (1H, d, J 12.0 Hz, 10-CH$_2$$^1$), 4.40 (1H, t, J 2.9 Hz, 6H), 3.61-3.55 (2H, m, N-Et-1H$_2$), 2.80-2.73 (2H, m, N-Et-2H$_2$), 2.68 (1H, dd, J 13.1 and 2.9 Hz, g-H$_2$$^1$), 2.50 (1H, dd, J 13.1 and 2.9 Hz, g-H$_2$$^1$), 2.34 (3H, s, Ph-4-CH$_3$), 1.55 (3H, s, 2-CH$_3$). $^{13}$C NMR (125 MHz, CDCl$_3$): δ 166.7 (CONH), 155.9 (C4), 147.9 (C10), 141.4 (C10a), 138.0 (Bn-C1), 137.0 (10-CH$_2$Ph-C1), 135.9 (Ph-C1), 135.4 (Bn-C3), 133.1 (Bn-C4), 129.4 (Bn-C2), 129.2 (10-CH$_2$Ph-C4), 129.1 (Ph-C2), 128.8 (Ph-C3 and 10-CH$_2$Ph-C1), 128.6 (10-CH$_2$Ph-C3), 128.0 (10-CH$_2$Ph-C2), 127.1 (Bn-C6), 125.7 (C6α), 121.7 (C8), 120.5 (C9), 85.6 (C2), 71.6 (10-CH$_2$Ph), 45.3 (C6), 41.4 (N-Et-C1), 35.2 (N-Et-C2), 34.6 (Cg), 27.1 (2-CH$_3$), 21.1 (Ph-4-CH$_3$). HRMS (ESI): C$_{34}$H$_{34}$N$_3$O$_4$ [M+H]$^+$; Requires: 548.2544. Found: 548.2535.

Example 3-2: Preparation of 3-(2-Methyl-10-((2-methylbenzyl)oxy)-4-oxo-5,6-dihydro-2H-2,6-methanobenzo[g][1,3,5]oxadiazocin-3(4H)-yl)-N-(4-methylphenethyl)benzamide, Compound A02

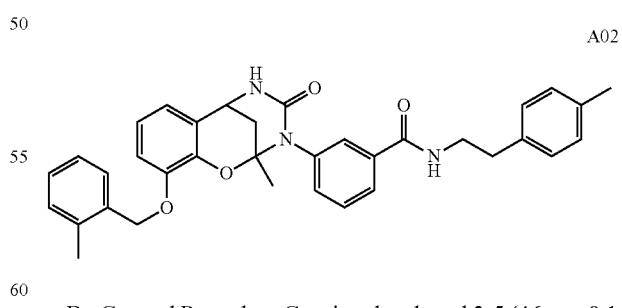

By General Procedure G, using the phenol 2-5 (46 mg, 0.1 mmol) and 2-methylbenzyl bromide (14 µL, 0.1 mmol) followed by purification by prep-HPLC eluting with 10-100% MeCN in H$_2$O (no TFA). Colourless amorphous solid (46 mg, 0.08 mmol, 82%). $^1$H NMR (500 MHz, CDCl$_3$): δ 7.81 (1H, app s, Bn-6H), 7.52 (1H, app s, Bn-2H), 7.46-7.42 (2H, m, Bn-5H and Bn-4H) 7.26 (2H, d, J 7.2 Hz, 10-O—CH$_2$-Ph-6H), 7.23-7.20 (2H, m, 10-O—CH$_2$-Ph-4H, and -Ph-5H), 7.16 (1H, d, J 7.2 Hz, 10-O—CH$_2$-Ph-3H), 7.12 (2H, d, J 8.2 Hz, Ph-3H), 7.09-7.05 (2H, m, Ph-2H), 6.99 (1H, d, J, 7.8 Hz, 7H), 6.95 (1H, app t, J 7.8 Hz, 8H), 6.89 (1H, d, J 7.8 Hz, 9H), 5.16 (1H, d, J 12.1 Hz, 10-O—CH$_2^1$), 5.06 (1H, d, J 12.1 Hz, 10-O—CH$_2^1$), 4.45 (1H, app s, 6H), 3.63-3.52 (2H, m, N-Et-1H$_2$), 2.83-2.71 (2H, m, N-Et-2H$_2$), 2.69 (1H, d, J 13.1 Hz, g-H$_2^1$), 2.51 (1H, d, J 13.1 Hz, g-H$_2^1$), 2.40 (10-O—CH$_2$-Ph-2-CH$_3$), 2.35 (3H, s, Ph-4-CH$_3$), 1.54 (3H, s, 2-CH$_3$). $^{13}$C NMR (125 MHz, CDCl$_3$): δ 166.6 (CONH, verified through HMBC), 156.2 (C4), 147.9 (C10), 137.6 (Bn-C1), 136.3 (10-O—CH$_2$-Ph-C3), 135.7 (Ph-C4), 134.8 (Bn-C3), 133.1 (Bn-C4, verified via HMBC), 130.4 (10-O—CH$_2$-Ph-C6), 129.4 (Ph-C2), 129.3 (10-O—CH$_2$-Ph-C2), 129.1 (Bn-C2), 128.7 (Bn-C5), 128.6 (Ph-C3), 128.3 (10-O—CH$_2$-Ph-C4), 128.2 (10-O—CH$_2$-Ph-C5), 126.1 (Bn-C6), 125.5 (10-O—CH$_2$-Ph-C1), 121.9 (C9), 96.1 (C7), 85.6 (C2), 66.1 (10-O—CH$_2$ verified through HSQC), 45.2 (C6), 41.3 (N-Et-C1), 35.2 (N-Et-C2), 34.6 (Cg), 27.0 (2-CH$_3$), 21.0 (Ph-4-CH$_3$), 18.9 (10-O—CH$_2$-Ph-2-CH$_3$). HRMS (ESI): C$_{35}$H$_{36}$N$_3$O$_4$ [M+H]$^+$; Requires: 562.2700. Found: 562.2694.

Example 3-3: Preparation of 3-(2-Methyl-10-((4-nitrobenzyl)oxy)-4-oxo-5,6-dihydro-2H-2,6-methanobenzo[g][1,3,5]oxadiazocin-3(4H)-yl)-N-(4-methylphenethyl)benzamide, Compound A03

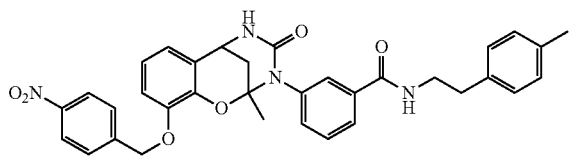

A03

By General Procedure G, using the phenol 2-5 (46 mg, 0.1 mmol) and 4-nitro benzyl bromide (22 mg, 0.1 mmol) followed by purification by prep-HPLC eluting with 10-100% MeCN in H$_2$O (0.1% TFA). Colourless amorphous solid (TFA salt, 46 mg, 0.08 mmol, 77%). $^1$H NMR (500 MHz, CDCl$_3$): δ 8.26 (2H, d, J 8.0 Hz, 10-O—CH$_2$-Ph-3H), 7.69-7.64 (3H, m, Bn-6H and 10-O—CH$_2$-Ph-2H), 7.43-7.40 (2H, m, Bn-2H and Bn-5H), 7.18-7.08 (5H, m, Bn-4H, Ph-3H and Ph-2H), 6.95-6.86 (3H, m, 7H, 8H and 9H), 5.27 (1H, d, J 12.6 Hz, 10-O—CH$_2^1$), 5.24 (1H, d, J 12.6 Hz, 10-O—CH$_2^1$), 4.44 (1H, app s, 6H), 3.71-3.63 (2H, m, N-Et-1H$_2$), 2.86-2.80 (2H, m, N-Et-2H$_2$), 2.68 (1H, d, J 13.4 Hz, g-H$_2^1$), 2.49 (1H, d, J 13.4 Hz, g-H$_2^1$), 2.35 (3H, s, Ph-4-CH$_3$), 1.51 (3H, s, 2-CH$_3$). $^{13}$C NMR (125 MHz, CDCl$_3$): δ 166.7 (CONH), 156.1 (C4), 147.8 (C10), 147.4 (10-O—CH$_2$-Ph-C4), 141.3 (C10a), 137.9 (Bn-C1), 136.1 (Ph-C4), 135.6 (Ph-C1), 133.1 (Bn-C3, verified through HSQC), 129.4 (Ph-C2), 129.0 (Bn-C2), 128.6 (Bn-C5), 127.4 (Ph-C3), 126.3 (10-O—CH$_2$-Ph-C3), 125.7 (10-O—CH$_2$-Ph-C2), 125.6 (Bn-C6), 123.8 (10-O—CH$_2$-Ph-C1), 121.8 (C9) 115.5 (C8), 112.0 (C7), 85.6 (C2), 70.2 (10-O—CH$_2$), 45.1 (C6), 41.4 (N-Et-C1), 35.2 (N-Et-C2), 34.5 (Cg), 27.1 (2-CH$_3$), 21.0 (Ph-4-CH$_3$). HRMS (ESI): C$_{34}$H$_{33}$N$_4$O$_6$ [M+H]$^+$; Requires: 593.2395. Found: 593.2378.

Example 3-4: Preparation of 3-(10-((3-Chlorobenzyl)oxy)-2-methyl-4-oxo-5,6-dihydro-2H-2,6-methanobenzo[g][1,3,5]oxadiazocin-3(4H)-yl)-N-(4-methylphenethyl)benzamide, Compound A04

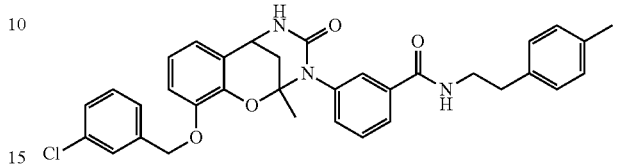

A04

By General Procedure G, using the phenol 2-5 (46 mg, 0.1 mmol) and 3-chlorobenzyl bromide (13 μL, 0.1 mmol) followed by purification by prep-HPLC eluting with 10-100% MeCN in H$_2$O (0.1% TFA). Colourless amorphous solid (TFA salt, 42 mg, 0.07 mmol, 72%). $^1$H NMR (500 MHz, CDCl$_3$): δ 7.77 (1H, app s, Bn-6H), 7.57 (1H, app s, Bn-2H), 7.49-7.45 (2H, m, Bn-5H and Bn-4H) 7.34-7.30 (3H, m, 10-O—CH$_2$-Ph-4H, -Ph-5H, and -Ph-6H), 7.21-7.19 (1H, app d, J 2.5 Hz, 10-O—CH$_2$-Ph-2H), 7.14-7.09 (4H, m, Ph-3H and Ph-2H), 6.96-6.90 (2H, m, 7H and 8H), 6.87 (1H, d, J 7.1 Hz, 9H), 5.13 (1H, d, J 12.9 Hz, 10-O—CH$_2^1$), 5.09 (1H, d, J 12.9 Hz, 10-O—CH$_2^1$), 4.42 (1H, app s, 6H), 3.68-3.60 (2H, m, N-Et-1H$_2$), 2.85-2.77 (2H, m, N-Et-2H$_2$), 2.69 (1H, d, J 13.2 Hz, g-H$_2^1$), 2.50 (1H, d, J 13.2 Hz, g-H$_2^1$), 2.35 (3H, s, Ph-4-CH$_3$), 1.56 (3H, s, 2-CH$_3$). $^{13}$C NMR (125 MHz, CDCl$_3$): δ 167.9 (CONH), 155.9 (C4), 147.7 (C10), 141.5 (10-O—CH$_2$-Ph-C1), 140.4 (C10a), 139.1 (10-O—CH$_2$-Ph-C3), 137.8 (Bn-C1), 135.9 (Ph-C4), 135.5 (Ph-C1), 134.5 (Bn-C3), 133.1 (Bn-C4), 129.9 (Ph-C2), 129.3 (10-O—CH$_2$-Ph-C5), 129.1 (Bn-C2), 128.7 (Bn-C5), 128.1 (Ph-C3), 127.2 (10-O—CH$_2$-Ph-C4), 126.8 (10-O—CH$_2$-Ph-C6), 126.6 (Bn-C6), 125.0 (10-O—CH$_2$-Ph-C5), 121.8 (C9 and C8), 115.0 (C7), 85.6 (C2), 66.1 (10-O—CH$_2$ verified through HSQC), 45.2 (C6), 41.4 (N-Et-C1), 35.2 (N-Et-C2), 34.6 (Cg), 27.1 (2-CH$_3$), 21.0 (Ph-4-CH$_3$). HRMS (ESI): C$_{34}$H$_{33}$ClN$_3$O$_4$[M+H]$^+$; Requires: 582.2154. Found: 582.2155.

Example 3-5: Preparation of 3-(10-((4-Cyanobenzyl)oxy)-2-methyl-4-oxo-5,6-dihydro-2H-2,6-methanobenzo[g][1,3,5]oxadiazocin-3(4H)-yl)-N-(4-methylphenethyl)benzamide, Compound A05

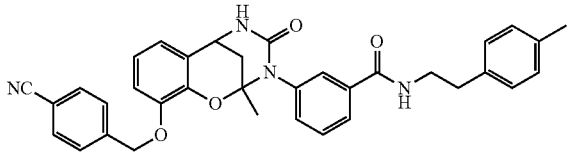

A05

By General Procedure G, using the phenol 2-5 (46 mg, 0.1 mmol) and 4-chloromethyl benzonitrile (15 mg, 0.1 mmol) followed by purification by prep-HPLC eluting with 10-100% MeCN in H$_2$O (No TFA). Colourless amorphous solid (44 mg, 0.08 mmol, 77%). $^1$H NMR (500 MHz, CDCl$_3$): δ 7.71-7.68 (3H, m, 10-O—CH$_2$-Ph-3H and Bn-6H), 7.63 (1H, app s, Bn-2H), 7.59 (2H, d, J 8.1 Hz, 10-O—CH$_2$-Ph-2H), 7.43-7.40 (2H, m, Bn-4H and Bn-5H), 7.14 (2H, d, J 7.6 Hz, Ph-3H) 7.11 (2H, d, J 7.6 Hz, Ph-2H), 6.93 (1H, app t, J 8.1 Hz, 8H), 6.88 (2H, app d, J 7.6 Hz, 7H and 9H), 5.23-5.19 (2H, m, 10-O—CH$_2$), 4.45 (1H, app s, 6H), 3.65-3.57 (2H, m, N-Et-1H$_2$), 2.85-2.80 (2H, m, N-Et-2H$_2$), 2.69 (1H, dd, J 13.1 and 2.4 Hz, g-H$_2^1$), 2.50 (1H, app d, J 13.1 Hz, g-H$_2^1$), 2.35 (3H, s, Ph-4-CH$_3$), 1.55 (3H, s, 2-CH$_3$). $^{13}$C NMR (125 MHz, CDCl$_3$): δ 166.7 (CONH), 156.2 (C4), 147.5 (C10), 142.6 (10-O—CH$_2$-Ph-C1), 141.3 (C10a), 137.7 (Bn-C1), 136.1 (Ph-C4), 135.7 (Ph-C1), 133.1 (Bn-C3, verified through HSQC), 132.4 (10-O—CH$_2$-Ph-C3), 129.4 (Ph-C2), 129.0 (Bn-C2), 128.7 (Ph-C3 and Bn-C5), 127.3 (10-O—CH$_2$-Ph-C2), 126.4 (10-O—CH$_2$-Ph-C4), 125.6 (Bn-C6), 121.8 (C9) 118.6 (C8), 115.2 (C7), 111.2 (CN), 85.6 (C2), 70.4 (10-O—CH$_2$), 45.1 (C6), 41.4 (N-Et-C1), 35.2 (N-Et-C2), 34.5 (Cg), 27.1 (2-CH$_3$), 21.0 (Ph-4-CH$_3$). HRMS (ESI): C$_{35}$H$_{33}$N$_4$O$_4$ [M+H]$^+$; Requires: 573.2496. Found: 573.2489.

Example 3-6: Preparation of 3-(10-((4-(tert-Butyl)benzyl)oxy)-2-methyl-4-oxo-5,6-dihydro-2H-2,6-methanobenzo[g][1,3,5]oxadiazocin-3(4H)-yl)-N-(4-methylphenethyl)benzamide, Compound A06

A06

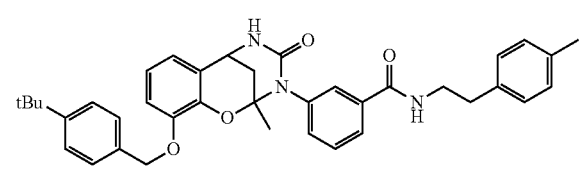

By General Procedure G, using the phenol 2-5 (46 mg, 0.1 mmol) and 4-tert-butyl benzyl bromide (18 µL, 0.1 mmol) followed by purification by prep-HPLC eluting with 10-100% MeCN in H$_2$O (0.1% TFA). Colourless amorphous solid (TFA salt, 41 mg, 0.07 mmol, 68%). $^1$H NMR (500 MHz, CDCl$_3$): δ 7.81 (1H, app s, Bn-6H), 7.55 (1H, app s, Bn-2H), 7.44 (1H, app s, Bn-5H), 7.41-7.38 (3H, m, Bn-4H and 10-O—CH$_2$-Ph-3H), 7.36-7.32 (2H, m, 10-O—CH$_2$-Ph-2H), 7.16-7.06 (4H, m, Ph-3H and Ph-2H), 6.95 (1H, app d, J 7.9 Hz, 7H), 6.91 (1H, app t, J 7.5 Hz, 8H), 6.85 (1H, d, J 7.5 Hz, 9H), 5.15 (1H, d, J 12.1 Hz, 10-O—CH$_2^1$), 5.06 (1H, d, J 12.1 Hz, 10-O—CH$_2^1$), 4.42 (1H, app s, 6H), 3.61-3.53 (2H, m, N-Et-1H$_2$), 2.82-2.70 (2H, m, N-Et-2H$_2$), 2.65 (1H, d, J 12.7 Hz, g-H$_2^1$), 2.49 (1H, d, J 12.7 Hz, g-H$_2^1$), 2.34 (3H, s, Ph-4-CH$_3$), 1.54 (3H, s, 2-CH$_3$) 1.34 (9H, s, tBu-(CH$_3$)$_3$). $^{13}$C NMR (125 MHz, CDCl$_3$): δ 166.7 (CONH), 156.3 (C4), 151.6 (10-O—CH$_2$-Ph-C4), 151.1 (10-O—CH$_2$-Ph-C1), 148.8 (C10), 141.4 (C10a), 137.6 (Bn-C1), 135.9 (Ph-C4), 135.5 (Ph-C1), 134.7 (Bn-C3), 131.1 (Bn-C4), 129.3 (Ph-C2), 129.1 (Bn-C2), 128.8 (Bn-C5), 128.7 (Ph-C3), 126.8 (10-O—CH$_2$-Ph-C3), 125.8 (10-O—CH$_2$-Ph-C2), 125.6 (Bn-C6), 121.8 (C9 and C8), 118.7 (C7), 85.2 (C2), 65.2 (10-O—CH$_2$), 45.1 (C6), 41.4 (N-Et-C1), 35.2 (N-Et-C2), 34.6 (Cg), 33.6 ($^t$Bu-C), 31.3 ($^t$Bu-(CH$_3$)$_3$), 27.0 (2-CH$_3$), 21.0 (Ph-4-CH$_3$). HRMS (ESI): C$_{38}$H$_{42}$N$_3$O$_4$ [M+H]$^+$; Requires: 604.3170. Found: 604.3157.

Example 3-7: Preparation of 3-(10-(Furan-2-ylmethoxy)-2-methyl-4-oxo-5,6-dihydro-2H-2,6-methanobenzo[g][1,3,5]oxadiazocin-3(4H)-yl)-N-(4-methylphenethyl)benzamide, Compound A07

A07

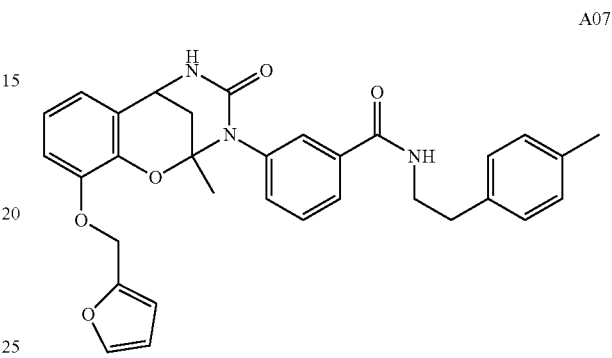

Methanesulfonyl chloride (93 µL, 1.2 mmol) was added to a stirred solution of furfuryl alcohol (87 µL, 1 mmol) and trimethylamine (225 µL, 2 mmol) in CH$_2$Cl$_2$ (10 mL, 0.1 M) cooled to 0° C. and the reaction mixture was allowed to warm to r.t. After 19 h, the reaction mixture was diluted with CH$_2$Cl$_2$ (10 mL) and 1 M aqueous HCl solution (20 mL) was added. Layers were separated and the aqueous layer was extracted with CH$_2$Cl$_2$ (3×10 mL). The combined organic layers were dried over Na$_2$SO$_4$, filtered and concentrated in vacuo to give a crude product. Followed by General Procedure G, using the phenol 52 (46 mg, 0.1 mmol) and the crude furfuryl methanesulfonate (20 mg) followed by purification by prep-HPLC eluting with 10-100% MeCN in H$_2$O (0.1% TFA). Colourless amorphous solid (34 mg, 0.06 mmol, 64%). $^1$H NMR (500 MHz, CDCl$_3$): δ 7.83 (1H, s, Bn-6H), 7.51 (1H, app s, Bn-2H), 7.46 (1H, app t, J 7.5 Hz, Bn-5H), 7.44-7.40 (2H, m, Bn-4H and Furan-5H), 7.16-7.11 (4H, m, Ph-3H and Ph-2H), 6.99 (1H, app d, J 8.2 Hz, 7H), 6.92 (1H, app t, J 7.9 Hz, 8H), 6.87 (1H, d, J 7.4 Hz, 9H), 6.41 (1H, app s, Furan-3H), 6.38 (1H, app s, Furan-4H), 5.11 (2H, d, J 13.0 Hz, 10-O—CH$_2^1$), 5.02 (2H, d, J 13.0 Hz, 10-O—CH$_2^1$), 4.40 (1H, app s, 6H), 3.73-3.60 (2H, m, N-Et-1H$_2$), 2.89-2.82 (2H, m, N-Et-2H$_2$), 2.66 (1H, d, J 12.9 Hz, g-H$_2^1$), 2.48 (1H, d, J 12.9 Hz, g-H$_2^1$), 2.35 (3H, s, Ph-4-CH$_3$), 1.52 (3H, s, 2-CH$_3$). $^{13}$C NMR (125 MHz, CDCl$_3$): δ 166.8 (CONH), 156.0 (C4), 150.4 (Furan-C2), 147.3 (C10), 143.1 (Furan-C5), 141.9 (C10a), 137.7 (Bn-C1), 136.0 (Ph-C4), 135.9 (Ph-C1), 135.4 (Bn-C3), 133.1 (Bn-C4), 129.3 (Ph-C2), 129.1 (Bn-C2), 128.7 (Ph-C3), 127.1 (Bn-C5), 125.7 (Bn-C6), 122.0 (C9), 121.7 (C8), 110.6 (C7), 110.2 (Furan-C3 and Furan C4), 85.6 (C2), 64.6 (10-O—CH$_2$), 45.2 (C6), 41.5 (N-Et-C1), 35.3 (N-Et-C2), 34.7 (Cg), 27.0 (2-CH$_3$), 21.0 (Ph-4-CH$_3$). HRMS (ESI): C$_{32}$H$_{32}$N$_3$O$_5$ [M+H]$^+$; Requires: 538.2336. Found: 538.2345.

Example 3-8: Preparation of 3-(10-(Cyclopropyl-methoxy)-2-methyl-4-oxo-5,6-dihydro-2H-2,6-methanobenzo[g][1,3,5]oxadiazocin-3(4H)-yl)-N-(4-methylphenethyl)benzamide, Compound A08

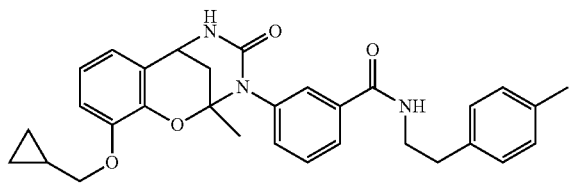

A08

By General Procedure G, using the phenol 2-5 (46 mg, 0.1 mmol) and 1-(bromomethyl)cyclopropane (11 µL, 0.1 mmol) followed by purification by prep-HPLC eluting with 10-100% MeCN in H$_2$O (0.1% TFA). Colourless amorphous solid (41 mg, 0.07 mmol, 75%). $^1$H NMR (500 MHz, CDCl$_3$): δ 7.69 (1H, app s, Bn-6H), 7.41 (1H, app s, Bn-2H), 7.38-7.34 (2H, m, Bn-5H and Bn-4H), 7.07-7.02 (4H, m, Ph-3H and Ph-2H), 6.85-6.82 (2H, m, 7H and 8H), 6.74 (1H, app s, 9H), 4.31 (1H, d, J 2.8 Hz, 6H), 3.86-3.78 (2H, m, 10-CH$_2$), 3.68-3.62 (1H, m, N-Et-1H$_2$$^1$), 3.54-3.49 (1H, m, N-Et-1H$_2$$^1$), 2.81 (2H, app t, J 7.4 Hz, N-Et-2H$_2$), 2.56 (1H, dd, J 12.8 and 2.8 Hz, g-H$_2$$^1$), 2.40 (1H, dd, J 12.8 and 2.8 Hz, g-H$_2$$^1$), 2.26 (3H, s, Ph-4-CH$_3$), 1.43 (3H, s, 2-CH$_3$), 1.24-1.20 (cyclopropyl-1H), 0.57-0.51 (2H, m, cyclopropyl-2H2' and cyclopropyl-2'H$_2$$^1$), 0.30-0.25 (2H, m, cyclopropyl-2H2' and cyclopropyl-2'H$_2$$^1$). $^{13}$C NMR (125 MHz, CDCl$_3$): δ 166.9 (CONH), 156.3 (C4), 148.1 (C10), 141.5 (C10a), 137.7 (Bn-C1), 136.0 (Ph-C1), 135.9 (Bn-C3), 132.9 (Bn-C4), 129.4 (Bn-C2), 129.1 (Ph-C2), 128.7 (Ph-C3), 128.2 (Ph-C4), 126.9 (Bn-C6), 125.5 (C6α), 121.8 (C8), 120.0 (C9), 111.3 (C7), 85.5 (C2), 74.1 (10-CH$_2$), 45.2 (C6), 41.6 (N-Et-C1), 35.4 (N-Et-C2), 34.6 (Cg), 27.0 (2-CH$_3$), 21.1 (Ph-4-CH$_3$), 10.4 (cyclopropyl-C1), 3.4 (cyclopropyl-C2) 3.3 (cyclopropyl-C2'). HRMS (ESI): C31H34N3O4 [M+H]$^+$; Requires: 512.2544. Found: 512.2558.

Example 3-9: Preparation of 3-(2-Methyl-4-oxo-10-(pyridin-4-ylmethoxy)-5,6-dihydro-2H-2,6-methano-benzo[g][1,3,5]oxadiazocin-3(4H)-yl)-N-(4-methylphenethyl)benzamide, Compound A09

A09

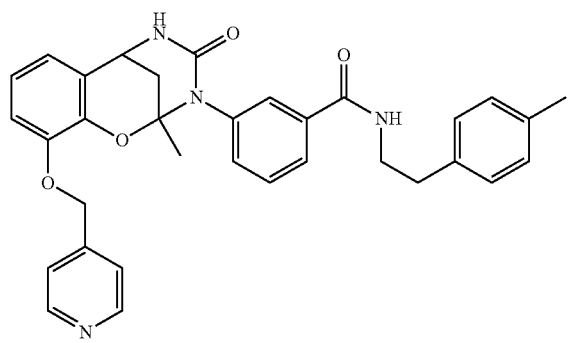

By General Procedure G, using the phenol 52 (46 mg, 0.1 mmol) and 4-chloromethyl pyridine hydrochloride (17 mg, 0.1 mmol) followed by purification by prep-HPLC eluting with 10-100% MeCN in H$_2$O (0.1% TFA). Colourless amorphous solid (TFA salt, 48 mg, 0.09 mmol, 86%). $^1$H NMR (500 MHz, CDCl$_3$): δ 8.69 (2H, d, J 5.6 Hz, Py-2H), 7.90 (2H, app s, Py-3H), 7.62 (1H, app s, Bn-2H), 7.43 (1H, app s, Bn-6H), 7.33-7.26 (2H, m, Bn-5H and Bn-4H), 7.06-7.00 (4H, m, Ph-3H and Ph-2H), 6.89-6.83 (3H, m, 7H, 8H and 9H), 5.38 (1H, d, J 15.3 Hz, 10-O—CH$_2$$^1$), 5.23 (1H, d, J 15.3 Hz, 10-O—CH$_2$$^1$), 4.38 (1H, app t, J 2.9 Hz, 6H), 3.52-3.43 (2H, m, N-Et-1H$_2$), 2.75-2.71 (2H, m, N-Et-2H$_2$), 2.59 (1H, dd, J 13.1 and 2.9 Hz, g-H$_2$$^1$), 2.38 (1H, dd, J 13.1 and 2.9 Hz, g-H$_2$$^1$), 2.25 (3H, s, Ph-4-CH$_3$), 1.43 (3H, s, 2-CH$_3$). $^{13}$C NMR (125 MHz, CDCl$_3$): δ 164.7 (CONH), 154.1 (C4), 144.9 (C10 and Py-C4), 140.8 (Py-C2, and C10a), 139.6 (Bn-C1), 136.2 (Ph-C1), 134.2 (Ph-C4), 133.7 (Bn-C3), 133.6 (Bn-C4), 131.4 (Bn-C5), 127.5 (Bn-C6 and Ph-C2), 126.9 (Bn-C6), 126.7 (Ph-C3), 124.0 (C6α), 123.6 (Bn-C2), 121.7 (Py-C3), 120.7 (C9), 119.9 (C8), 115.4 ( ), 113.1 (C7), 83.7 (C2), 67.4 (10-O—CH$_2$), 42.9 (C6), 39.3 (N-Et-C1), 33.2 (N-Et-C2), 32.3 (Cg), 25.2 (2-CH$_3$), 19.1 (Ph-4-CH$_3$). HRMS (ESI): C$_{33}$H$_{33}$N$_4$O$_4$ [M+H]$^+$; Requires: 549.2496. Found: 549.2487.

Example 3-10: Preparation of 3-(2-Methyl-4-oxo-10-(pyridin-3-ylmethoxy)-5,6-dihydro-2H-2,6-methanobenzo[g][1,3,5]oxadiazocin-3(4H)-yl)-N-(4-methylphenethyl)benzamide, Compound A10

A10

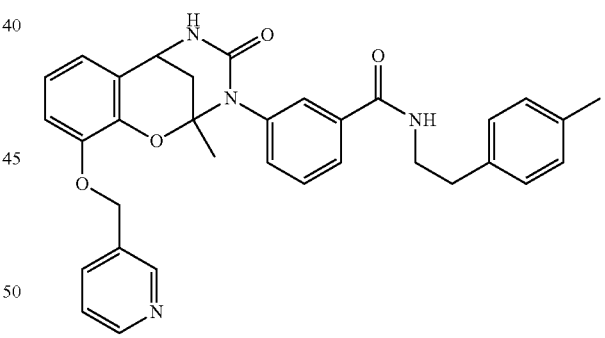

By General Procedure G, using the phenol 2-5 (46 mg, 0.1 mmol) and 3-chloromethyl pyridine hydrochloride (17 mg, 0.1 mmol) followed by purification by prep-HPLC eluting with 10-100% MeCN in H$_2$O (0.1% TFA). Colourless amorphous solid (TFA salt, 48 mg, 0.09 mmol, 86%). $^1$H NMR (500 MHz, CDCl$_3$): δ 8.88 (1H, app s, Py-2H), 8.67 (1H, d, J 5.6 Hz, Py-6H), 8.34 (1H, app, s, Py-5H), 7.67 (1H, app t, J 5.6 Hz, Py-4H), 7.64 (1H, app s, Bn-2H), 7.57 (1H, app d, J 7.5 Hz, Bn-6H), 7.40 (1H, app t, J 7.5 Hz, Bn-5H), 7.35 (1H, app d, J 8.2 Hz, Bn-4H), 7.11 (1H, d, J 7.8 Hz, Ph-3H) 7.08 (1H, d, J 7.8 Hz, Ph-2H), 6.97-6.92 (2H, m, 7H and 8H), 6.90 (1H, dd, J 7.1 and 2.1 Hz, 9H), 5.33 (1H, d, J 13.3 Hz, 10-O—CH$_2{}^1$), 5.23 (1H, d, J 13.3 Hz, 10-O—CH$_2{}^1$), 4.43 (1H, app t, J 3.2 Hz, 6H), 3.56-3.51 (2H, m, N-Et-1H$_2$), 2.82-2.78 (2H, m, N-Et-2H$_2$), 2.66 (1H, dd, J 13.1 and 3.2 Hz, g-H$_2{}^1$), 2.46 (1H, dd, J 13.1 and 3.2 Hz, g-H$_2{}^1$), 2.32 (3H, s, Ph-4-CH$_3$), 1.50 (3H, s, 2-CH$_3$). $^{13}$C NMR (125 MHz, CDCl$_3$): δ 166.7 (CONH), 156.0 (C4), 147.1 (C10), 143.6 (Py-C6), 143.3 (Py-C2), 141.7 (C10a), 140.6 (Py-C5), 138.1 (Bn-C1), 136.1 (Ph-C4), 135.7 (Bn-C3), 135.6 (Ph-C1), 133.3 (Bn-C4), 129.4 (Ph-C2), 129.1 (Bn-C2), 128.9 (Bn-C5), 128.6 (Ph-C3), 125.9 (Bn-C6), 125.5 (Py-C4), 122.5 (C9), 121.9 (C8), 116.3 (C7), 85.7 (C2), 68.5 (10-O—CH$_2$), 45.1 (C6), 41.3 (N-Et-C1), 35.2 (N-Et-C2), 34.5 (Cg), 27.1 (2-CH$_3$), 21.0 (Ph-4-CH$_3$). HRMS (ESI): C$_{33}$H$_{33}$N$_4$O$_4$ [M+H]$^+$; Requires: 549.2496. Found: 549.2493.

Example 3-11: Preparation of 3-(2-Methyl-4-oxo-10-(pyridin-2-ylmethoxy)-5,6-dihydro-2H-2,6-methanobenzo[g][1,3,5]oxadiazocin-3(4H)-yl)-N-(4-methylphenethyl)benzamide, Compound A11

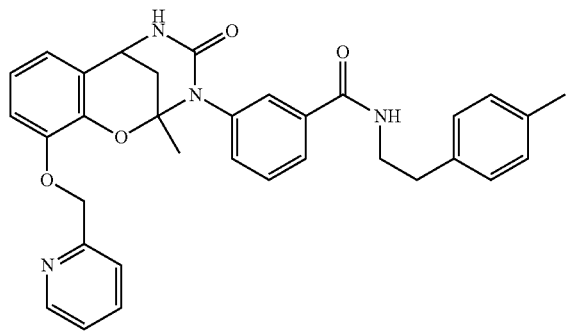

A11

By General Procedure G, using the phenol 2-5 (46 mg, 0.1 mmol) and 2-chloromethyl pyridine hydrochloride (17 mg, 0.1 mmol) followed by purification by prep-HPLC eluting with 10-100% MeCN in H$_2$O (0.1% TFA). Colourless amorphous solid (TFA salt, 43 mg, 0.08 mmol, 78%). $^1$H NMR (500 MHz, CDCl$_3$): δ 8.60 (1H, d, J 4.7 Hz, Py-6H), 7.92 (1H, d, J 5.6 Hz, Py-4H), 7.84 (1H, app, s, Py-5H), 7.67 (1H, app t, J 5.6 Hz, Py-4H), 7.60 (1H, app d, J 7.8 Hz, Bn-6H), 7.53 (1H, app s, Bn-2H), 7.37 (1H, app t, J 5.6 Hz, Py-3H), 7.32 (1H, app t, J 7.8 Hz, Bn-5H), 7.28 (1H, app d, J 7.8 Hz, Bn-4H), 7.02 (1H, d, J 7.8 Hz, Ph-3H), 6.98 (1H, d, J 7.8 Hz, Ph-2H), 6.88 (1H, app d, J 8.2 Hz, 7H), 6.84 (1H, app t, J 7.8 Hz, 8H), 6.79 (1H, d, J 7.8 Hz, 9H), 5.30 (2H, s, 10-O—CH$_2$), 4.35 (1H, app s, 6H), 3.50-3.43 (2H, m, N-Et-1H$_2$), 2.73-2.67 (2H, m, N-Et-2H$_2$), 2.56 (1H, dd, J 13.3 and 3.2 Hz, g-H$_2{}^1$), 2.39 (1H, dd, J 13.3 and 3.2 Hz, g-H$_2{}^1$), 2.24 (3H, s, Ph-4-CH$_3$), 1.50 (3H, s, 2-CH$_3$). $^{13}$C NMR (125 MHz, CDCl$_3$): δ 167.4 (CONH), 156.2 (C4), 147.8 (C10), 143.5 (Py-C4), 143.3 (Py-C6), 141.0 (C10a), 140.1 (Py-C5), 138.2 (Bn-C1), 136.5 (Ph-C4), 135.2 (Bn-C3), 135.1 (Ph-C1), 133.1 (Bn-C4), 129.2 (Ph-C2), 128.9 (Bn-C2), 128.6 (Bn-C5), 128.5 (Ph-C3), 125.5 (Py-C3), 125.2 (Bn-C6), 121.5 (C9), 121.0 (C8), 114.3 (C7), 85.4 (C2), 68.2 (10-O—CH$_2$), 45.1 (C6), 41.1 (N-Et-C1), 35.2 (N-Et-C2), 34.8 (Cg), 27.0 (2-CH$_3$), 19.0 (Ph-4-CH$_3$). HRMS (ESI): C$_{33}$H$_{33}$N$_4$O$_4$ [M+H]$^+$; Requires: 549.2496. Found: 549.2508.

Example 3-12: Preparation of 3-(10-((2-Aminopyridin-3-yl)methoxy)-2-methyl-4-oxo-5,6-dihydro-2H-2,6-methanobenzo[g][1,3,5]oxadiazocin-3(4H)-yl)-N-(4-methylphenethyl)benzamide, Compound A12

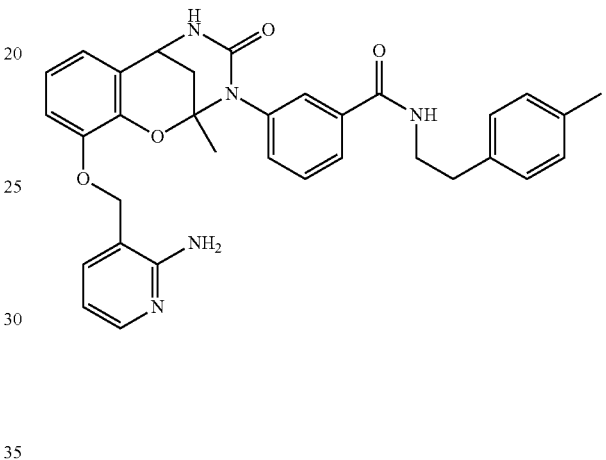

A12

By General Procedure G, using the phenol 2-5 (46 mg, 0.1 mmol) and 2-amino-3-chloromethyl pyridine hydrochloride (18 mg, 0.1 mmol) followed by purification by prep-HPLC eluting with 10-100% MeCN in H$_2$O (0.1% TFA). Colourless amorphous solid (TFA salt, 24 mg, 0.04 mmol, 43%). $^1$H NMR (500 MHz, MeOD): δ 8.12 (1H, d, J 7.1 Hz, Py-6H), 7.86 (1H, d, J 6.5 Hz, Py-5H), 7.74 (1H, d, J 8.1 Hz, Bn-6H), 7.61 (1H, app s, Bn-2H), 7.50-7.47 (1H, m, Bn-4H), 7.41-7.38 (1H, m, Bn-5H), 7.19 (1H, d, J 7.2 Hz, Py-4H), 7.13-7.08 (4H, m, Ph-2H and Ph-3H), 7.07-7.01 (2H, m, 7H and 8H), 6.94-6.92 (1H, m, 9H), 5.22 (1H, d, J 12.9 Hz, 10-O—CH$_2{}^1$), 5.12 (1H, d, J 12.9 Hz, 10-O—CH$_2{}^1$), 4.51 (1H, app s, 6H), 3.60-3.53 (2H, m, N-Et-1H$_2$), 2.90-2.84 (2H, m, N-Et-2H$_2$), 2.70 (1H, dd, J 13.4 and 2.8 Hz, g-H$_2{}^1$), 2.48 (1H, dd, J 13.4 and 2.8 Hz, g-H$_2{}^1$), 2.30 (3H, s, Ph-4-CH$_3$), 1.52 (3H, s, 2-CH$_3$). $^{13}$C NMR (125 MHz, MeOD): δ 168.0 (CONH), 156.5 (C4), 152.9 (Py-C2), 147.9 (C10), 147.6 (Py-C6), 142.8 (Py-C3), 141.6 (C10a), 141.3 (Py-C5), 138.1 (Bn-C1), 135.9 (Ph-C4), 135.6 (Bn-C3), 135.0 (Ph-C1), 133.6 (Bn-C4), 129.2 (Bn-C2), 128.9 (Ph-C2), 128.6 (Bn-C5), 128.3 (Ph-C3), 126.6 (Bn-C6), 126.6 (Py-C4), 126.1 (C6α), 122.7 (C9), 121.7 (C8), 115.4 (C7), 85.9 (C2), 67.7 (10-O—CH$_2$), 44.1 (C6), 41.4 (N-Et-C1), 34.7 (Cg), 33.9 (N-Et-C2), 25.8 (2-CH$_3$), 19.7 (Ph-4-CH$_3$). HRMS (ESI): C$_{33}$H$_{34}$N$_5$O$_4$ [M+H]$^+$; Requires: 564.2605. Found: 564.2611.

Example 3-13: Preparation of 3-(2-Methyl-4-oxo-10-(pyrimidin-5-ylmethoxy)-5,6-dihydro-2H-2,6-methanobenzo[g][1,3,5]oxadiazocin-3(4H)-yl)-N-(4-methylphenethyl)benzamide, Compound A13

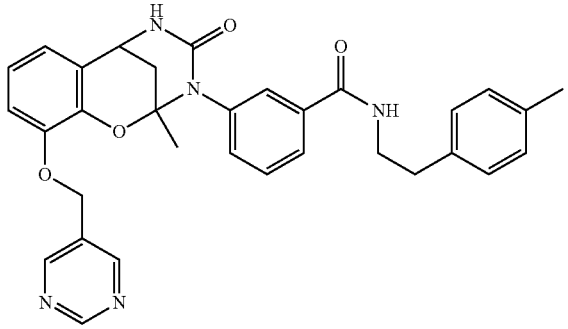

A13

By General Procedure G, using the phenol 2-5 (46 mg, 0.1 mmol) and 3-chloromethyl pyrimidine (14 mg, 0.1 mmol) followed by purification by prep-HPLC eluting with 10-100% MeCN in H$_2$O (0.1% TFA). Colourless amorphous solid (TFA salt, 46 mg, 0.08 mmol, 84%). $^1$H NMR (500 MHz, CDCl$_3$): δ 9.09 (1H, s, Py-2H), 8.76 (2H, s Py-4H and Py-6H), 7.54 (1H, app d, J 7.6 Hz, Bn-6H), 7.52 (1H, s, Bn-2H), 7.32 (1H, app t, J 7.8 Hz, Bn-5H), 7.28 (1H, app d, J 8.1 Hz, Bn-4H), 7.04 (2H, d, J 8.2 Hz, Ph-3H), 7.02 (2H, d, J 8.2 Hz, Ph-2H), 6.87 (1H, d, J 8.1 Hz, 7H), 6.84 (1H, app t, J 7.6 Hz, 8H), 6.77 (1H, d, J 7.6 Hz, 9H), 5.12 (1H, d, J 12.6 Hz, 10-O—CH$_2^1$), 5.02 (1H, d, J 12.6 Hz, 10-O—CH$_2^1$), 4.29 (1H, app d, J 3.2 Hz, 6H), 3.54-3.44 (2H, m, N-Et-1H$_2$), 2.73 (2H, app t, J 6.9 Hz, N-Et-2H$_2$), 2.54 (1H, dd, J 13.7 and 3.2 Hz, g-H$_2^1$), 2.33 (1H, dd, J 13.7 and 3.2 Hz, g-H$_2^1$), 2.25 (3H, s, Ph-4-CH$_3$), 1.41 (3H, s, 2-CH$_3$). $^{13}$C NMR (125 MHz, CDCl$_3$): δ 166.6 (CONH), 158.3 (Py-C2), 156.1 (Py-C4 and Py-C6), 156.0 (C4), 147.1 (C10), 141.6 (C10a), 138.0 (Bn-C1), 136.0 (Ph-C4), 135.9 (Bn-C3), 135.6 (Ph-C1), 133.0 (Bn-C4, verified through HMBC), 130.7 (Py-C5), 129.4 (Ph-C2), 129.2 (Bn-C2), 128.9 (Bn-C5), 128.7 (Ph-C3), 126.2 (Bn-C6), 125.9 (C6α), 122.4 (C9), 121.7 (C8), 116.0 (C7, verified through HMBC), 85.7 (C2), 67.4 (10-O—CH$_2$), 44.9 (C6), 41.4 (N-Et-C1), 35.2 (N-Et-C2), 34.5 (Cg), 27.1 (2-CH$_3$), 21.0 (Ph-4-CH$_3$). HRMS (ESI): C$_{32}$H$_{32}$N$_5$O$_4$ [M+H]$^+$; Requires: 550.2449. Found: 550.2431.

Example 3-14: Preparation of 3-(2-Methyl-10-((5-methylpyridin-3-yl)methoxy)-4-oxo-5,6-dihydro-2H-2,6-methanobenzo[g][1,3,5]oxadiazocin-3(4H)-yl)-N-(4-methylphenethyl)benzamide, Compound A14

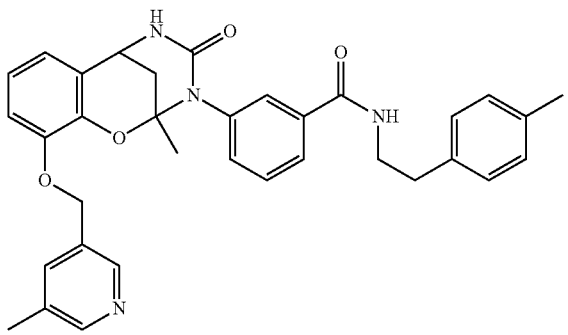

A14

By General Procedure G, using the phenol 2-5 (46 mg, 0.1 mmol) and 3-chloromethyl-5-methyl pyridine hydrochloride (18 mg, 0.1 mmol) followed by purification by prep-HPLC eluting with 10-100% MeCN in H$_2$O (0.1% TFA). Colourless amorphous solid (TFA salt, 40 mg, 0.07 mmol, 71%). $^1$H NMR (500 MHz, CDCl$_3$): δ 8.66 (1H, s, Py-6H), 8.47 (1H, s, Py-2H), 8.18 (1H, s, Py-4H), 7.58 (1H, s, Bn-2H), 7.52 (1H, app d, J 7.9 Hz, Bn-6H), 7.33 (1H, app t, J 7.9 Hz, Bn-5H), 7.28 (1H, app d, J 7.5 Hz, Bn-4H), 7.04 (2H, d, J 7.9 Hz, Ph-3H), 7.01 (2H, d, J 7.9 Hz, Ph-2H), 6.90-6.85 (3H, m, 7H, 8H and 9H), 5.28 (1H, d, J 12.9 Hz, 10-O—CH$_2^1$), 5.16 (1H, d, J 12.9 Hz, 10-O—CH$_2^1$), 4.37 (1H, app d, J 3.0 Hz, 6H), 3.49-3.44 (2H, m, N-Et-1H$_2$), 2.74-2.71 (2H, m, N-Et-2H$_2$), 2.54 (1H, dd, J 12.9 and 3.0 Hz, g-H$_2^1$), 2.41-2.37 (4H, m, g-H$_2^1$ and Py-5-CH$_3$), 2.25 (3H, s, Ph-4-CH$_3$), 1.44 (3H, s, 2-CH$_3$). $^{13}$C NMR (125 MHz, CDCl$_3$): δ 166.6 (CONH), 156.1 (C4), 147.0 (C10), 141.8 (C10a), 138.8 (Py-C5), 138.1 (Bn-C1), 137.0 (Py-C3), 136.2 (Ph-C4), 135.7 (Bn-C3), 135.6 (Ph-C1), 133.4 (Bn-C4, verified through HMBC), 129.4 (Ph-C2), 129.3 (Bn-C2), 128.9 (Bn-C5), 128.6 (Ph-C3), 126.0 (Bn-C6), 125.8 (C6α), 122.8 (C9), 121.9 (C8), 116.7 (C7), 85.7 (C2), 68.4 (10-O—CH$_2$), 45.0 (C6), 41.3 (N-Et-C1), 35.1 (N-Et-C2), 34.4 (Cg), 27.1 (2-CH$_3$), 21.0 (Py-5-CH$_3$), 18.5 (Ph-4-CH$_3$). HRMS (ESI): C$_{34}$H$_{35}$N$_4$O$_4$ [M+H]$^+$; Requires: 563.2653. Found: 563.2657.

Example 3-15: Preparation of 3-(10-((3,5-Dimethylisoxazol-4-yl)methoxy)-2-methyl-4-oxo-5,6-dihydro-2H-2,6-methanobenzo[g][1,3,5]oxadiazocin-3(4H)-yl)-N-(4-methylphenethyl)benzamide, Compound A15

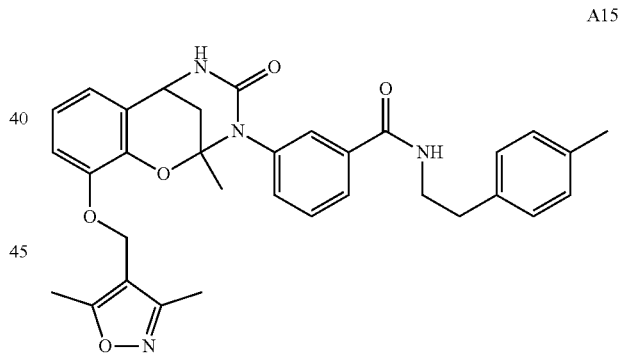

A15

By General Procedure G, using the phenol 2-5 (46 mg, 0.1 mmol) and 3-chloromethyl-3,5-dimethyl isoxazole (12 µL, 0.1 mmol) followed by purification by prep-HPLC eluting with 10-100% MeCN in H$_2$O (No TFA). Colourless amorphous solid (36 mg, 0.06 mmol, 64%). $^1$H NMR (500 MHz, CDCl$_3$): δ 7.67 (1H, s, Bn-2H), 7.41 (1H, s, Bn-6H), 7.34 (1H, app t, J 8.0 Hz, Bn-5H), 7.28 (1H, app d, J 7.9 Hz, Bn-4H), 7.06-7.02 (4H, m, Ph-3H and Ph-2H), 6.90-6.85 (2H, m, 7H, and 8H) 6.83-6.81 (1H, m, 9H), 4.77 (1H, d, J 11.7 Hz, 10-O—CH$_2^1$), 4.74 (1H, d, J 11.7 Hz, 10-O—CH$_2^1$), 4.33 (1H, app d, J 3.2 Hz, 6H), 3.65-3.58 (2H, m, N-Et-1H$_2$), 2.79-2.74 (2H, m, N-Et-2H$_2$), 2.57 (1H, dd, J 12.9 and 3.2 Hz, g-H$_2^1$), 2.34 (1H, dd, J 12.9 and 3.2 Hz, g-H$_2^1$), 2.26-2.22 (6H, m, isox-3-CH$_3$ and Ph-4-CH$_3$), 2.18 (3H, s, isox-5-CH$_3$), 1.40 (3H, s, 2-CH$_3$). $^{13}$C NMR (125 MHz, CDCl$_3$): δ 167.7 (CONH), 159.8 (isox-C3 and isox-C5), 155.9 (C4), 147.0 (C10), 137.7 (Bn-C1), 136.0 (Ph- C4), 135.9 (Bn-C3), 135.5 (Ph-C1), 133.0 (Bn-C4, verified through HMBC), 129.5 (Ph-C2), 129.4 (Bn-C2), 129.1 (Bn-C5), 128.7 (Ph-C3), 126.8 (Bn-C6), 125.9 (C6α), 121.9 (C9 and C8), 110.4 (C7), 85.6 (C2), 62.0 (10-O—$CH_2$), 45.1 (C6), 41.5 (N-Et-C1), 35.3 (N-Et-C2), 34.5 (Cg), 27.0 (2-$CH_3$), 21.1 (Ph-4-$CH_3$), 11.1 (isox-3-$CH_3$), 10.2 (isox-5-$CH_3$). HRMS (ESI): $C_{33}H_{35}N_4O_5$ $[M+H]^+$; Requires: 567.2602. Found: 567.2609.

Example 3-16: Preparation of 3-(2-Methyl-10-((1-methyl-1H-imidazol-2-yl)methoxy)-4-oxo-5,6-dihydro-2H-2,6-methanobenzo[g][1,3,5]oxadiazocin-3(4H)-yl)-N-(4-methylphenethyl)benzamide, Compound A16

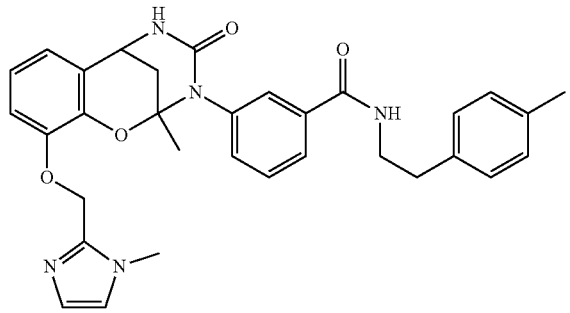

A16

By General Procedure G, using the phenol 2-5 (46 mg, 0.1 mmol) and 2-(chloromethyl)-1methyl imidazole hydrochloride (16 mg, 0.1 mmol) followed by purification by prep-HPLC eluting with 10-100% MeCN in $H_2O$ (0.1% TFA). Colourless amorphous solid (TFA salt, 36 mg, 0.07 mmol, 65%). $^1$H NMR (500 MHz, $CDCl_3$): δ 7.51 (1H, app d, J 7.3 Hz, Bn-6H), 7.46 (1H, s, Bn-2H), 7.29 (1H, app t, J 7.6 Hz, Bn-5H), 7.20-7.17 (2H, m, Bn-4H and imid-4H), 7.05-6.96 (6H, m, Ph-3H, Ph-2H, imid-5H, and 7H), 6.87-6.82 (2H, m, 8H and 9H), 5.44 (2H, app s, 10-O—$CH_2$), 4.32 (1H, app s, 6H), 3.84 (3H, imid-1-$CH_3$), 3.52-3.45 (2H, m, N-Et-1$H_2$), 2.75-2.70 (2H, m, N-Et-2$H_2$), 2.52 (1H, dd, J 13.3 and 2.7 Hz, g-$H_2^1$), 2.35 (1H, dd, J 13.3 and 2.7 Hz, g-$H_2^1$), 2.24 (3H, s, Ph-4-$CH_3$), 1.36 (3H, s, 2-$CH_3$). $^{13}$C NMR (125 MHz, $CDCl_3$): δ 167.2 (CONH), 155.9 (C4), 145.8 (C10), 142.2 (imid-C2), 141.9 (C10a), 138.1 (Bn-C1), 136.2 (Ph-C4), 135.8 (Bn-C3), 135.6 (Ph-C1), 133.4 (Bn-C4, verified through HMBC), 129.4 (Ph-C2 and Bn-C2), 128.9 (Bn-C5), 128.6 (Ph-C3), 126.1 (Bn-C6), 126.0 (C6α), 123.7 (imid-C4), 123.3 (imid-C5), 122.1 (C9), 120.1 (C8), 118.1 (C7), 85.7 (C2), 61.3 (10-O—$CH_2$), 44.8 (C6), 41.4 (N-Et-C1), 35.1 (N-Et-C2), 35.0 (imid-1-$CH_3$), 34.2 (Cg), 27.0 (2-$CH_3$), 21.0 (Ph-4-$CH_3$). HRMS (ESI): $C_{32}H_{34}N_5O_4$ $[M+H]^+$; Requires: 552.2605. Found: 552.2597.

Biological Examples

Materials
Cell Lines:
  CHOK1 cells: Sigma, 85050302
  DLD-1 cells: Horizon Discovery
  DLD-1-GLUT-1(−/−) cells: Horizon Discovery, HD R00-024
  CHO-hGLUT2 over-expressing stable cell line: Creative Biogene
  CHO-hGLUT4 over-expressing stable cell line: Creative Biogene
Cell Culture Media:
  RPM11640 (P04-22100)—PAN-Biotech
  RPMI w/o glucose w/o phenolred (P04-16530)—PAN-Biotech
  FCS (P30-3302P+)—PAN-Biotech
  L-Glutamine (200 mM, P04-80100)—PAN-Biotech
  Trypsin/EDTA (P10-019100)—PAN-Biotech
  DMEM (P04-03550)—PAN-Biotech
  DMEM w/o Glc w/o Gln (P04-01548S1)—PAN-Biotech
  Sodium Pyruvate (100 mM, P04-43100)—PAN-Biotech
  L-Glutamine (200 mM, P04-80050)—PAN-Biotech
  Trypsin/EDTA (P10-023100)—PAN-Biotech
  Penicillin-Streptomycin (P06-07100)—PAN-Biotech
  FBS (10500-084)—Invitrogen
  Non-essential amino acids (P08-32100)—PAN-Biotech
  RPM11640 (P04-16500)—PAN-Biotech
  Insulin from bovine pancreas (16634, SIGMA) MW: 5734 Da
Cell Culture DLD-1, DLD-1-GLUT-1 (−/−) and CHOK1 cells were cultured at 37° C. with 5% $CO_2$ using RPM11640 containing 10% FBS and 2 mM L-Glutamine. All cell lines were regularly assayed for *Mycoplasma* and were confirmed to be *Mycoplasma*-free.

Generation of SLC2A4-Overexpressing CHOK1 Cell Line

CHOK1-SLC2A4 cells were generated by transfection of CHOK1 cells with pCMV6-Entry-GLUT4 (Origene #SC125240) using Lipofectamin2000 according to the supplier's instructions. Briefly, 1.5E5 cells/well CHOK1 cells were seeded in 6-well cell culture plates. After overnight incubation, DNA-lipid complexes (2 μg plasmid DNA, DNA:lipid ratio 1:10) were prepared in OptiMEM and then added to the cells. After 5 days incubation, 800 μg G418 was added to the culture medium to generate a stable polyclone. For monoclone selection, single cells were re-plated in 96-well plates, expanded and selected by transgene overexpression and functional performance.

Example 8-1: Measurement of Inhibitory Activity to GLUTs

GLUT 1, 2, 3 and 4 Transporter Activity Assays

Assays were based on the specificity assays reported by Kapoor et al., Proceedings of the National Academy of Sciences 2016, 113 (17) 4711-4716. For GLUT1, GLUT2, GLUT3 and GLUT4 specificity testing DLD1, CHO-hGLUT2, DLD-1-GLUT1−/− and CHO-hGLUT4 cell lines were used.

For evaluating the inhibitory activity of the compounds of the present invention to the GLUT 1, 3 and 4, the following ranges for the $IC_{50}$ [nM] were applied:

| | |
|---|---|
| $IC_{50}$ ≤ 300 nM | ++++ |
| 300 nM < $IC_{50}$ ≤ 1,000 nM | +++ |
| 1,000 nM < $IC_{50}$ ≤ 4,000 nM | ++ |
| 4,000 nM < $IC_{50}$ ≤ 10,000 nM | + |
| 10,000 nM < $IC_{50}$ ≤ 25,000 nM | o |
| $IC_{50}$ > 25,000 nM | oo |

TABLE 1

GLUTs inhibitory activity of the compounds of general formula (I):

| Comp. | GLUT1 | GLUT2 | GLUT3 | GLUT4 |
|---|---|---|---|---|
| A01 | ++++ | o | ++++ | o |
| A02 | ++ |  | ++ | oo |
| A03 | +++ |  | +++ | + |
| A04 | +++ |  | +++ | oo |
| A05 | ++++ |  | ++++ | + |
| A07 | +++ |  | +++ | + |
| A08 | ++++ |  | +++ | ++ |
| A09 | ++++ |  | +++ | + |
| A10 | ++++ | + | +++ | + |
| A11 | ++++ | + | ++++ | ++ |
| A12 | ++ |  | ++ | oo |
| A13 | +++ |  | +++ | oo |
| A14 | ++++ |  | ++++ | ++ |
| A15 | +++ | o | +++ | + |
| A16 | ++ | oo |  | oo |
| A19 | o |  | ++ | oo |
| A21 | ++ | oo | ++ | o |
| A22 | + |  | ++ | oo |
| A23 | +++ | oo | +++ | + |
| A24 | o |  | + | o |
| A26 | oo |  | + | o |
| A33 | +++ | oo | +++ | ++ |
| A34 | +++ |  | +++ | +++ |
| A35 | +++ | oo | +++ | o |
| A36 | +++ | oo | +++ | + |
| A37 | ++ | oo | ++ | o |
| A38 | o |  | + | o |
| A39 | o |  | + | o |
| Ref.1 | oo | oo | oo | oo |
| Ref.2 | o |  | + | oo |
| Ref.3 | o |  | o | oo |

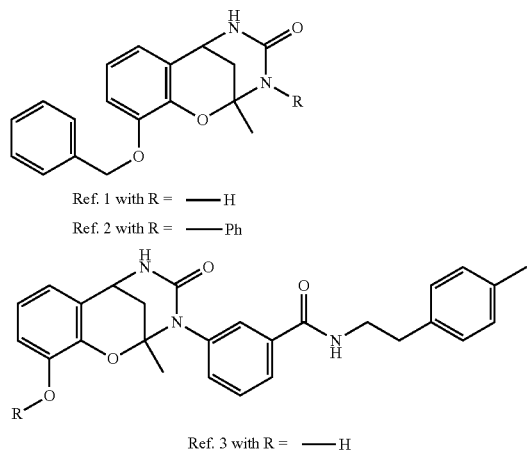

Ref. 1 with R = ——H
Ref. 2 with R = ——Ph

Ref. 3 with R = ——H

Example 8-2: 2-Deoxy-Glucose (2-DG) Uptake Assay

The 2-DG uptake assay was carried out as described by Yamamoto N. et al. with slight modifications (Crane, E. A.; Gademann, K., Capturing Biological Activity in Natural Product Fragments by Chemical Synthesis. *Angewandte Chemie International Edition* 2016, 55 (12), 3882-3902; Murray, C. W.; Rees, D. C., The rise of fragment-based drug discovery. *Nature Chemistry* 2009, 1 (3), 187-192.). Briefly, 40,000 HCT116 or CHO cells were seeded in black, clear bottom 96-well plates and allowed to attach overnight. Cells were incubated with compounds or DMSO and 1 mM 2-DG in glucose-free KRB buffer (20 mM HEPES, 5 mM KH2PO4, 1 mM MgSO4, 1 mM CaCl$_2$), 136 mM NaCl, 0.1% BSA, pH 7.4) for 30 min. In the case of GLUT-4 transfected cells, Insulin (100 µg/mL) was added to the buffer. Cells were then washed and lysed in 0.06 M HCl and 1% CHAPS for 15 min at 65° C. while shaking. The amount of 2-DG in the lysate was determined by means of enzyme-coupled assay. For this 6.4 U/mL glucose-6-phosphate dehydrogenase, 0.2 U/mL diaphorase, 0.1 mM NADP$^+$ and 0.025 mg/mL resazurin were added to the lysates. Resorufin fluorescence was determined as a measure of 2-DG uptake at ex/em 535/590 nm with a Tecan Infinite M200 plate reader (Tecan). Blank values were subtracted from all readings and values were normalized to the DMSO control.

Assay protocols for 2-deoxy-Glucose (2-DG) Uptake Assay with DLD1 or DLD1-Glut1(−/−) cells or 7,000 CHOK1-SLC2A4 cells lines:

14,000 DLD1 or DLD1-Glut1 (−/−) cells or 7,000 CHOK1-SLC2A4 cells were seeded in black, clear bottom 384-well plates in glucose- and phenolred-free RPM11640 medium supplemented with 1% FCS and 2 mM L-glutamine and allowed to attach overnight. Next day, cells were washed and incubated with compounds or DMSO and 1 mM 2-DG in glucose- and phenolred-free RPM11640 medium for 30 min. Cells were then washed and lysed in 0.06 M HCl and 1% CHAPS for 15 min at 65° C. The amount of 2-DG in the lysate was determined by means of enzyme-coupled assay. For this 16 U/mL glucose-6-phosphate dehydrogenase, 0.2 U/mL diaphorase, 0.1 mM NADP$^+$ and 10 µM resazurin were added to the lysates. Resorufin fluorescence was determined as a measure of 2-DG uptake at ex/em 535/590 nm with a Victor Multilabel plate reader (Perkin Elmer). Blank values were subtracted from all readings and values were normalized to the DMSO control.

2-DG Uptake Assay

For evaluating the inhibitory activity of the compounds of the present invention to the GLUT 1, 3 and 4, the following ranges for the IC$_{50}$ [µM] were applied:

| | |
|---|---|
| IC$_{50}$ ≤ 5 µM | ++++ |
| 5 µM < IC$_{50}$ ≤ 10 µM | ++ |
| 10 µM < IC$_{50}$ ≤ 30 µM | + |
| IC$_{50}$ > 30 µM | o |

TABLE 2 inhibitory activity of the compounds
of general formula (I) to DG Uptake:
IC$_{50}$ determined for the inhibition
of 2-DG uptake in HCT116 cells.

| Comp. | IC$_{50}$ |
|---|---|
| A02 | +++ |
| A03 | +++ |
| A04 | +++ |
| A05 | +++ |
| A06 | +++ |
| A07 | +++ |

Example 8-3: Indirect Measurement of GLUT2 (SLC2A2) Activity by Quantification of Intracellular ATP Levels A combination of small-molecule inhibitors of mitochondrial electron transport chain and glucose catabolism synergistically suppress ATP production and impair cellular viability (Ulanovskaya et al., 2008, 2011; Liu, et al. 2001). We therefore used CHOK1 cells overexpressing SLC2A2 (CHOK1-SLC2A2) in combination with an oxidative phosphorylation inhibitor (Rotenon) to identify GLUT2 inhibitors. CHOK1-SLC2A2 cells were purchased from creative biogene (catNo: CSC-SC014484) and maintained in RPM11640 supplemented with 10% FBS and 2 mM L-Glutamine. For the Glut2-ATP-Assay, 7,500 cells were seeded in black, clear bottom 384-well plates directly in glucose- and phenolred-free RPM11640 medium supplemented with 1% FCS and 2 mM L-glutamine and cultured overnight to reduce intracellular ATP levels. Next day, cells were washed and incubated with 1 mM Rotenone and compounds or DMSO and 2.5 mM fructose in glucose- and phenolred-free RPM11640 medium for 40 min. The CellTiter-Glo® Luminescence Viability Assay from Promega was used to measure ATP levels. Luminescence was measured with a Victor Multilabel plate reader (Perkin Elmer). Blank values were subtracted from all readings and values were normalized to the DMSO control.

The invention claimed is:

1. A compound of general formula (I)

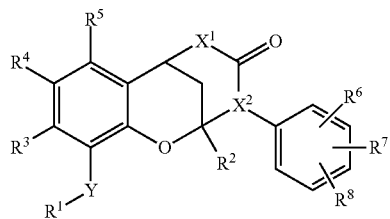

wherein
$X^1$ is —O— or —NR$^N$—;
R$^N$ is —H, —CH$_3$, —CH$_2$CH$_3$, —CH$_2$CH$_2$CH$_3$, —CH(CH$_3$)$_2$, -cyclo-C$_3$H$_5$, —C$_4$H$_9$, —CH$_2$CH(CH$_3$)$_2$, —C(CH$_3$)$_3$, or -cyclo-C$_4$H$_7$;
$X^2$ is

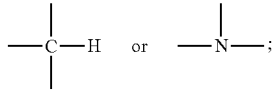

Y is a bond, —O— or —S—;
R$^1$ represents —(CH$_2$)$_m$-A;
m is an integer selected from 0, 1, 2 or 3;
A represents C3-C12 mono-, bi-, tri-, tetra-, or pentacycloalkyl, or

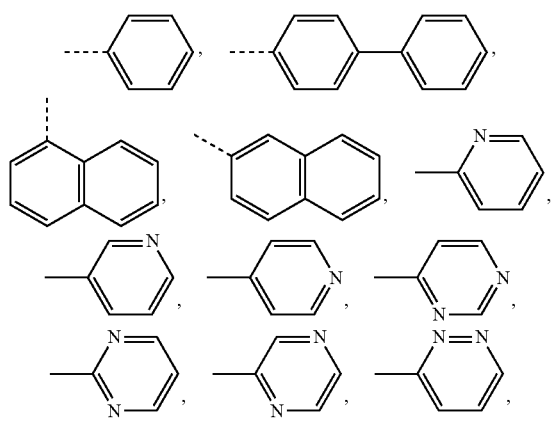

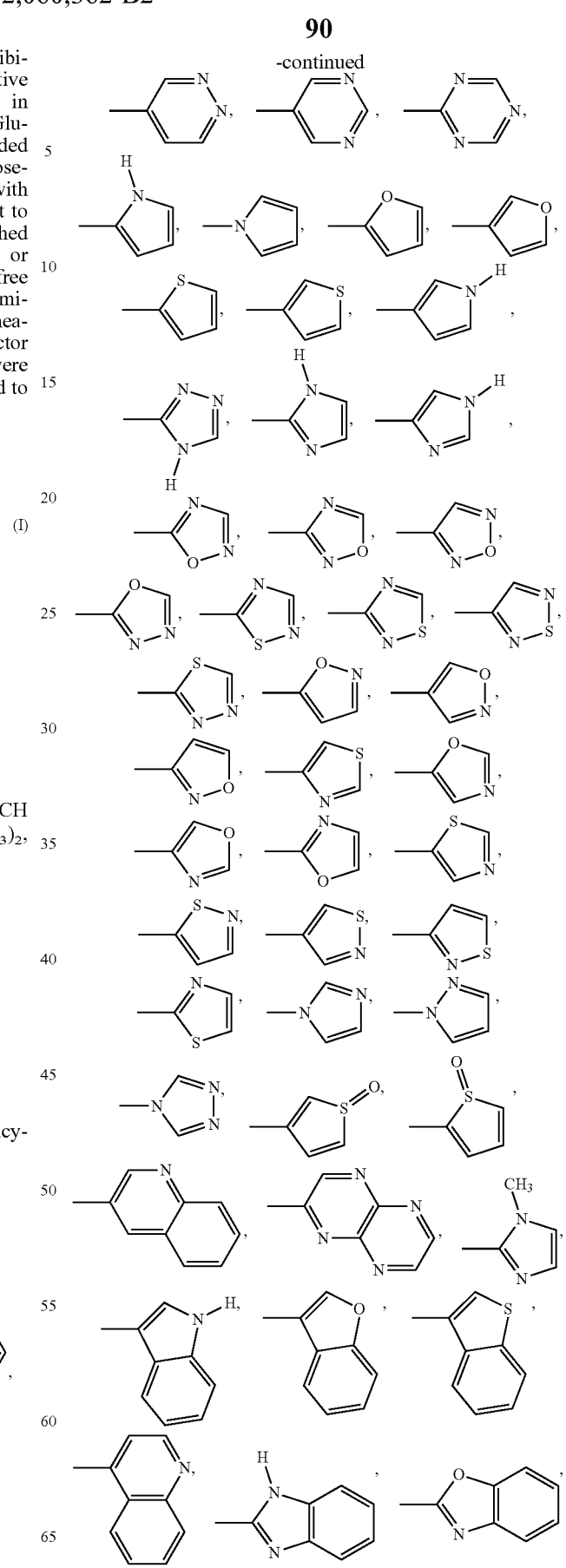

-continued

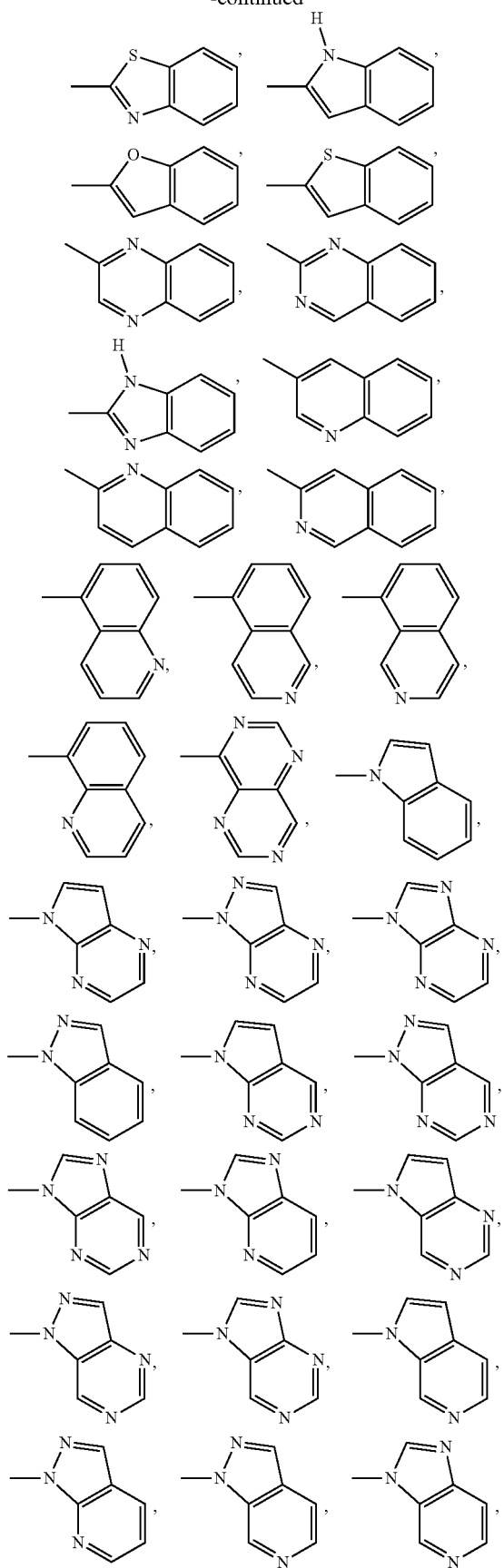

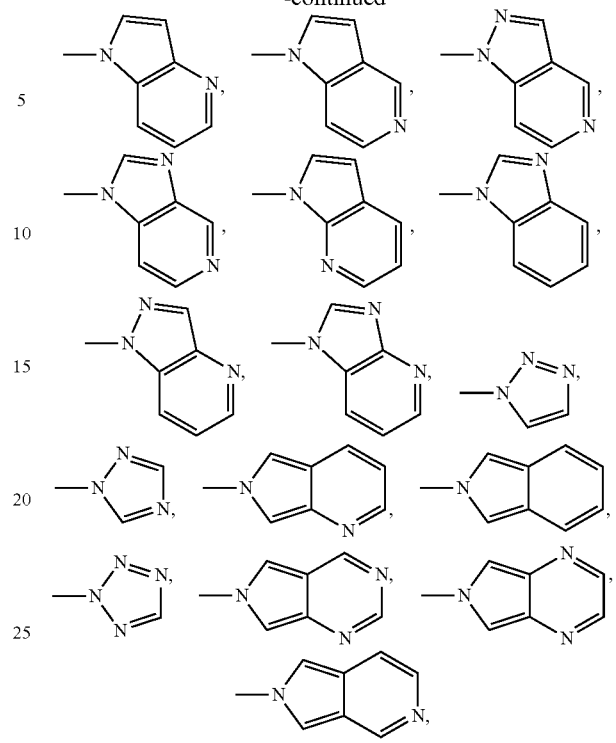

wherein these residues can be substituted with 1 to 3 substituents selected from $Z^1$, $Z^2$, $Z^3$;

$R^2$ represents —H, —CH$_3$ or —CH$_2$CH$_3$;

$R^3$, $R^4$, $R^5$, $R^6$ and $R^7$ represent independently of each other —H, —F, —Cl, —CN, —CH$_3$ or —CF$_3$;

$R^8$ represents —CO—O—(CH$_2$)$_n$—B, —CO—O—(CH$_2$)$_n$—OB, —CO—NR'—(CH$_2$)$_n$—B, —CO—NR'—(CH$_2$)$_n$—OB, —CO—B* or —R$^7$;

R' represents —H or —CH$_3$;

n is an integer selected from 0, 1, 2 or 3;

B* represents

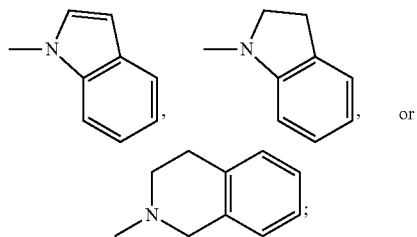

wherein these residues can be substituted with 1 to 3 substituents selected from $Z^4$, $Z^5$, $Z^6$;

B represents C1-C7-alkyl, C3-C6-cycloalkyl,

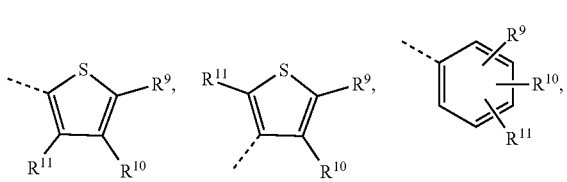

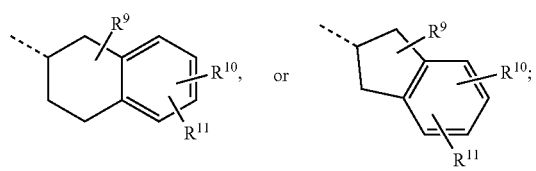

$R^9$, $R^{10}$, $R^{11}$, and $Z^1$-$Z^9$, represent independently of each other —H, —F, —Cl, —CN, —NO$_2$, —NH$_2$, —CF$_3$, —CH$_3$, —CH$_2$CH$_3$, —CH$_2$CH$_2$CH$_3$, —CH(CH$_3$)$_2$, —C(CH$_3$)$_3$, -cyclo-C3H$_5$; or $R^9$ and $R^{10}$, or $R^{10}$ and $R^{11}$ form together

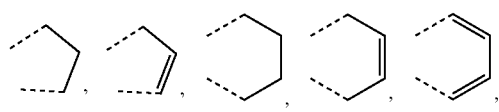

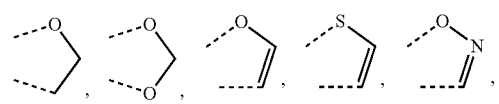

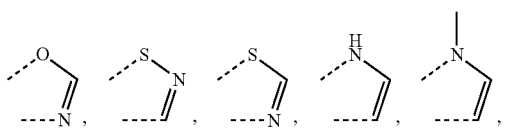

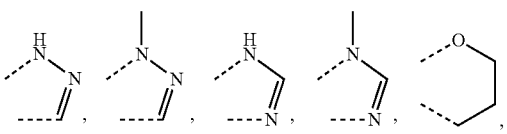

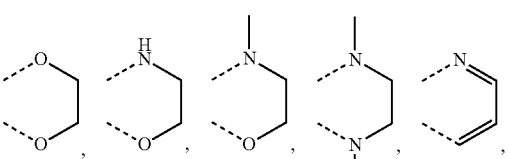

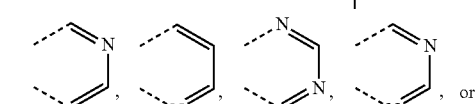

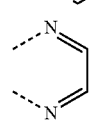

wherein these residues can be substituted with 1 to 3 substituents selected from $Z^7$, $Z^8$, $Z^9$;

B or an enantiomer, a diastereomer, a tautomer, or a pharmaceutically acceptable salt thereof.

2. The compound according to claim 1, wherein the compound has the formula (II)

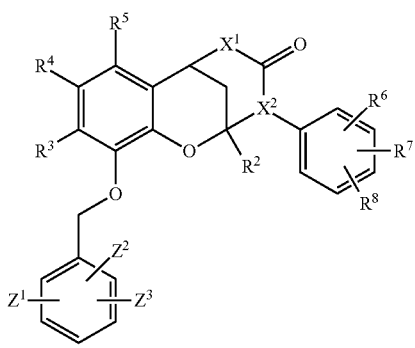

wherein $R^2$-$R^8$, $X^1$, $X^2$ and $Z^1$-$Z^3$ have the meanings as defined in claim 1.

3. The compound according to claim 1, wherein the compound has the formula (III)

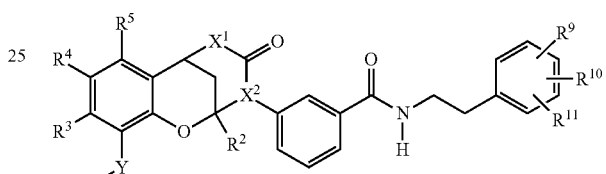

wherein $R^1$-$R^5$, $R^9$-$R^{11}$, $X^1$, $X^2$ and Y have the meanings as defined in claim 1.

4. The compound according to claim 1, wherein the compound has the formula (IV)

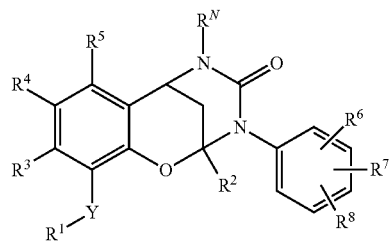

wherein $R^1$-$R^8$ and Y have the meanings as defined in claim 1.

5. The compound according to claim 1, wherein the compound has any of the formulae (V), (Va), (Vb), and (Vc), (V)

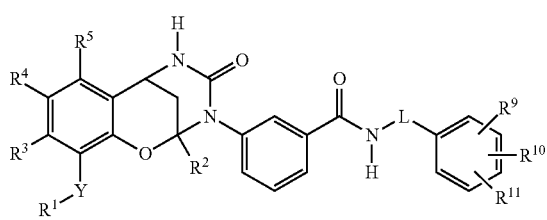

-continued (Va)
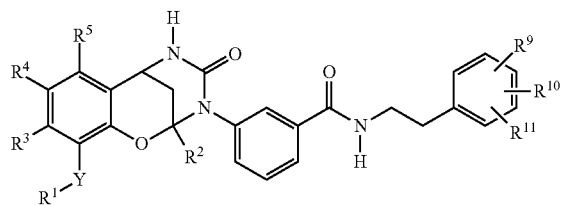

(Vb)
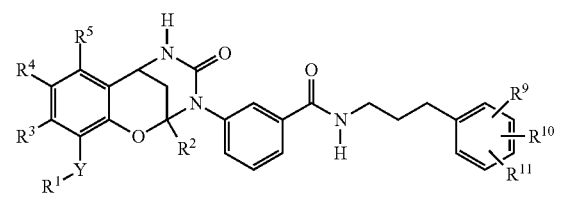

(Vc)
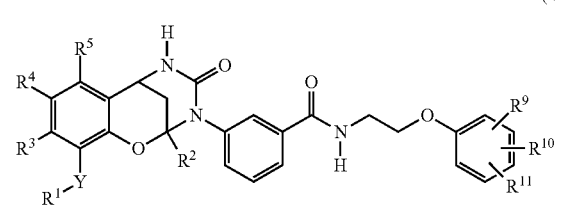

wherein $R^1$-$R^5$, $R^9$-$R^{11}$ and Y have the meanings as defined in claim 1 and L represents —$CH_2$—$CH_2$—, —$CH_2$—$CH_2$—$CH_2$—, or —$CH_2$—$CH_2$—O—.

6. The compound according to claim 1, wherein the compound has the formula (VI)

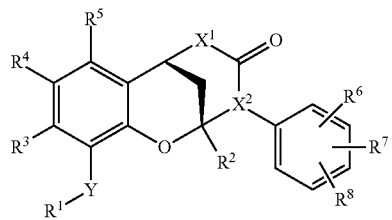

wherein $R^1$-$R^8$, $X^1$, $X^2$ and Y have the meanings as defined in claim 1.

7. The compound according to claim 1, wherein $R^1$ represents

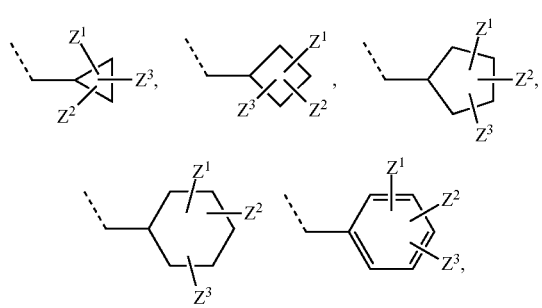

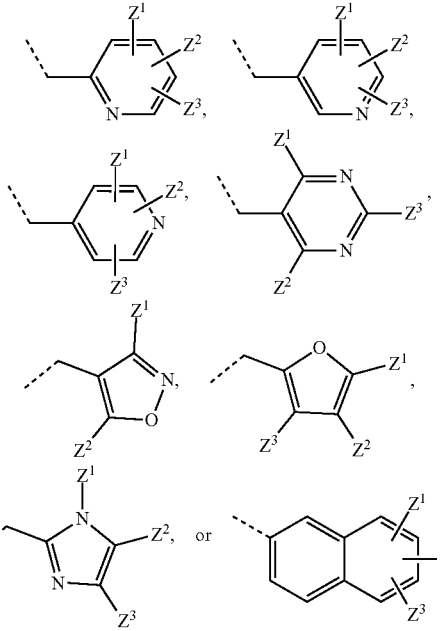

wherein $Z^1$, $Z^2$ and $Z^3$ have the meanings as defined in claim 1.

8. The compound according to claim 1, selected from the group consisting of:
- 3-(10-(Benzyloxy)-2-methyl-4-oxo-5,6-dihydro-2H-2,6-methanobenzo[g][1,3,5]oxadiazocin-3(4H)-yl)-N-(4-methylphenethyl)benzamide,
- 3-(2-Methyl-10-((2-methylbenzyl)oxy)-4-oxo-5,6-dihydro-2H-2,6-methanobenzo[g][1,3,5]oxadiazocin-3(4H)-yl)-N-(4-methylphenethyl)benzamide,
- 3-(2-Methyl-10-((4-nitrobenzyl)oxy)-4-oxo-5,6-dihydro-2H-2,6-methanobenzo[g][1,3,5]oxadiazocin-3(4H)-yl)-N-(4-methylphenethyl)benzamide,
- 3-(10-((3-Chlorobenzyl)oxy)-2-methyl-4-oxo-5,6-dihydro-2H-2,6-methanobenzo[g][1,3,5]oxadiazocin-3(4H)-yl)-N-(4-methylphenethyl)benzamide,
- 3-(10-((4-Cyanobenzyl)oxy)-2-methyl-4-oxo-5,6-dihydro-2H-2,6-methanobenzo[g][1,3,5]oxadiazocin-3(4H)-yl)-N-(4-methylphenethyl)benzamide,
- 3-(10-((4-(tert-Butyl)benzyl)oxy)-2-methyl-4-oxo-5,6-dihydro-2H-2,6-methanobenzo[g][1,3,5]oxadiazocin-3(4H)-yl)-N-(4-methylphenethyl)benzamide,
- 3-(10-(Furan-2-ylmethoxy)-2-methyl-4-oxo-5,6-dihydro-2H-2,6-methanobenzo[g][1,3,5]oxadiazocin-3(4H)-yl)-N-(4-methylphenethyl)benzamide,
- 3-(10-(Cyclopropylmethoxy)-2-methyl-4-oxo-5,6-dihydro-2H-2,6-methanobenzo[g][1,3,5]oxadiazocin-3(4H)-yl)-N-(4-methylphenethyl)benzamide,
- 3-(2-Methyl-4-oxo-10-(pyridin-4-ylmethoxy)-5,6-dihydro-2H-2,6-methanobenzo[g][1,3,5]oxadiazocin-3(4H)-yl)-N-(4-methylphenethyl)benzamide,
- 3-(2-Methyl-4-oxo-10-(pyridin-3-ylmethoxy)-5,6-dihydro-2H-2,6-methanobenzo[g][1,3,5]oxadiazocin-3(4H)-yl)-N-(4-methylphenethyl)benzamide,
- 3-(2-Methyl-4-oxo-10-(pyridin-2-ylmethoxy)-5,6-dihydro-2H-2,6-methanobenzo[g][1,3,5]oxadiazocin-3(4H)-yl)-N-(4-methylphenethyl)benzamide,
- 3-(10-((2-Aminopyridin-3-yl)methoxy)-2-methyl-4-oxo-5,6-dihydro-2H-2,6-methanobenzo[g][1,3,5]oxadiazocin-3(4H)-yl)-N-(4-methylphenethyl)benzamide, 3-(2-Methyl-4-oxo-10-(pyrimidin-5-ylmethoxy)-5,6-dihydro-2H-2,6-methanobenzo[g][1,3,5]oxadiazocin-3(4H)-yl)-N-(4-methylphenethyl)benzamide, 3-(2-Methyl-10-((5-methylpyridin-3-yl)methoxy)-4-oxo-5,6-dihydro-2H-2,6-methanobenzo[g][1,3,5]oxadiazocin-3(4H)-yl)-N-(4-methylphenethyl)benzamide, 3-(10-((3,5-Dimethylisoxazol-4-yl)methoxy)-2-methyl-4-oxo-5,6-dihydro-2H-2,6-methanobenzo[g][1,3,5]oxadiazocin-3(4H)-yl)-N-(4-methylphenethyl)benzamide, 3-(2-Methyl-10-((1-methyl-1H-imidazol-2-yl)methoxy)-4-oxo-5,6-dihydro-2H-2,6-methanobenzo[g][1,3,5]oxadiazocin-3(4H)-yl)-N-(4-methylphenethyl)benzamide, 3-(3-(1H-indole-1-carbonyl)phenyl)-10-(benzyloxy)-2-methyl-5,6-dihydro-2H-2,6-methanobenzo[g][1,3,5]oxadiazocin-4(3H)-one, 10-(benzyloxy)-2-methyl-3-(3-(1,2,3,4-tetrahydroisoquinoline-2-carbonyl)phenyl)-5,6-dihydro-2H-2,6-methanobenzo[g][1,3,5]oxadiazocin-4(3H)-one, 10-(benzyloxy)-3-(3-(indoline-1-carbonyl)phenyl)-2-methyl-5,6-dihydro-2H-2,6-methanobenzo[g][1,3,5]oxadiazocin-4(3H)-one, 3-(10-(benzyloxy)-2-methyl-4-oxo-5,6-dihydro-2H-2,6-methanobenzo[g]-[1,3,5]oxadiazocin-3(4H)-yl)-N-methyl-N-(2-phenoxyethyl)benzamide, 3-(10-(benzyloxy)-2-methyl-4-oxo-5,6-dihydro-2H-2,6-methanobenzo[g][1,3,5]oxadiazocin-3(4H)-yl)-N-(2-phenoxyethyl)benzamide, 4-methylphenethyl 3-(10-(benzyloxy)-2-methyl-4-oxo-5,6-dihydro-2H-2,6-methanobenzo[g][1,3,5]oxadiazocin-3(4H)-yl)benzoate, 3-(10-(benzyloxy)-2-methyl-4-oxo-5,6-dihydro-2H-2,6-methanobenzo[g]-[1,3,5]oxadiazocin-3(4H)-yl)-N-methyl-N-(4-methylphenethyl)benzamide, 3-(10-(benzyloxy)-2-methyl-4-oxo-5,6-dihydro-2H-2,6-methanobenzo[g]-[1,3,5]oxadiazocin-3(4H)-yl)-N-(2,3-dihydro-1H-inden-2-yl)benzamide, 2,3-dihydro-1H-inden-2-yl 3-(10-(benzyloxy)-2-methyl-4-oxo-5,6-dihydro-2H-2,6-methanobenzo[g][1,3,5]oxadiazocin-3(4H)-yl)benzoate, 3-(10-(benzyloxy)-2-methyl-4-oxo-5,6-dihydro-2H-2,6-methanobenzo[g]-[1,3,5]oxadiazocin-3(4H)-yl)-N-(1,2,3,4-tetrahydronaphthalen-2-yl)benzamide, 1,2,3,4-tetrahydronaphthalen-2-yl 3-(10-(benzyloxy)-2-methyl-4-oxo-5,6-dihydro-2H-2,6-methanobenzo[g][1,3,5]oxadiazocin-3(4H)-yl)benzoate, 3-(10-(cyclobutylmethoxy)-2-methyl-4-oxo-5,6-dihydro-2H-2,6-methanobenzo[g][1,3,5]oxadiazocin-3(4H)-yl)-N-(4-methylphenethyl)benzamide, 3-(10-(cyclopentylmethoxy)-2-methyl-4-oxo-5,6-dihydro-2H-2,6-methanobenzo[g][1,3,5]oxadiazocin-3(4H)-yl)-N-(4-methylphenethyl)benzamide, 3-(10-(cyclohexylmethoxy)-2-methyl-4-oxo-5,6-dihydro-2H-2,6-methanobenzo[g][1,3,5]oxadiazocin-3(4H)-yl)-N-(4-methylphenethyl)benzamide, 3-(10-(bicyclo[2.2.1]heptan-1-yl-methoxy)-2-methyl-4-oxo-5,6-di-hydro-2H-2,6-methanobenzo[g]-[1,3,5]oxadiazocin-3(4H)-yl)-N-(4-methylphenethyl)benzamide, 3-(10-(bicyclo[1.1.1]pentan-1-yl-methoxy)-2-methyl-4-oxo-5,6-di-hydro-2H-2,6-methanobenzo[g]-[1,3,5]oxadiazocin-3(4H)-yl)-N-(4-methylphenethyl)benzamide, 3-(10-(benzyloxy)-2-methyl-4-oxo-5,6-dihydro-2H-2,6-methanobenzo[g][1,3,5]oxadiazocin-3(4H)-yl)-N-(3-phenylpropyl)benzamide, 3-(10-(benzyloxy)-2-methyl-4-oxo-5,6-dihydro-2H-2,6-methanobenzo[g][1,3,5]oxadiazocin-3(4H)-yl)-N-(1-quinolin-6-yl-ethyl)benzamide, 3-(10-(benzyloxy)-2-methyl-4-oxo-5,6-dihydro-2H-2,6-methanobenzo[g][1,3,5]oxadiazocin-3(4H)-yl)-N-(2-(4-methylphenoxy)ethyl)benzamide, 3-(10-(benzyloxy)-2-methyl-4-oxo-5,6-dihydro-2H-2,6-methanobenzo[g][1,3,5]oxadiazocin-3(4H)-yl)-N-(phenethyl)benzamide, methyl 3-(10-(benzyloxy)-2-methyl-4-oxo-5,6-dihydro-2H-2,6-methanobenzo[g][1,3,5]oxadiazocin-3(4H)-yl)benzoate, 3-(10-(benzyloxy)-2-methyl-4-oxo-5,6-dihydro-2H-2,6-methanobenzo[g][1,3,5]oxadiazocin-3(4H)-yl)-N-(ethyl)benzamide, and 3-(10-(benzyloxy)-2-methyl-4-oxo-5,6-dihydro-2H-2,6-methanobenzo[g][1,3,5]oxadiazocin-3(4H)-yl)-N-(benzyl)benzamide.

9. A pharmaceutical composition containing at least one compound according to claim 1 as an active ingredient, together with at least one pharmaceutically acceptable carrier, excipient and/or diluent.

* * * * *